(12) United States Patent
Gillis et al.

(10) Patent No.: US 10,912,732 B2
(45) Date of Patent: Feb. 9, 2021

(54) CLEAR SHAMPOO COMPOSITION CONTAINING SILICONE POLYMERS

(71) Applicant: The Procter & Gamble Company, Cincinnati, OH (US)

(72) Inventors: Jade Yvonne Gillis, Norwood, OH (US); Robert Wayne Glenn, Jr., Liberty Township, OH (US); Dariush Hosseinpour, Mason, OH (US); Brian Michael Hurley, Blanchester, OH (US); Tiffany Tien-Yun Yang, Loveland, OH (US); Jean Jianqun Zhao, Cincinnati, OH (US); Michael Albert Snyder, Mason, OH (US); Roland Wagner, Bonn Beuel (DE); Albert Schnering, Leverkusen (DE); Katharina Streicher, Leverkusen (DE)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/226,914

(22) Filed: Dec. 20, 2018

(65) Prior Publication Data
US 2019/0183777 A1   Jun. 20, 2019

Related U.S. Application Data

(60) Provisional application No. 62/608,203, filed on Dec. 20, 2017.

(51) Int. Cl.
| | | |
|---|---|---|
| *C11D 9/36* | (2006.01) | |
| *A61K 8/892* | (2006.01) | |
| *A61K 8/898* | (2006.01) | |
| *A61K 8/06* | (2006.01) | |
| *A61Q 5/02* | (2006.01) | |
| *A61Q 5/12* | (2006.01) | |
| *A61K 8/04* | (2006.01) | |

(52) U.S. Cl.
CPC ........... *A61K 8/892* (2013.01); *A61K 8/046* (2013.01); *A61K 8/06* (2013.01); *A61K 8/062* (2013.01); *A61K 8/898* (2013.01); *A61Q 5/02* (2013.01); *A61Q 5/12* (2013.01); *A61K 2800/21* (2013.01); *A61K 2800/262* (2013.01)

(58) Field of Classification Search
CPC ......... C11D 1/82; C11D 3/0094; C11D 3/162; C11D 3/3742; C11D 3/3927; C11D 9/36; C11D 17/0021; C11D 17/0095
See application file for complete search history.

(56) References Cited

U.S. PATENT DOCUMENTS

| | | |
|---|---|---|
| 2,879,231 A | 3/1959 | Marshall |
| 3,709,437 A | 1/1973 | Wright |
| 3,950,532 A | 4/1976 | Bouillon et al. |
| 3,959,160 A | 5/1976 | Horsler et al. |
| 4,309,119 A | 1/1982 | Wittersheim |
| 4,329,334 A | 5/1982 | Su et al. |
| 4,726,945 A | 2/1988 | Patel |
| 4,839,166 A | 6/1989 | Grollier et al. |
| 4,867,971 A | 9/1989 | Ryan et al. |
| 4,997,641 A | 3/1991 | Hartnett |
| 5,294,644 A | 3/1994 | Login et al. |
| 5,332,569 A | 7/1994 | Wood et al. |
| 5,364,031 A | 11/1994 | Taniguchi et al. |
| 5,374,421 A | 12/1994 | Tashiro |
| 5,417,965 A | 5/1995 | Janchitraponvej et al. |
| 5,439,682 A | 8/1995 | Wivell |
| 5,441,659 A | 8/1995 | Minor |
| 5,560,918 A | 10/1996 | Wivell |
| 5,578,298 A * | 11/1996 | Berthiaume ........... A61K 8/898 424/70.122 |
| 5,599,549 A | 2/1997 | Wivell |
| 5,635,469 A | 6/1997 | Fowler et al. |
| 5,747,436 A | 5/1998 | Patel et al. |
| 5,776,444 A | 7/1998 | Birtwistle et al. |
| 5,816,446 A | 10/1998 | Steindorf et al. |
| 5,830,440 A | 11/1998 | Sturla et al. |
| 5,853,618 A | 12/1998 | Barker |
| 5,902,225 A | 5/1999 | Monson |
| 5,980,877 A | 11/1999 | Baravetto |
| 5,985,939 A | 11/1999 | Minor |
| 6,015,780 A | 1/2000 | Llosas Bigorra et al. |
| 6,020,303 A | 2/2000 | Cripe et al. |
| 6,039,933 A | 3/2000 | Samain et al. |
| 6,046,152 A | 4/2000 | Vinson et al. |
| 6,060,443 A | 5/2000 | Cripe et al. |
| 6,087,309 A | 7/2000 | Vinson et al. |
| 6,110,451 A | 8/2000 | Matz et al. |
| 6,133,222 A | 10/2000 | Vinson et al. |
| 6,153,569 A * | 11/2000 | Halloran ................ A61K 8/068 424/70.12 |
| 6,162,834 A | 12/2000 | Sebillotte-Arnaud et al. |
| 6,231,844 B1 | 5/2001 | Nambu |
| 6,268,431 B1 | 7/2001 | Snyder et al. |
| 6,284,225 B1 | 9/2001 | Bhatt |
| 6,329,331 B1 | 12/2001 | Aronson et al. |
| 6,335,312 B1 | 1/2002 | Coffindaffer et al. |
| 6,423,305 B1 | 7/2002 | Cauwet-Martin et al. |

(Continued)

FOREIGN PATENT DOCUMENTS

| | | |
|---|---|---|
| CA | 2078375 A1 | 3/1994 |
| CN | 102697668 B | 8/2013 |

(Continued)

OTHER PUBLICATIONS

U.S. Appl. No. 16/170,516, filed Oct. 25, 2018, Chang et al.

(Continued)

*Primary Examiner* — Charles I Boyer
(74) *Attorney, Agent, or Firm* — Alexandra S. Anoff

(57) ABSTRACT

A clear shampoo composition containing a silicone emulsion and a detersive surfactant. The silicone emulsion contains one or more silicone polymers that can be a polyorganosiloxane compound containing one or more quaternary ammonium groups, silicone blocks comprising between about 99 and about 199 siloxane units on average, at least one polyalkylene oxide structural unit; and at least one terminal ester group.

18 Claims, 9 Drawing Sheets

(56) References Cited

U.S. PATENT DOCUMENTS

| | | |
|---|---|---|
| 6,451,300 B1 | 9/2002 | Dunlop et al. |
| 6,511,669 B1 | 1/2003 | Garnier et al. |
| 6,579,907 B1 | 6/2003 | Sebillotte-Arnaud et al. |
| 6,627,585 B1 | 9/2003 | Steer |
| 6,642,194 B2 | 11/2003 | Harrison |
| 6,649,155 B1 | 11/2003 | Dunlop et al. |
| 6,716,455 B2 | 4/2004 | Birkel |
| 6,743,760 B1 | 6/2004 | Hardy et al. |
| 6,827,795 B1 | 12/2004 | Scheper et al. |
| 6,897,253 B2 | 5/2005 | Schmucker-Castner |
| 6,930,078 B2 | 8/2005 | Wells |
| 6,992,054 B2 | 1/2006 | Lee et al. |
| 7,217,752 B2 | 5/2007 | Schmucker-Castner et al. |
| 7,220,408 B2 | 5/2007 | Decoster et al. |
| 7,223,385 B2 | 5/2007 | Gawtrey et al. |
| 7,485,289 B2 | 2/2009 | Gawtrey et al. |
| 7,504,094 B2 | 3/2009 | Decoster et al. |
| 7,531,497 B2 | 5/2009 | Midha et al. |
| 7,541,320 B2 | 6/2009 | Dabkowski et al. |
| 7,659,233 B2 | 2/2010 | Hurley et al. |
| 7,666,825 B2 | 2/2010 | Wagner et al. |
| 7,820,609 B2 | 10/2010 | Soffin et al. |
| 7,829,514 B2 | 11/2010 | Paul et al. |
| 7,928,053 B2 | 4/2011 | Hecht et al. |
| 7,977,288 B2 | 7/2011 | SenGupta |
| 8,084,407 B2 | 12/2011 | Soffin et al. |
| 8,088,721 B2 | 1/2012 | Soffin et al. |
| 8,119,168 B2 | 2/2012 | Johnson |
| 8,124,063 B2 | 2/2012 | Harichian et al. |
| 8,300,949 B2 | 10/2012 | Xu |
| 8,388,699 B2 | 3/2013 | Wood |
| 8,401,304 B2 | 3/2013 | Cavallaro et al. |
| 8,435,501 B2 | 5/2013 | Peffly et al. |
| 8,437,556 B1 | 5/2013 | Saisan |
| 8,580,725 B2 | 11/2013 | Kuhlman et al. |
| 8,609,600 B2 | 12/2013 | Warr et al. |
| 8,628,760 B2 | 1/2014 | Carter et al. |
| 8,653,014 B2 | 2/2014 | Hilvert |
| 8,675,919 B2 | 3/2014 | Maladen |
| 8,680,035 B2 | 3/2014 | Kuhlman et al. |
| 8,699,751 B2 | 4/2014 | Maladen |
| 8,709,385 B2 | 4/2014 | Tamarkin |
| 8,741,363 B2 | 6/2014 | Albrecht et al. |
| 8,771,765 B1 | 7/2014 | Fernandez |
| 8,795,635 B2 | 8/2014 | Tamarkin et al. |
| 8,883,698 B2 | 11/2014 | Scheibel et al. |
| 9,006,162 B1 | 4/2015 | Rizk |
| 9,186,642 B2 | 11/2015 | Dihora et al. |
| 9,265,727 B1 | 2/2016 | Lowenborg |
| 9,296,550 B2 | 3/2016 | Smith |
| 9,308,398 B2 | 4/2016 | Hutton et al. |
| 9,428,616 B2 | 8/2016 | Wagner |
| 9,512,275 B2 | 12/2016 | Wagner |
| 9,610,239 B2 | 4/2017 | Feng |
| 9,682,021 B2 | 6/2017 | Tamarkin et al. |
| 9,776,787 B2 | 10/2017 | Nakajima |
| 9,949,901 B2 | 4/2018 | Zhao |
| 9,968,535 B2 | 5/2018 | Kitko |
| 9,968,537 B2 | 5/2018 | Sharma |
| 9,993,419 B2 | 6/2018 | Glenn, Jr. |
| 9,993,420 B2 | 6/2018 | Glenn, Jr. et al. |
| 10,311,575 B2 | 6/2019 | Stofel |
| 10,426,713 B2 | 10/2019 | Song |
| 10,441,519 B2 | 10/2019 | Zhao |
| 10,653,590 B2 | 5/2020 | Torres Rivera |
| 10,799,434 B2 | 10/2020 | Torres Rivera |
| 10,842,720 B2 | 11/2020 | Thompson |
| 2001/0000467 A1 | 4/2001 | Murray |
| 2001/0006088 A1 | 7/2001 | Lyle |
| 2001/0006621 A1 | 7/2001 | Coupe et al. |
| 2001/0016565 A1 | 8/2001 | Bodet et al. |
| 2002/0028182 A1 | 3/2002 | Dawson |
| 2002/0037299 A1 | 3/2002 | Turowski-Wanke et al. |
| 2002/0172648 A1 | 11/2002 | Hehner et al. |
| 2002/0193265 A1 | 12/2002 | Perron et al. |
| 2002/0197213 A1 | 12/2002 | Schmenger et al. |
| 2003/0022799 A1 | 1/2003 | Alvarado et al. |
| 2003/0049292 A1 | 3/2003 | Turowski-Wanke et al. |
| 2003/0050150 A1 | 3/2003 | Tanaka |
| 2003/0059377 A1 | 3/2003 | Riley |
| 2003/0083210 A1 | 5/2003 | Goldberg |
| 2003/0108501 A1 | 6/2003 | Hofrichter |
| 2003/0147842 A1 | 8/2003 | Restle et al. |
| 2003/0154561 A1 | 8/2003 | Patel |
| 2003/0161802 A1 | 8/2003 | Flammer |
| 2003/0180246 A1 | 9/2003 | Frantz et al. |
| 2003/0185867 A1 | 10/2003 | Kerschner et al. |
| 2003/0223951 A1 | 12/2003 | Geary et al. |
| 2003/0228272 A1 | 12/2003 | Amjad et al. |
| 2004/0014879 A1 | 1/2004 | Denzer et al. |
| 2004/0144863 A1 | 7/2004 | Kendrick |
| 2004/0229963 A1 | 11/2004 | Stephane |
| 2004/0235689 A1 | 11/2004 | Sakai et al. |
| 2005/0020468 A1 | 1/2005 | Frantz et al. |
| 2005/0136011 A1 | 6/2005 | Nekludoff |
| 2005/0152863 A1 | 7/2005 | Brautigam |
| 2005/0233929 A1 | 10/2005 | Queen |
| 2006/0002880 A1 | 1/2006 | Peffly |
| 2006/0030509 A1 | 2/2006 | Modi |
| 2006/0057075 A1 | 3/2006 | Arkin et al. |
| 2006/0057097 A1 | 3/2006 | Derici |
| 2006/0079417 A1 | 4/2006 | Wagner |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0090777 A1 | 5/2006 | Hecht et al. |
| 2006/0120982 A1 | 6/2006 | Derici et al. |
| 2006/0120988 A1 | 6/2006 | Bailey et al. |
| 2006/0135397 A1 | 6/2006 | Bissey-Beugras |
| 2006/0183662 A1 | 8/2006 | Crotty et al. |
| 2006/0210139 A1 | 9/2006 | Carroll |
| 2006/0229227 A1 | 10/2006 | Goldman |
| 2006/0252662 A1 | 11/2006 | Soffin |
| 2006/0276357 A1 | 12/2006 | Smith, III et al. |
| 2006/0292104 A1 | 12/2006 | Guskey |
| 2007/0072781 A1 | 3/2007 | Soffin et al. |
| 2007/0110700 A1 | 5/2007 | Wells |
| 2007/0154402 A1 | 7/2007 | Trumbore et al. |
| 2007/0155637 A1 | 7/2007 | Smith, III et al. |
| 2007/0160555 A1 | 7/2007 | Staudigel |
| 2007/0179207 A1 | 8/2007 | Fernandez de Castro et al. |
| 2007/0269397 A1 | 11/2007 | Terada |
| 2007/0292380 A1 | 12/2007 | Staudigel |
| 2008/0008668 A1 | 1/2008 | Harichian et al. |
| 2008/0019928 A1 | 1/2008 | Franzke |
| 2008/0063618 A1 | 3/2008 | Johnson |
| 2008/0138442 A1 | 6/2008 | Johnson |
| 2008/0152610 A1 | 6/2008 | Cajan |
| 2008/0206179 A1 | 8/2008 | Peffly et al. |
| 2008/0260655 A1 | 10/2008 | Tamarkin et al. |
| 2008/0261844 A1 | 10/2008 | Ruppert et al. |
| 2008/0317698 A1 | 12/2008 | Wells et al. |
| 2009/0029900 A1 | 1/2009 | Cetti et al. |
| 2009/0041702 A1 | 2/2009 | Molenda |
| 2009/0062406 A1 | 3/2009 | Loeffler |
| 2009/0155383 A1 | 6/2009 | Kitko et al. |
| 2009/0178210 A1 | 7/2009 | Bistram |
| 2009/0197784 A1 | 8/2009 | Ainger |
| 2009/0221463 A1 | 9/2009 | Kitko et al. |
| 2009/0246236 A1 | 10/2009 | Kitko |
| 2009/0312224 A1 | 12/2009 | Yang et al. |
| 2009/0324505 A1 | 12/2009 | Seidling |
| 2010/0183539 A1 | 7/2010 | Bernhardt |
| 2010/0310644 A1 | 12/2010 | Liebmann |
| 2011/0008267 A1 | 1/2011 | Arkin et al. |
| 2011/0165107 A1 | 7/2011 | Derks et al. |
| 2011/0171155 A1 | 7/2011 | Federle |
| 2011/0232668 A1 | 9/2011 | Hoffmann et al. |
| 2011/0268778 A1 | 11/2011 | Dihora |
| 2011/0269657 A1 | 11/2011 | Dihora et al. |
| 2011/0305739 A1 | 12/2011 | Royce |
| 2011/0319790 A1 | 12/2011 | Kost et al. |
| 2012/0014901 A1 | 1/2012 | Sunkel et al. |

(56) References Cited

U.S. PATENT DOCUMENTS

| | | |
|---|---|---|
| 2012/0031419 A1 | 2/2012 | Batt |
| 2012/0034173 A1 | 2/2012 | Batt |
| 2012/0100091 A1 | 4/2012 | Hata et al. |
| 2012/0100092 A1 | 4/2012 | Murray |
| 2012/0291911 A1 | 11/2012 | Smith |
| 2012/0309660 A1 | 12/2012 | Kawasoe |
| 2012/0316095 A1 | 12/2012 | Wei et al. |
| 2013/0053295 A1 | 2/2013 | Kinoshita et al. |
| 2013/0053300 A1 | 2/2013 | Scheibel et al. |
| 2013/0089587 A1 | 4/2013 | Staudigel |
| 2013/0115173 A1 | 5/2013 | Trumbore et al. |
| 2013/0143784 A1 | 6/2013 | Rizk |
| 2013/0150338 A1 | 6/2013 | Ananthapadmanabhan |
| 2013/0156712 A1 | 6/2013 | Frantz |
| 2013/0189212 A1 | 7/2013 | Jawale et al. |
| 2013/0243718 A1 | 9/2013 | Pasquet |
| 2013/0244922 A1 | 9/2013 | Bartelt |
| 2013/0280192 A1 | 10/2013 | Carter et al. |
| 2013/0280202 A1 | 10/2013 | Stella et al. |
| 2013/0284195 A1 | 10/2013 | Murdock |
| 2013/0296289 A1 | 11/2013 | Hall et al. |
| 2014/0037703 A1 | 2/2014 | Dihora et al. |
| 2014/0039066 A1 | 2/2014 | Grimadell et al. |
| 2014/0127149 A1 | 5/2014 | Lepilleur |
| 2014/0131395 A1 | 5/2014 | Chang |
| 2014/0134125 A1* | 5/2014 | Dahl ............... A61K 8/068 424/70.121 |
| 2014/0162979 A1 | 6/2014 | Palla-Venkata |
| 2014/0171471 A1 | 6/2014 | Krueger |
| 2014/0216495 A1 | 8/2014 | Bureiko |
| 2014/0228268 A1 | 8/2014 | Fahl et al. |
| 2014/0237732 A1 | 8/2014 | Zuedel Fernandes et al. |
| 2014/0308227 A1 | 10/2014 | Mabille |
| 2014/0309154 A1 | 10/2014 | Carter et al. |
| 2014/0335041 A1 | 11/2014 | Peffly et al. |
| 2014/0348884 A1 | 11/2014 | Hilvert et al. |
| 2014/0348886 A1 | 11/2014 | Johnson et al. |
| 2015/0021496 A1 | 1/2015 | Shabbir |
| 2015/0037273 A1* | 2/2015 | Wagner ............ D06M 15/643 424/70.122 |
| 2015/0050231 A1 | 2/2015 | Murase |
| 2015/0093420 A1 | 4/2015 | Snyder |
| 2015/0098921 A1 | 4/2015 | Franzke et al. |
| 2015/0099684 A1 | 4/2015 | Boutique |
| 2015/0110728 A1 | 4/2015 | Jayaswal |
| 2015/0147286 A1 | 5/2015 | Barrera |
| 2015/0218496 A1 | 8/2015 | Schmiedel et al. |
| 2015/0297489 A1 | 10/2015 | Kleinen |
| 2015/0313818 A1 | 11/2015 | Stagg |
| 2015/0359725 A1 | 12/2015 | Glenn, Jr. et al. |
| 2016/0008257 A1 | 1/2016 | Zhou et al. |
| 2016/0022566 A1 | 1/2016 | Figura |
| 2016/0113849 A1 | 4/2016 | Grimadell et al. |
| 2016/0128944 A1 | 5/2016 | Chawrai |
| 2016/0193125 A1 | 7/2016 | Jones et al. |
| 2016/0279048 A1 | 9/2016 | Jayaswal et al. |
| 2016/0287503 A1 | 10/2016 | Schroeder |
| 2016/0287509 A1 | 10/2016 | Peffly |
| 2016/0303043 A1 | 10/2016 | Khoury |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao |
| 2016/0310375 A1 | 10/2016 | Torres Rivera |
| 2016/0310386 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310393 A1 | 10/2016 | Chang et al. |
| 2016/0310402 A1 | 10/2016 | Zhao et al. |
| 2016/0317424 A1 | 11/2016 | Kadir |
| 2016/0354300 A1 | 12/2016 | Thompson et al. |
| 2017/0071837 A1 | 3/2017 | Schelges et al. |
| 2017/0101609 A1 | 4/2017 | Vargas |
| 2017/0165164 A1 | 6/2017 | Zhao et al. |
| 2017/0165165 A1 | 6/2017 | Zhao et al. |
| 2017/0209359 A1 | 7/2017 | Zhao et al. |
| 2017/0252273 A1 | 9/2017 | Renock et al. |
| 2017/0278249 A1 | 9/2017 | Stofel et al. |
| 2017/0283959 A1 | 10/2017 | Shellef |
| 2017/0304172 A1 | 10/2017 | Chang et al. |
| 2017/0304184 A1 | 10/2017 | Glenn, Jr. |
| 2017/0304185 A1 | 10/2017 | Glenn, Jr. et al. |
| 2017/0304186 A1 | 10/2017 | Glenn, Jr. |
| 2017/0333321 A1 | 11/2017 | Carnali |
| 2018/0044097 A1 | 2/2018 | Zeik |
| 2018/0057451 A1 | 3/2018 | Owens et al. |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson et al. |
| 2018/0110704 A1 | 4/2018 | Zhao et al. |
| 2018/0110707 A1 | 4/2018 | Zhao et al. |
| 2018/0110710 A1 | 4/2018 | Zhao et al. |
| 2018/0110714 A1 | 4/2018 | Glenn, Jr. et al. |
| 2018/0116937 A1 | 5/2018 | Park et al. |
| 2018/0116941 A1 | 5/2018 | Wang |
| 2018/0221266 A1 | 8/2018 | Zhao et al. |
| 2018/0256481 A1 | 9/2018 | Glenn, Jr. |
| 2018/0311135 A1 | 11/2018 | Chang |
| 2018/0311136 A1 | 11/2018 | Chang |
| 2018/0318194 A1 | 11/2018 | Hoffmann et al. |
| 2018/0344611 A1 | 12/2018 | Zhao et al. |
| 2018/0344612 A1 | 12/2018 | Zhao et al. |
| 2018/0344613 A1 | 12/2018 | Zhao et al. |
| 2018/0344614 A1 | 12/2018 | Zhao et al. |
| 2019/0105242 A1 | 4/2019 | Song |
| 2019/0105243 A1 | 4/2019 | Song |
| 2019/0105244 A1 | 4/2019 | Song |
| 2019/0105245 A1 | 4/2019 | Song |
| 2019/0105246 A1 | 4/2019 | Cochran |
| 2019/0105247 A1 | 4/2019 | Song |
| 2019/0117543 A1 | 4/2019 | Zhao |
| 2019/0117544 A1 | 4/2019 | Zhao |
| 2019/0117545 A1 | 4/2019 | Zhao |
| 2019/0142711 A1 | 5/2019 | Torres Rivera |
| 2019/0183778 A1 | 6/2019 | Glenn, Jr. |
| 2019/0192405 A1 | 6/2019 | Zhao |
| 2019/0240121 A1 | 8/2019 | Torres Rivera |
| 2019/0307298 A1 | 10/2019 | Zhao |
| 2019/0365633 A1 | 12/2019 | Glenn, Jr. |
| 2020/0000690 A1 | 1/2020 | Renock |
| 2020/0129402 A1 | 4/2020 | Jamadagni |
| 2020/0163846 A1 | 5/2020 | Song |
| 2020/0237628 A1 | 7/2020 | Torres Rivera |

FOREIGN PATENT DOCUMENTS

| | | |
|---|---|---|
| CN | 102697670 B | 7/2014 |
| CN | 102851015 B | 12/2014 |
| CN | 105769617 A | 7/2016 |
| DE | 4315396 A1 | 11/1994 |
| DE | 202005009618 U1 | 9/2005 |
| EP | 0574086 A2 | 12/1993 |
| EP | 1340485 A2 | 2/2003 |
| EP | 1346720 A2 | 9/2003 |
| EP | 1714678 A1 | 10/2006 |
| EP | 2042216 B1 | 9/2015 |
| JP | 356011009 A | 12/1981 |
| JP | 358113300 | 7/1983 |
| JP | H08310924 A | 11/1996 |
| JP | 2964226 B2 | 10/1999 |
| JP | 3069802 B2 | 7/2000 |
| JP | 2003201217 A | 12/2001 |
| JP | 2002226889 A | 8/2002 |
| JP | 3480165 B2 | 12/2003 |
| JP | 3634988 B2 | 3/2005 |
| JP | 3634991 B2 | 3/2005 |
| JP | 3634996 B2 | 3/2005 |

(56) References Cited

FOREIGN PATENT DOCUMENTS

| | | |
|---|---|---|
| JP | 2005187359 A | 7/2005 |
| JP | 2008214292 A | 9/2008 |
| JP | 5041113 B2 | 7/2012 |
| JP | 5046394 B2 | 1/2014 |
| JP | 5667790 B2 | 2/2015 |
| KR | 1020080111280 | 12/2008 |
| KR | 20140060882 A | 5/2014 |
| WO | WO199325650 A1 | 12/1993 |
| WO | WO9502389 A1 | 1/1995 |
| WO | WO9726854 A1 | 7/1997 |
| WO | WO9823258 A1 | 6/1998 |
| WO | WO9918928 A1 | 4/1999 |
| WO | WO9924004 A1 | 5/1999 |
| WO | D012553 A1 | 3/2000 |
| WO | WO0142409 A1 | 6/2001 |
| WO | WO0148021 A1 | 7/2001 |
| WO | WO2005023975 A1 | 3/2005 |
| WO | WO2009016555 A1 | 2/2009 |
| WO | 2009053931 A2 | 4/2009 |
| WO | WO2010052147 A2 | 5/2010 |
| WO | WO2012055587 A1 | 5/2012 |
| WO | WO2012084970 A1 | 6/2012 |
| WO | WO2013010706 A1 | 1/2013 |
| WO | WO2014148245 A1 | 9/2014 |
| WO | WO2016147196 A1 | 9/2016 |
| WO | 2017052161 A1 | 3/2017 |
| WO | 2017140798 A1 | 8/2017 |
| WO | WO2017207685 A1 | 12/2017 |
| WO | WO2018023180 A1 | 2/2018 |

OTHER PUBLICATIONS

U.S. Appl. No. 16/170,711, filed Oct. 25, 2018, Jamadagni et al.
U.S. Appl. No. 16/248,900, filed Jan. 16, 2019, Torres Rivera et al.
U.S. Appl. No. 16/285,535, filed Feb. 26, 2019, Zhao et al.
U.S. Appl. No. 16/226,927, filed Dec. 20, 2018, Glenn, Jr. et al.
U.S. Appl. No. 16/376,033, filed Apr. 5, 2019, Zhao et al.
U.S. Appl. No. 16/390,270, filed Apr. 22, 2019, Torres Rivera et al.
"Natural Detangling Shampoo", Mintel Database, Sep. 13, 2017.
"Soda Shampoo", Mintel Database, Apr. 2015.
"Treatment Foam for Recurrent Scaling Conditions", Mintel Database, Aug. 2007.
All Final and Non-Final Office Actions for U.S. Appl. No. 16/156,045.
All Final and Non-Final Office Actions for U.S. Appl. No. 15/135,657.
All Final and Non-Final Office Actions for U.S. Appl. No. 15/135,663.
All Final and Non-Final Office Actions for U.S. Appl. No. 15/135,677.
All Final and Non-Final Office Actions for U.S. Appl. No. 15/135,701.
All Final and Non-Final Office Actions for U.S. Appl. No. 15/135,998.
All Final and Non-Final Office Actions for U.S. Appl. No. 15/145,696.
All Final and Non-Final Office Actions for U.S. Appl. No. 15/2788,938.
All Final and Non-Final Office Actions for U.S. Appl. No. 15/299,860.
All final and non-final office actions for U.S. Appl. No. 15/379,660.
All final and non-final office actions for U.S. Appl. No. 15/379,674.
All final and non-final office actions for U.S. Appl. No. 15/448,911.
All final and non-final office actions for U.S. Appl. No. 15/467,317.
All Final and Non-Final Office Actions for U.S. Appl. No. 15/481,777.
All Final and Non-Final Office Actions for U.S. Appl. No. 15/788,895.
All Final and Non-Final Office Actions for U.S. Appl. No. 15/788,949.
All Final and Non-Final Office Actions for U.S. Appl. No. 15/788,998.
All Final and Non-Final Office Actions for U.S. Appl. No. 15/789,010.
All Final and Non-Final Office Actions for U.S. Appl. No. 15/789,020.
All Final and Non-Final Office Actions for U.S. Appl. No. 15/789,030.
All Final and Non-Final Office Actions for U.S. Appl. No. 15/789,038.
All Final and Non-Final Office Actions for U.S. Appl. No. 15/789,044.
All Final and Non-Final Office Actions for U.S. Appl. No. 15/789,081.
All Final and Non-Final Office Actions for U.S. Appl. No. 15/789,172.
All Final and Non-Final Office Actions for U.S. Appl. No. 15/789,188.
All Final and Non-Final Office Actions for U.S. Appl. No. 15/789,208.
All Final and Non-final Office Actions for U.S. Appl. No. 15/923,499.
All final and non-final office actions for U.S. Appl. No. 15/962,327.
All final and non-final office actions for U.S. Appl. No. 15/962,351.
All final and non-final office actions for U.S. Appl. No. 16/001,045.
All final and non-final office actions for U.S. Appl. No. 16/001,053.
All final and non-final office actions for U.S. Appl. No. 16/001,058.
All final and non-final office actions for U.S. Appl. No. 16/001,064.
All Final and Non-Final Office Actions for U.S. Appl. No. 16/156,015.
All Final and Non-Final Office Actions for U.S. Appl. No. 16/156,038.
All Final and Non-Final Office Actions for U.S. Appl. No. 16/156,053.
All Final and Non-Final Office Actions for U.S. Appl. No. 16/156,066.
All Final and Non-Final Office Actions for U.S. Appl. No. 16/156,072.
All final and non-final office actions for U.S. Appl. No. 16/165,016.
All final and non-final office actions for U.S. Appl. No. 16/165,033.
All final and non-final office actions for U.S. Appl. No. 16/165,044.
All final and non-final office actions for U.S. Appl. No. 16/170,498.
All final and non-final office actions for U.S. Appl. No. 16/170,516.
All final and non-final office actions for U.S. Appl. No. 16/170,711.
All final and non-final office actions for U.S. Appl. No. 16/226,927.
All final and non-final office actions for U.S. Appl. No. 16/248,900.
All final and non-final office actions for U.S. Appl. No. 16/285,535.
All final and non-final office actions for U.S. Appl. No. 16/376,033.
All final and non-final office actions for U.S. Appl. No. 16/390,270.
Anonymous: "Merquat Polyquaternium 47 Series, Water Soluble Polymers for Personal Care", Jul. 30, 2017, URL: https://www.in-cosmetics.com/_novadocuments/2729, retrieved on Dec. 21, 2018.
Carbopol Aqua SF-1 Polymer Technical Data Sheet, TDS-294, Dec. 2000.
Christensen et al., "Experimental Determination of Bubble Size Distribution in a Water Column by Interferometric Particle Imaging and Telecentric Direct Image Method", Student Report, Aalborg University, Jun. 3, 2014.
Dehyquart Guar: Published Nov. 2010.
Hair Care/Conditioning Polymers Differentiation, Anonymous, Feb. 1, 2017, URL: http://www.biochim.it./assets/site/media/allegati/cosmetica/hair-care/tab-merquat-hair-care.pdf, retrieved on Dec. 20, 2018, p. 1.
PCT International Search Report and Written Opinion for PCT/US2016/028728 dated Aug. 5, 2016.
PCT International Search Report and Written Opinion for PCT/US2016/028729 dated Jun. 15, 2016.
PCT International Search Report and Written Opinion for PCT/US2016/028730 dated Aug. 5, 2016.
PCT International Search Report and Written Opinion for PCT/US2016/028735 dated Jul. 25, 2016.
PCT International Search Report and Written Opinion for PCT/US2016/028736 dated Jul. 25, 2016.
PCT International Search Report and Written Opinion for PCT/US2016/028742 dated Jul. 18, 2016.
PCT International Search Report and Written Opinion for PCT/US2016/058123 dated Dec. 21, 2016.
PCT International Search Report and Written Opinion for PCT/US2016/066752 dated Feb. 22, 2017.
PCT International Search Report and Written Opinion for PCT/US2016/066757 dated Feb. 22, 2017.
PCT International Search Report and Written Opinion for PCT/US2017/020604 dated May 11, 2017.
PCT International Search Report and Written Opinion for PCT/US2017/022737 dated Jun. 22, 2017.
PCT International Search Report and Written Opinion for PCT/US2017/057486 dated Jan. 9, 2018.
PCT International Search Report and Written Opinion for PCT/US2017/057487 dated Dec. 19, 2017.
PCT International Search Report and Written Opinion for PCT/US2017/057488 dated Dec. 12, 2017.
PCT International Search Report and Written Opinion for PCT/US2017/057497 dated Jan. 8, 2018.
PCT International Search Report and Written Opinion for PCT/US2017/057503 dated Dec. 13, 2017.
PCT International Search Report and Written Opinion for PCT/US2017/057507 dated Dec. 13, 2017.
PCT International Search Report and Written Opinion for PCT/US2017/057510 dated Jan. 11, 2018.
PCT International Search Report and Written Opinion for PCT/US2017/057511 dated Feb. 2, 2018.

(56) References Cited

OTHER PUBLICATIONS

PCT International Search Report and Written Opinion for PCT/US2017/057514 dated Jan. 10, 2018.
PCT International Search Report and Written Opinion for PCT/US2017/057515 dated Dec. 11, 2017.
PCT International Search Report and Written Opinion for PCT/US2017/057522 dated Feb. 2, 2018.
PCT International Search Report and Written Opinion for PCT/US2017/057533 dated Jan. 8, 2018.
PCT International Search Report and Written Opinion for PCT/US2017/057541 dated Dec. 22, 2017.
PCT International Search Report and Written Opinion for PCT/US2018/029313 dated Jul. 11, 2018.
PCT International Search Report and Written Opinion for PCT/US2018/029315 dated Jun. 27, 2018.
PCT International Search Report and Written Opinion for PCT/US2018/036181 dated Aug. 3, 2018.
PCT International Search Report and Written Opinion for PCT/US2018/036185 dated Aug. 3, 2018.
PCT International Search Report and Written Opinion for PCT/US2018/055102 dated Jan. 9, 2019.
PCT International Search Report and Written Opinion for PCT/US2018/055103 dated Jan. 9, 2019.
PCT International Search Report and Written Opinion for PCT/US2018/055104 dated Jan. 18, 2019.
PCT International Search Report and Written Opinion for PCT/US2018/055105 dated Jan. 8, 2019.
PCT International Search Report and Written Opinion for PCT/US2018/055106 dated Jan. 16, 2019.
PCT International Search Report and Written Opinion for PCT/US2018/055107 dated Jan. 28, 2019.
PCT International Search Report and Written Opinion for PCT/US2018/056669 dated Jan. 31, 2019.
PCT International Search Report and Written Opinion for PCT/US2018/056673 dated Feb. 5, 2019.
PCT International Search Report and Written Opinion for PCT/US2018/056674 dated Feb. 5, 2019.
PCT International Search Report and Written Opinion for PCT/US2018/057451 dated Feb. 25, 2019.
PCT International Search Report and Written Opinion for PCT/US2018/057476 dated Jan. 18, 2019.
PCT International Search Report and Written Opinion for PCT/US2018/066697 dated Mar. 15, 2019.
PCT International Search Report and Written Opinion for PCT/US2018/066701 dated Mar. 15, 2019.
Polyquaternium: "Final Report on the Safety Assessment of the Polyguatemium-10", Journal of the American College of Toxicology, Jan. 1, 1988, URL: http://www.beauty-review.nl/wp-content/uploads/2015/02/Final-Report-on-theSafety-Assessment-of-Polyguaternium-10.pdf, retrieved on Dec. 20, 2018.
Practical Modern Hair Science, Published 2012.
S. Herrwerth et al.: "Highly Concentrated Cocamidopropyl Betaine—The Latest Developments for Improved Sustainability and Enhanced Skin Care", Tenside, Surfactants, Detergents, vol. 45, No. 6, Nov. 1, 2008, pp. 304-308, p. 305—left-hand column.
"Deep Image Matting", Ning Xu et al, Beckman Institute for Advanced Science and Technology, University of Illinois at Urbana-Champaign, Adobe Research, Mar. 10, 2017.
All final and non-final office actions for U.S. Appl. No. 16/532,556 (P&G Case 14973C), See Pair.
All final and non-final office actions for U.S. Appl. No. 16/846,594 (P&G Case 14550MC), See Pair.
All final and non-final office actions for U.S. Appl. No. 17/071,033 (P&G Case 15069MC), See Pair.
D'Souza et al., Shampoo and Conditioners: What a Dermatologist Should Know? Indian J Dermatol, 2015 May-Jun. 50(3), 248-254 (2015).
Fevola, Michael J. "Guar Hydroxypropyltrimonium Chloride." Cosmetics and toiletries 127.1 (2012) 16-21.
Inspection certificate for Hostapon® CCG, Clariant lberica Production, SA., May 6, 2019.
Medvedev, Diffusion Coefficients in Multicomponent Mixtures, PhD Thesis from Technical University of Denmark, 2005, 181 pages.
Musazzi, "Emulsion versus nonoemulsion: how much is the formulative shift critical for a cosmetic product?" (Drug Deliv and Trans. Res. (2018) 8:414-421 (Year: 2018).
PCT International Search Report and Written Opinion for PCT/US2019/025923 dated Jun. 24, 2019.
PCT International Search Report and Written Opinion for PCT/US2019/057974 dated Feb. 3, 2020.
Perm Inc Diffusion Coefficient: Measurement Techiques, https://perminc.com/resourcesffundamentals-of-fluid-flow-In-porous-media/chapter-3-molecular-diffusion/diffusion-coefficient/measurement-techniques, Oct. 2020_.
Product Bulletin, Amphosol® CG, Cocamidopropyl Betaine, Stepan Company, Jun. 2011.
Product Data Sheet for Chemoryrm Ls Surfactant, Sodium Lauroyl Sarcosinate, Lubrizol Advanced Materials, Inc., Mar. 24, 2020.
Product Data Sheet, Eversonrm UCS-405, Disodium Cocoyl Glutamate (Sodium Cocoyl Glutamate*), Sino Lion USA, Jul. 2018.
Product Fact Sheet - Hostapon® Ccg, mild anionic surfactant for the cosmetic industry, Clariant International Ltd., Aug. 2014.
Product Fact Sheet, Hostapon® CGN, Mild anionic surfactant for the cosmetic industry, Clariant International Ltd., Jan. 2016.
Robinson et al., Final Report of the Amended Safety Assessment of Sodium Laureth Sulfate and Related Salts of SulfatedEthoxylated Alcohols, International Journal of Toxicology 29(Supplement 3) 151S-161S, 2010 (Year 2010).
Schaefer, Katie, "Eco-friendly, Non-flammable Liquified Gas Propellant", https://www.cosmeticsandtoiletries.com/ formulating/function/aids/138418589.html#close-olyticsmodal. Published Jan. 30, 2012.
UL Prospector® Product Data Sheet, Plantacare® 818 UP, C8-16 fatty alcohol glucoside, BASF, May 21, 2015.
U.S. Appl. No. 17/071,033, dated Oct. 15, 2020, Glenn, Jr. et al.

\* cited by examiner

CLEAR SHAMPOO COMPOSITION CONTAINING SILICONE POLYMERS

FIELD OF THE INVENTION

The invention relates to a clear shampoo composition that comprises one or more silicone polymers. The silicone polymer is a polyorganosiloxane compound containing one or more quaternary ammonium groups, silicone blocks comprising between about 99 and about 199 siloxane units on average, at least one polyalkylene oxide structural unit; and at least one terminal ester group.

BACKGROUND OF THE INVENTION

Many consumers want a clear shampoo that provides deep cleaning to remove styling product residue, pollutants, and oil leaving their hair fresh, glossy, and full of volume. However, consumers often complain that clear shampoos feel like they strip the hair, which can make the hair feel like straw and have poor wet and dry feel (i.e. the hair feels rough, tangled, and difficult to comb when it is wet and dry).

One way to improve the wet and dry feel is to add silicone to the shampoo. However, many silicones that provide good wet feel are relatively large and are visible in a clear shampoo, making the shampoo appear hazy or creamy, instead of clear. Yet smaller silicones generally do not provide consumer acceptable wet and dry feel. Furthermore, some silicones that are used in hair care products can leave the hair feeling slippery and oily instead of fresh and clean, which is generally not preferred by consumers who seek a clear shampoo.

Therefore, there is a need for a clear shampoo composition that contains a silicone polymer where the composition provides consumer acceptable wet and dry feel.

SUMMARY OF THE INVENTION

A clear shampoo composition comprising: (a) a silicone emulsion comprising: (i) an emulsifier; (ii) from about 0.1% to about 10% of one or more silicones, by weight of the composition, wherein the average particle size of the one or more silicones is from about 1 nm to about 100 nm, and wherein at least one of the silicone is a polyorganosiloxane compound comprising: (1) one or more quaternary ammonium groups; (2) silicone blocks comprising between about 99 and about 199 siloxane units on average; (3) at least one polyalkylene oxide structural unit; and (4) at least one terminal ester group; (b) from about 4% to about 45%, by weight, of a detersive surfactant; wherein the shampoo composition is clear.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1A:
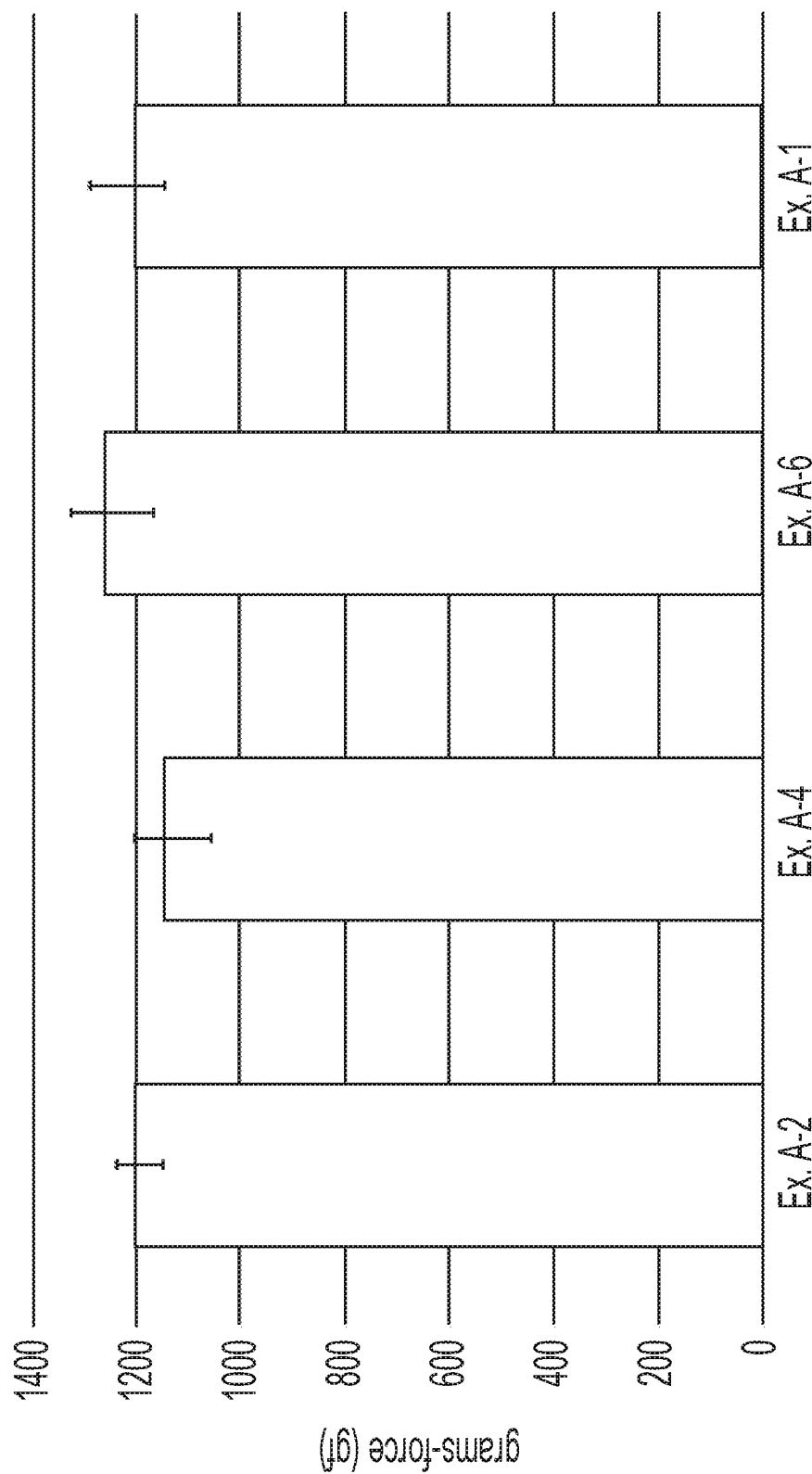
FIG. 1A compares the final rinse friction of Examples A-1, A-2, A-4, and A-6.

While the specification concludes with claims particularly pointing out and distinctly claiming the invention, it is believed that the present disclosure will be better understood from the following description.

As used herein, the articles including "a" and "an" when used in a claim, are understood to mean one or more of what is claimed or described.

As used herein, "comprising" means that other steps and other ingredients which do not affect the end result can be added. This term encompasses the terms "consisting of" and "consisting essentially of."

As used herein, "mixtures" is meant to include a simple combination of materials and any compounds that may result from their combination.

As used herein, "molecular weight" or "M.Wt." refers to the weight average molecular weight unless otherwise stated. Molecular weight is measured using industry standard method, gel permeation chromatography ("GPC").

As used herein, "substantially free" means less than 3%, alternatively less than 2%, alternatively less than 1%, alternatively less than 0.5%, alternatively less than 0.25%, alternatively less than 0.1%, alternatively less than 0.05%, alternatively less than 0.01%, alternatively less than 0.001%, and/or alternatively free of. As used herein, "free of" means 0%.

As used herein, the terms "include," "includes," and "including," are meant to be non-limiting and are understood to mean "comprise," "comprises," and "comprising," respectively.

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Where amount ranges are given, these are to be understood as being the total amount of said ingredient in the composition, or where more than one species fall within the scope of the ingredient definition, the total amount of all ingredients fitting that definition, in the composition. For example, if the composition comprises from 1% to 5% fatty alcohol, then a composition comprising 2% stearyl alcohol and 1% cetyl alcohol and no other fatty alcohol, would fall within this scope.

The amount of each particular ingredient or mixtures thereof described hereinafter can account for up to 100% (or 100%) of the total amount of the ingredient(s) in the shampoo composition.

Shampoo Composition

Many consumers want a clear shampoo that provides deep cleaning and leaves the hair fresh, conditioned, and full of volume. Silicones are often added to shampoo to improve conditioning. However, some silicones are visible in clear shampoos the composition may appear hazy or creamy and/or consumers may perceive that their hair is slick and weighed down.

The shampoo can provide consumer acceptable wet conditioning and dry conditioning (i.e. parity or better wet and/or dry conditioning), while reducing the total level of actual silicone deposition as compared to shampoo compositions with current, marketed silicone emulsions (DC 1872, available from Dow Corning® and Belsil DM5500, available from Wacker®). This indicates that the clear shampoo composition could break the tradeoff normally associated with conditioning shampoo compositions, the shampoo composition can provide acceptable conditioning without the buildup of the silicone. Furthermore, the clear shampoo composition can leave the hair feeling clean without feeling stripped.

The shampoo composition can be visually clear. The shampoo can have a % Transmittance of greater than or equal to 80% and/or from about 80% to about 100%, as determined by the % Transmittance Test Method, described hereafter. In another example, the shampoo composition can be transparent and have a % transmittance greater than 30% and less than 80%. In another example, the silicone emulsion can be visually clear.

The shampoo composition can leave a general population hair switch with a final rinse friction from about 1000 gf to about 1600 gf, alternatively from about 1100 gf to about 1500 gf, and alternatively from about 1200 gf to about 1400 gf, as determined by the Hair Wet Feel Friction Measurement Test Method, described hereafter.

The shampoo compositions can leave a general population hair switch with a mean Coarse Stroke 1 from about 50 gf to about 300 gf, alternatively from about 60 gf to about 250 gf, alternatively from about 75 gf to about 200 gf, and alternatively from about 100 gf to about 150 gf, as determined by the Hair Wet Combing Test Method, described hereafter.

The shampoo compositions can leave a general population hair switch with a mean dry feel (Inter Fiber Friction (IFF)) of from about 1000 gf to about 1600 gf, alternatively from about 1100 gf to about 1550 gf, alternatively from about 1200 gf to about 1500 gf, and alternatively from about 1250 gf to about 1400 gf, as determined by the Dry Feel Test Method, described hereafter.

The shampoo composition can leave a general population hair switch with a mean silicone deposition less than 250 ppm, less than 200 ppm, alternatively less than 150 ppm, alternatively less than 100 ppm, alternatively less 90 ppm, alternatively less than 75 ppm, and alternatively less than 60 ppm. The shampoo composition can leave general population hair with a silicone deposition from about 25 ppm to about 200 ppm, alternatively from about 30 ppm to about 175 ppm, alternatively from about 35 ppm to about 150 ppm, and alternatively from about 40 ppm to about 125 ppm. The silicone deposition can be determined by the Silicone Deposition Test Method, as described hereafter.

The shampoo composition may have a liquid phase viscosity of less than 8000 centipoise (cP) (8000 mPa·s), alternatively less than 5000 cP (5000 mPa·s), alternatively less than 4000 cP (4000 mPa·s), alternatively less than 3000 cP (3000 mPa·s), alternatively less than 2500 cP (2500 mPa·s). The shampoo composition may have a liquid phase viscosity of from about 1 cP (1 mPa·s) to about 8000 cP (8000 mPa·s), alternatively from about 10 cP (10 mPa·s) to about 6000 cP (6000 mPa·s), alternatively from about 25 cP (25 mPa·s) to about 5000 cP (5000 mPa·s), alternatively from about 40 cP (40 mPa·s) to about 3000 cP (3000 mPa·s), and/or alternatively from about 50 cP (50 mPa·s) to about 3000 cP (3000 mPa·s). The shampoo composition may have a liquid phase viscosity of from about 1 cP (1 mPa·s) to about 15,000 cP (15,000 mPa·s), alternatively from about 10 cP (10 mPa·s) to about 12,000 cP (12,000 mPa·s), alternatively from about 20 cP (20 mPa·s) to about 10,000 cP (10,000 mPa·s), alternatively from about 50 cP (50 mPa·s) to about 8,000 cP (8,000 mPa·s), alternatively from about 100 cP (100 mPa·s) to about 5000 cP (5000 mPa·s), alternatively from about 250 cP (25 mPa·s) to about 3000 cP (3000 mPa·s), and/or alternatively from about 500 cP (500 mPa·s) to about 2500 cP (2500 mPa·s).

Silicones

The shampoo composition may comprise from about 0.1% to about 16%, alternatively about 0.3% to about 12%, alternatively about 0.4% to about 10%, alternatively about 0.5% to about 8%, alternatively from about 1% to about 7%, alternatively from about 2% to about 6%, alternatively from about 1% to about 5%, and alternatively from about 2% to about 4% of one or more silicones, by weight of the shampoo composition. The shampoo composition may comprise from about 5% to about 16%, alternatively from about 6% to about 14%, and alternatively from about 7% to about 12% of one or more silicones, by weight of the composition. The shampoo composition may comprise from about 0.1% to about 10%, alternatively from about 0.2% to about 7%, alternatively from about 0.4% to about 5% of one or more silicones, and alternatively from about 0.5% to about 1%, by weight of the shampoo composition.

The average particle size of the one or more silicones may be from about 1 nm to about 100 nm, alternatively from about 5 nm to about 100 nm, alternatively from about 10 nm to about 80 nm, alternatively about 10 nm to about 60 nm, alternatively about 10 nm to about 50 nm, and alternatively about 20 nm to about 50 nm. The average particle size of the one or more silicones may be less than or equal to 100 nm, alternatively less than or equal to 90 nm, alternatively less than or equal to 80 nm, alternatively less than or equal to 70 nm, alternatively less than or equal to 60 nm, alternatively less than or equal to 55 nm, alternatively less than or equal to 50 nm, alternatively less than or equal to 40 nm, and alternatively less than or equal to 30 nm. The average particle size of the one or more silicones may be greater than or equal to 1 nm, greater than or equal to 5 nm, greater than or equal to 10 nm, and greater than or equal to 20 nm.

The particle size of the one or more silicones may be measured by dynamic light scattering (DLS). A Malvern Zetasizer Nano ZEN3600 system (www.malvern.com) using He—Ne laser 633 nm may be used for the measurement at 25° C.

The autocorrelation function may be analyzed using the Zetasizer Software provided by Malvern Instruments, which determines the effective hydrodynamic radius, using the Stokes-Einstein equation:

$$D = \frac{k_B T}{6\pi \eta R}$$

wherein $k_B$ is the Boltzmann Constant, T is the absolute temperature, $\eta$ is the viscosity of the medium, D is the mean diffusion coefficient of the scattering species, and R is the hydrodynamic radius of particles.

Particle size (i.e. hydrodynamic radius) may be obtained by correlating the observed speckle pattern that arises due to Brownian motion and solving the Stokes-Einstein equation, which relates the particle size to the measured diffusion constant, as is known in the art.

Polydispersity index (PDI) is a dimensionless measure of the broadness of the size distribution calculated from the cumulants analysis in Dynamic Light Scattering and is calculated according to the following equation.

Polydispersity index (PDI)=(the square of standard deviation)/(the square of mean diameter)

The polydispersity index (PDI) of the average silicone droplet size can be less than 0.5, alternatively less than 0.4, alternatively less than 0.3, and alternatively less than 0.2. The PDI of the average silicone size can be from 0 to about 0.6, alternatively from about 0 to about 0.4, alternatively from about 0 to about 0.2.

For each sample, 3 measurements may be made, and Z-average values may be reported as the average particle size.

The one or more silicones may be in the form of a nanoemulsion. The average particle size referred to herein is z-average measured by dynamic light scattering. The nanoemulsion may comprise any silicone suitable for application to the skin and/or hair. The nanoemulsion described herein may be prepared by the following methods: (1) mechanically breaking down the emulsion droplet size; (2) spontaneously forming the emulsion (may be referred to as a microemulsion in the literature); and (3) using emulsion polymerization to achieve average particle size in the target range described herein. From about 25% to about 100% of the one or more silicones can be in the form of a nanoemulsion, in another embodiment from about 50% to about 100% of the one or more silicones can be in the form of a nanoemulsion, and in another embodiment from about 75% to about 100% of the one or more silicones can be in the form of a nanoemulsion.

Silicone Polymer Containing Quaternary Groups

The compositions of the present invention comprise a low viscosity silicone polymer having a viscosity up to 100,000 mPa·s. Without being bound by theory, this low viscosity silicone polymer provides improved conditioning benefits over conventional silicones because of the addition of hydrophilic functionalities—quaternary amines, ethylene oxides/propylene oxides. Compared to previously disclosed silicones with quaternary functionality, these new structures are significantly lower in viscosity, so that they don't have to be blended with other lower viscosity diluents and dispersants to allow them to be formulated into products. Low viscosity silicone solvents and diluents can often cause viscosity and stability tradeoffs in shampoo products. The current invention eliminates the need for these materials since the silicone polymer is low enough in viscosity to be added directly or in emulsion form. The improved conditioning benefits include smooth feel, reduced friction, and prevention of hair damage, while, in some embodiments, eliminating the need for a silicone blend.

Structurally, the silicone polymer is a polyorganosiloxane compound comprising one or more quaternary ammonium groups, at least one silicone block comprising an average between 99 and 199 siloxane units, at least one polyalkylene oxide structural unit, and at least one terminal ester group. The silicone block may comprise an average from about 99 to about 199 siloxane units, alternatively from about 110 to about 199 siloxane units, alternatively about 120 to about 199 siloxane units, alternatively about 130 to about 199 siloxane units, alternatively about 110 to about 190 siloxane units, alternatively about 130 to about 190 siloxane units, alternatively about 110 to about 175 siloxane units, alternatively about 120 to about 175 siloxane units, alternatively about 130 to about 175 siloxane units, alternatively about 110 to about 155 siloxane units, alternatively about 120 to about 155 siloxane units, alternatively about 130 to about 155 siloxane units, alternatively about 155 to about 199 siloxane units, alternatively about 155 to about 190 siloxane units, and alternatively about 155 to about 175 siloxane units. The silicone block may comprise on average from about 120 to about 170 siloxane units, and alternatively from about 120 to about 145 siloxane units. The silicone block may comprise on average from about 145 to about 170 siloxane units.

The silicone block may comprise greater than or equal to 99 siloxane units, alternatively greater than 120 siloxane units, alternatively greater than 130 siloxane units, alternatively greater than 135 siloxane units, alternatively greater than 140 siloxane units, alternatively greater than or equal to 145 siloxane units. The silicone block may comprise less than 200 siloxane units, alternatively less than 180 siloxane units, alternatively less than 175 siloxane units, alternatively less than or equal to 170 siloxane units.

The average block length reflects mean values. They can be determined by i.e. 1H-NMR spectroscopy or GPC using protocols known in the art.

The polyorganosiloxane compounds can have a molar ratio of silicone to alkylene oxide block of about 2:1 to about 20:1, alternatively from about 4:1 to about 16:1, alternatively from about 6:1 to about 12:1, and alternatively from about 8:1 to about 10:1.

The nitrogen content for the polyoranosiloxane compounds can be from about 0.1 to about 0.4 mmol N/g polymer, alternatively from about 0.1 to about 0.3 mm N/g polymer, and alternatively from about 0.13 to about 0.27 mmol N/g polymer. The nitrogen content for the polyoranosiloxane compounds can be from about 0.13 to about 0.35 mmol N/g polymer, alternatively from about 0.15 to about 0.3 mmol N/g polymer, alternatively from about 0.17 to about 0.27 mmol N/g polymer, and alternatively from about 0.19 to about 0.24 mmol N/g polymer.

The polyorganosiloxane compounds according to the invention may have the general formulas (Ia) and (Ib):

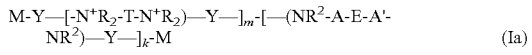

(Ia)

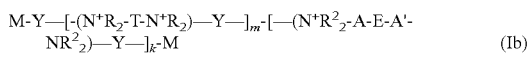

(Ib)

wherein:
m is >0, alternatively 0.01 to 100, alternatively 1 to 100, alternatively 1 to 50, alternatively 1 to 20, and alternatively 1 to 10,
k is 0 or an average value of from ≥0 to 50, alternatively from ≥0 to 20, and alternatively from ≥0 to 10,
M represents a terminal group, comprising terminal ester groups selected from

—OC(O)—Z

—OS(O)$_2$—Z

—OS(O$_2$)O—Z

—OP(O)(O—Z)OH

—OP(O)(O—Z)$_2$ wherein Z is selected from monovalent organic residues having up to 40 carbon atoms, optionally comprising one or more hetero atoms;
A and A' each are independently from each other selected from a single bond or a divalent organic group having up to 10 carbon atoms and one or more hetero atoms, and
E is a polyalkylene oxide group of the general formula:

—[CH$_2$CH$_2$O]$_q$—[CH$_2$CH(CH$_3$)O]$_r$—[CH$_2$CH(C$_2$H$_5$)O]$_s$— wherein q=0 to 200, alternatively 0 to 100, alternatively 0 to 50, alternatively 0 to 25, alternatively 0 to 10, alternatively 1 to 200, alternatively 1 to 100, alternatively 1 to 50, alternatively 1 to 25, and alternatively 1 to 10;
r=0 to 200, alternatively 0 to 100, alternatively 0 to 50, alternatively 0 to 25, and alternatively 0 to 10;
s=0 to 200, alternatively 0 to 100, alternatively 0 to 50, alternatively 0 to 30, and alternatively 0 to 25;
q+r+s=1 to 600, or alternatively from 1 to 100, or alternatively from 1 to 50, or alternatively from 1 to 40, or alternatively 1 to 30
with percentage of q in (q/(q+r+s))=0%, 0.166% to 100%, 1% to 100%, 2% to 100%, 2.5% to 100%, 10% to 100%, 30% to 100%, 50% to 100%; alternatively percentage of q in (q/(q+r+s))=at least 1%, alternatively at least 2%, alternatively at least 10%, alternatively at least 30% alternatively at least 50%, alternatively at least 75%, alternatively at least 90%, alternatively at least 95%, and alternatively 100%.
$R^2$ is selected from hydrogen or R,
R is selected from monovalent organic groups having up to 22 carbon atoms and optionally one or more heteroatoms, and wherein the free valencies at the nitrogen atoms are bound to carbon atoms,
Y is a group of the formula:

—K—S—K— and -A-E-A'— or -A'-E-A-, with S=

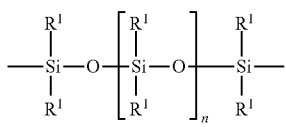

wherein R1=C$_1$-C$_{22}$-alkyl, C$_1$-C$_{22}$-fluoralkyl or aryl;
n=99 to 199 on average, alternatively 110 to 199 on average, alternatively 120 to 199 on average, alternatively 130 to 199 on average, alternatively 110 to 190 on average, alternatively 130 to 190 on average, alternatively 110 to 175 on average, alternatively 120 to 175 on average, alternatively 130 to 175 on average, alternatively 110 to 155 on average, alternatively 120 to 155 on average, alternatively 130 to 155 on average, alternatively 155 to 199 on average, alternatively 155 to 190 on average, alternatively 155 to 175 on average and these can be identical or different if several S Groups are present in the polyorganosiloxane compound;
K is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R$^1$ is defined as above,
T is selected from a divalent organic group having up to 20 carbon atoms and optionally one or more hetero atoms.

The residues K may be identical or different from each other. In the —K—S—K— moiety, the residue K is bound to the silicon atom of the residue S via a C—Si-bond.

Due to the possible presence of amine groups (—(NR$^2$-A-E-A'-NR$^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds according to the invention.

The molar ratio of the quaternary ammonium groups b) and the terminal ester groups c) is less than 20:3, alternatively less than 5:1, alternatively less than 10:3 and alternatively less than 2:1. The ratio can be determined by $^{13}$C-NMR or 1H-NMR.

The silicone polymer has a viscosity at 20° C. and a shear rate of 0.1 s$^{-1}$ (plate-plate system, plate diameter 40 mm, gap width 0.5 mm) of less than 100,000 mPa·s (100 mPa·s). The viscosities of the neat silicone polymers may range from about 500 to about 100,000 mPa·s, alternatively from about 500 to about 70,000 mPa·s, alternatively from about 500 to about 50,000 mPa·s, alternatively from about 500 to about 30,000 mPa·s, alternatively from about 2,000 to about 100,000 mPa·s, alternatively from about 2,000 to about 70,000 mPa·s, alternatively from about 2,000 to about 50,000 mPa·s, alternatively from about 2,000 to about 30,000 mPa·s, alternatively from about 8,000 to about 100,000 mPa·s, alternatively from about 8,000 to about 70,000 mPa·s, alternatively from about 8,000 to about 50,000 mPa·s, alternatively from about 8,000 to about 30,000 mPa·s, alternatively from about 15,000 to about 100,000 mPa·s, alternatively from about 15,000 to about 70,000 mPa·s, alternatively from about 15,000 to about 50,000 mPa·s, alternatively from about 15,000 to about 30,000 mPa·s determined at 20° C. and a shear rate of 0.1 s$^{-1}$.

In addition to the above listed silicone polymers, it can be desirably to use the embodiments provided below. For example, in the polyalkylene oxide group E of the general formula:

—[CH$_2$CH$_2$O]$_q$—[CH$_2$CH(CH$_3$)O]$_r$—[CH$_2$CH(C$_2$H$_5$)O]$_s$— wherein the q, r, and s indices may be defined as follows:
q=1 to 200, or alternatively 1 to 100, or alternatively from 1 to 50, or alternatively from 1 to 20, r=0 to 200, or alternatively from 0 to 100, or alternatively from 0 to 50, or alternatively from 0 to 20, s=0 to 200, or alternatively from 0 to 100, or alternatively from 0 to 50, or alternatively from 0 to 20, q+r+s=1 to 600, or alternatively from 1 to 100, or alternatively from 1 to 50, or alternatively from 1 to 40 with percentage of q in (q/(q+r+s)) 0%, 0.166% to 100%, 1% to 100%, 2% to 100%, 2.5% to 100%, 10% to 100%, 30% to 100%, 50% to 100%.

For polyorganosiloxane structural units with the general formula S:

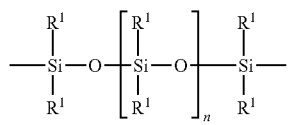

$R^1 = C_1$-$C_{22}$-alkyl, $C_1$-$C_{22}$-fluoralkyl or aryl; n=from 99 to 199, K (in the group —K—S—K—) is preferably a bivalent or trivalent straight chain, cyclical or branched $C_2$-$C_{20}$ hydrocarbon residue which is optionally interrupted by —O—, —NH—, trivalent N, —NR$^1$—, —C(O)—, —C(S)—, and optionally substituted with —OH.

$R^1$ can be $C_1$-$C_{18}$ alkyl, $C_1$-$C_{18}$ fluoroalkyl and aryl. Furthermore, $R^1$ is preferably $C_1$-$C_{18}$ alkyl, $C_1$-$C_6$ fluoroalkyl and aryl. Furthermore, $R^1$ is alternatively $C_1$-$C_6$ alkyl, $C_1$-$C_6$ fluoroalkyl, alternatively $C_1$-$C_4$ fluoroalkyl, and phenyl. Alternatively, $R^1$ is methyl, ethyl, trifluoropropyl and phenyl.

As used herein, the term "$C_1$-$C_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "$C_1$-$C_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, CF$_3$, $C_1$-$C_6$ alkyl, $C_1$-$C_6$ alkoxy, $C_3$-$C_7$ cycloalkyl, $C_2$-$C_6$ alkenyl or phenyl. Aryl may also mean naphthyl.

The positive charges resulting from the ammonium group(s) of the polyorganosiloxane, can be neutralized with inorganic anions such as chloride, bromide, hydrogen sulfate, sulfate, or organic anions, like carboxylates deriving from $C_1$-$C_{30}$ carboxylic acids, for example acetate, propionate, octanoate, especially from $C_{10}$-$C_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

The polyorganosiloxane compounds can be of the general formulas (Ia) and (Ib):

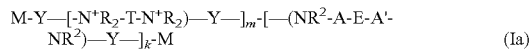   (Ia)

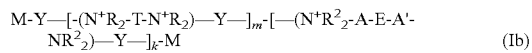   (Ib)

wherein each group is as defined above; however, the repeating units are in a statistical arrangement (i.e., not a block-wise arrangement).

The polyorganosiloxane compounds may be also of the general formulas (IIa) or (IIb):

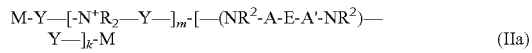   (IIa)

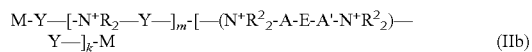   (IIb)

wherein each group is as defined above. Also, in such formula the repeating units are usually in a statistical arrangement (i.e. not a block-wise arrangement).

wherein, as defined above, M is

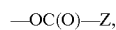

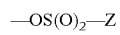

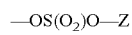

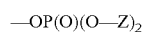

Z is a straight chain, cyclic or branched saturated or unsaturated $C_1$-$C_{20}$, or preferably $C_2$ to $C_{18}$, or even more preferably a hydrocarbon radical, which can be interrupted by one or more —O—, or —C(O)— and substituted with —OH. M can be —OC(O)—Z resulting from normal carboxylic acids in particular with more than 10 carbon atoms like for example dodecanoic acid.

The molar ratio of the polyorganosiloxane-containing repeating group —K—S—K— and the polyalkylene repeating group -A-E-A'- or -A'-E-A- is between 1:100 and 100:1, alternatively between 1:20 to 20:1, or alternatively between 1:10 to 10:1.

In the group —(N$^+$R$_2$-T-N$^+$R$_2$)—, R may represent a monovalent straight chain, cyclic or branched $C_1$-$C_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters can include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Detersive Surfactant

The compact shampoo compositions described herein can include one or more detersive surfactants. The detersive surfactant can be selected from anionic surfactants, amphoteric surfactants, zwitterionic surfactants, and combinations thereof.

The concentration of the detersive surfactant in the composition should be sufficient to provide the desired cleaning and lather performance. The compact shampoo composition can comprise a total detersive surfactant level of from about 4% to about 45%, by weight, from about 10% to about 40%, by weight, and/or from about 12% to about 35%, by weight, from about 15% to about 30%, by weight, and/or from about 17% to about 28%, and/or from about 20% to about 25%. The compact shampoo composition can comprise a total detersive surfactant level of from greater than 13%, greater than 16%, greater than 20%, greater than 22%, and/or greater than 25% by weight.

The detersive surfactant can comprise an anionic surfactant. Suitable anionic detersive surfactant components for use in the composition herein can include those which are known for use in hair care or other personal care compositions, including shampoos. Suitable anionic surfactants for compact shampoo compositions described herein can include alkyl sulfates and alkyl ether sulfates, water-soluble olefin sulfonates, beta-alkyloxy alkane sulfonates, other sulfonates, succinate surfactants, other sulfonates, and/or other surfactants that are substantially free of sulfates.

The compact shampoo composition may comprise from about 2% to about 40%, from about 4% to about 36%, from about 8% to about 32%, from about 10% to about 30%, and/or from about 12% to about 28%, by weight, of one or more anionic detersive surfactants.

Anionic surfactants suitable for use herein include alkyl sulfates and alkyl ether sulfates of the formula $ROSO_3M$ and $RO(C_2H_4O)_xSO_3M$, wherein R can be a linear or branched alkyl or alkenyl chain of from about 8 to about 18 carbon atoms, x can be from 1 to 10, and M is a water-soluble cation such as ammonium, sodium, potassium, and triethanolamine cation or salts of the divalent magnesium ion with two anionic surfactant anions. The alkyl ether sulfates may be made as condensation products of ethylene oxide and monohydric alcohols having from about 8 to about 24 carbon atoms. The alcohols can be derived from fats such as coconut oil, palm oil, palm kernel oil, or tallow, or can be synthetic.

The composition can also include anionic alkyl sulfates and alkyl ether sulfate surfactants having branched alkyl chains which are synthesized from C8 to C18 branched alcohols which may be selected from: Guerbet alcohols, aldol condensation derived alcohols, oxo alcohols and mixtures thereof. Non-limiting examples of the 2-alkyl branched alcohols include oxo alcohols such as 2-methyl-1-undecanol, 2-ethyl-1-decanol, 2-propyl-1-nonanol, 2-butyl 1-octanol, 2-methyl-1-dodecanol, 2-ethyl-1-undecanol, 2-propyl-1-decanol, 2-butyl-1-nonanol, 2-pentyl-1-octanol, 2-pentyl-1-heptanol, and those sold under the tradenames LIAL® (Sasol), ISALCHEM® (Sasol), and NEODOL® (Shell), and Guerbet and aldol condensation derived alcohols such as 2-ethyl-1-hexanol, 2-propyl-1-butanol, 2-butyl-1-octanol, 2-butyl-1-decanol, 2-pentyl-1-nonanol, 2-hexyl-1-octanol, 2-hexyl-1-decanol and those sold under the tradename ISOFOL® (Sasol) or sold as alcohol ethoxylates and alkoxylates under the tradenames LUTENSOL XP® (BASF) and LUTENSOL XL® (BASF).

The anionic alkyl sulfates and alkyl ether sulfates may also include those synthesized from C8 to C18 branched alcohols derived from butylene or propylene which are sold under the trade names EXXAL™ (Exxon) and Marlipal® (Sasol). This includes anionic surfactants of the subclass of sodium trideceth-n sulfates (STnS), where n is between about 0.5 and about 3.5. Exemplary surfactants of this subclass are sodium trideceth-2 sulfates and sodium trideceth-3 sulfates. The composition can also include sodium tridecyl sulfate.

Suitable surfactants that are substantially free of sulfates can include isethionates, sarcosinates, sulfonates, sulfosuccinates, sulfoacetates, glycinates, glutamates, glucose carboxylates, amphoacetates. taurates, other acyl aminoacids, betaines, sultaines, and/or phosphate esters. Suitable surfactants that are substantially free of sulfates can contain carboxylic acids.

The composition can contain suitable anionic detersive surfactants, which can include water-soluble olefin sulfonates which have the general formula $R^1$—$SO_3M$ where $R^1$ is a straight or branched chain, saturated, aliphatic hydrocarbon radical having from 10 to 24 carbon atoms, 10 to 18 carbon atoms, or from 13 to 15 carbon atoms; and M is a water-soluble cation such as ammonium, sodium, potassium, triethanolamine cation, or salts of the divalent magnesium ion with two anionic surfactant anions. Suitable olefin sulfonates such as sodium paraffin sulfonates can be produced through the reaction of $SO_2$ and $O_2$ with a suitable chain length paraffin.

Suitable anionic detersive surfactants can include beta-alkyloxy alkane sulfonates. Beta-alkyloxy alkane sulfonates surfactants conform to Formula I:

TABLE 1

Examples of Typical Alkyl Sulfates and Alky Ether Sulfates

| Surfactant | Supplier | Activity | SLS | SLE1S | SLE2S | SLE3S | SLE > 3S |
|---|---|---|---|---|---|---|---|
| Sodium Lauryl Sulfate | Stepan STEOL SLS | 29% by weight | 100 | 0 | 0 | 0 | 0 |
| Sodium Laureth-1 Sulfate | Stepan STEOL SLES-1 | 26% by weight | 45.5 | 26.3 | 11.8 | 0.07 | 16.33 |
| Sodium Laureth-3 Sulfate | Stepan STEOL SLES-3 | 28% by weight | 18 | 16.7 | 12.6 | 12.4 | 40.30 |

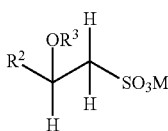

where $R^2$ is a straight chain alkyl group having from about 6 to about 20 carbon atoms, $R^3$ is a lower alkyl group having from about 1 to about 3 carbon atoms, preferably 1 carbon atom, and M is a water-soluble cation as previously described in the water-soluble olefin sulfonates.

Suitable anionic detersive surfactants can include isethionate surfactants. For example, suitable isethionate surfactants can include the reaction product of fatty acids esterified with isethionic acid and neutralized with sodium hydroxide. Suitable fatty acids for isethionate surfactants can be derived from coconut oil or palm kernel oil including amides of methyl tauride.

Detersive anionic surfactants can be succinate surfactants. Examples of suitable succinate surfactants can include disodium N-octadecylsulfo succinate, disodium lauryl sulfosuccinate, diammonium lauryl sulfosuccinate, laureth sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid, and dioctyl esters of sodium sulfosuccinic acid. Examples of additional anionic surfactants suitable for use herein include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, sodium lauryl sarcosine, sodium cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium trideceth-1 sulfate, sulfate, sodium trideceth-2 sulfate, sulfate, sodium trideceth-3 sulfate, sodium tridecyl sulfate, sodium methyl lauroyl taurate, sodium methyl cocoyl taurate, sodium lauroyl isethionate, sodium lauroyl methyl isethionate ("SLMI"), sodium laureth sulfosuccinate, sodium lauryl sulfosuccinate, sodium $C_{12}$-$C_{14}$ olefin sulfonate, sodium tridecyl benzene sulfonate, sodium dodecyl benzene sulfonate, sodium lauroyl glycinate, sodium cocoamphoacetate, sodium cocoyl glutamate, sodium lauroyl glutamate, sodium lauryl glucose carboxylate, sodium phosphate ester surfactants, and fatty acid surfactants. and mixtures thereof.

Additional anionic surfactants suitable for use herein include, but not limited to, acyl isethionate, acyl methyl isethionate, acyl glutamate, acyl glycinate, acyl sarcosinate, acyl alaninate, acyl taurate, sulfosuccinate, alkyl benzene sulfonate, alkyl ether carboxylate, alkylamphoacetate, alpha olefin sulfonate, and mixtures thereof. Examples of such suitable anionic surfactants include, but not limited to, sodium cocoyl isethionate (SCI), sodium lauroyl isethionate, sodium lauroyl methyl isethionate, sodium cocoyl glutamate, disodium cocoyl glutamate, sodium lauroyl glutamate, disodium lauroyl glutamate, sodium cocoyl alaninate, sodium lauroyl alaninate, sodium lauroyl glycinate, sodium cocoyl glycinate, sodium laureth sulfosuccinate, disodium laureth sulfosuccinate, sodium lauryl sulfosuccinate, disodium lauryl sulfosuccinate, sodium lauryl glucose carboxylate, sodium cocoyl glucose carboxylate, sodium cocoyl amphoacetate, sodium lauroyl amphoacetate, sodium methyl cocoyl taurate, and mixtures thereof.

The compact shampoo composition may comprise from about 0% to about 25%, from about 0.1% to about 20%, from about 0.5% to about 15%, from about 1% to about 10%, by weight, of one or more co-surfactants selected from the group consisting of amphoteric surfactants, zwitterionic surfactants, non-inonic surfactants, and mixtures thereof. The composition can comprise a co-surfactant selected from the group consisting of: amphoteric surfactants, zwitterionic surfactants, and mixtures thereof. Non-limiting examples of suitable zwitterionic or amphoteric surfactants are described in U.S. Pat. No. 5,104,646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. The amphoteric surfactant can be selected from the group consisting of: sodium cocaminopropionate, sodium cocaminodipropionate, sodium cocoamphoacetate, sodium cocoamphohydroxypropylsulfonate, sodium cocoamphopropionate, sodium comamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium comamphopropionate, ammonium lauraminopropionate, ammonium lauroamphoacetate, ammonium lauroamphohydroxypropylsulfonate, ammonium lauroamphopropionate, ammonium comamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine comamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof.

The amphoteric surfactant can be a surfactant according to the following structure:

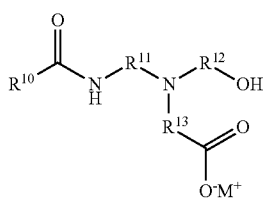

wherein $R^{10}$ is a C-linked monovalent substituent selected from the group consisting of: substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; and wherein $R^{11}$, $R^{12}$, and $R^{13}$ are each independently selected from the group consisting of: C-linked divalent straight alkyl systems comprising 1 to 3 carbon atoms, and C-linked divalent branched alkyl systems comprising 1 to 3 carbon atoms; and wherein M is a monovalent counterion selected from the group consisting of sodium, ammonium and protonated triethanolamine. The amphoteric surfactant is selected from the group consisting of: sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

The detersive surfactant system may comprise at least 1%, by weight, of the composition, of one or more zwitterionic surfactants which possess a hydroxyl group in their molecular structure. The zwitterionic surfactant can be a derivative of an aliphatic quaternary ammonium, phosphonium, and sulfonium compound, in which the aliphatic radicals are straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant is selected from the group consisting of: cocamidoethyl betaine, cocamidopropylamine oxide, cocamidopropyl betaine, cocamidopropyl dimethylamino-hydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. The zwitterionic surfactant can be selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

The surfactant can be selected from the group consisting of: zwitterionic surfactants, amphoteric surfactants, non-ionic surfactants, and mixtures thereof. The surfactant can be an anionic surfactant and the composition further comprises a co-surfactant, wherein the co-surfactant is selected from the group consisting of: zwitterionic surfactants, amphoteric surfactants, non-ionic surfactants, and mixtures thereof. The co-surfactant can be a non-ionic surfactant selected from the group consisting of: Cocamide, Cocamide Methyl MEA, Cocamide DEA, Cocamide MEA, Cocamide MIPA, Lauramide DEA, Lauramide MEA, Lauramide MIPA, Myristamide DEA, Myristamide MEA, PEG-20 Cocamide MEA, PEG-2 Cocamide, PEG-3 Cocamide, PEG-4 Cocamide, PEG-5 Cocamide, PEG-6 Cocamide, PEG-7 Cocamide, PEG-3 Lauramide, PEG-5 Lauramide, PEG-3 Oleamide, PPG-2 Cocamide, PPG-2 Hydroxyethyl Cocamide, and mixtures thereof. The co-surfactant can be a zwitterionic surfactant, wherein the zwitterionic surfactant is selected from the group consisting of: lauryl hydroxysultaine, cocamidopropyl hydroxysultaine, coco-betaine, coco-hydroxysultaine, cocosultaine, lauryl betaine, lauryl sultaine, and mixtures thereof.

Liquid Carrier

Inclusion of an appropriate quantity of a liquid carrier can facilitate the formation of a shampoo composition having an appropriate liquid viscosity and rheology. A shampoo composition can include, by weight of the composition, about 50% to about 95%, of a liquid carrier, about 60% to about 85%, about 65% to about 80%, about 68% to about 78%, and/or about 70% to about 77%.

A liquid carrier can be water or can be a miscible mixture of water and organic solvent. A liquid carrier can be water with minimal or no significant concentrations of organic solvent, except as otherwise incidentally incorporated into the composition as minor ingredients of other essential or optional components. Suitable organic solvents can include water solutions of lower alkyl alcohols and polyhydric alcohols. Useful lower alkyl alcohols include monohydric alcohols having 1 to 6 carbons, such as ethanol and isopropanol. Exemplary polyhydric alcohols include propylene glycol, hexylene glycol, glycerin, and propane diol.

Optional Ingredients

The foamed shampoo composition may further comprise one or more optional ingredients, including but not limited to, benefit agents. Suitable benefit agents include, but are not limited to non-silicone conditioning agents, cationic polymers, anti-dandruff actives, gel networks, chelating agents, and natural oils such as sun flower oil or castor oil. Additional suitable optional ingredients include but are not limited to perfumes, perfume microcapsules, colorants, particles, anti-microbials, foam busters, anti-static agents, rheology modifiers and thickeners, suspension materials and structurants, pH adjusting agents and buffers, preservatives, pearlescent agents, solvents, diluents, anti-oxidants, vitamins and combinations thereof.

Such optional ingredients should be physically and chemically compatible with the components of the composition, and should not otherwise unduly impair product stability, aesthetics, or performance. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein.

Non-Silicone Conditioning Agents

The conditioning agent of the foamed shampoo compositions described herein may also comprise at least one organic conditioning agents, either alone or in combination with other conditioning agents, such as the silicones described above. Non-limiting examples of organic conditioning agents are described below.

Hydrocarbon Oils

Suitable organic conditioning agents for use as conditioning agents in shampoo compositions include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils can be from about $C_{12}$ to about $C_{19}$. Branched chain hydrocarbon oils, including hydrocarbon polymers, typically will contain more than 19 carbon atoms.

Polyolefins

Organic conditioning oils for use in the foamed shampoo compositions described herein also include liquid polyolefins, including liquid poly-α-olefins and/or hydrogenated liquid poly-α-olefins. Polyolefins for use herein are prepared by polymerization of $C_4$ to about $C_{14}$ olefenic monomers, and in one embodiment from about $C_6$ to about $C_{12}$.

Fatty Esters

Other suitable organic conditioning agents for use as a conditioning agent in the foamed shampoo compositions described herein include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.). Other oligomeric or polymeric esters, prepared from unsaturated glyceryl esters can also be used as conditioning materials.

Fluorinated Conditioning Compounds

Fluorinated compounds suitable for delivering conditioning to hair as organic conditioning agents include perfluoropolyethers, perfluorinated olefins, fluorine based specialty polymers that may be in a fluid or elastomer form similar to the silicone fluids previously described, and perfluorinated dimethicones.

Fatty Alcohols

Other suitable organic conditioning oils for use in the foamed shampoo compositions described herein include, but are not limited to, fatty alcohols having at least about 10 carbon atoms, about 10 to about 22 carbon atoms, and in one embodiment about 12 to about 16 carbon atoms.

Alkyl Glucosides and Alkyl Glucoside Derivatives

Suitable organic conditioning oils for use in the foamed shampoo compositions described herein include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

Cationic Polymer

The shampoo composition can also comprise a cationic polymer. These cationic polymers can include at least one of (a) a cationic guar polymer, (b) a cationic non-guar galactomannan polymer, (c) a cationic tapioca polymer, (d) a cationic copolymer of acrylamide monomers and cationic monomers, and/or (e) a synthetic, non-crosslinked, cationic polymer, which may or may not form lyotropic liquid crystals upon combination with the detersive surfactant (f) a cationic cellulose polymer. Additionally, the cationic polymer can be a mixture of cationic polymers.

The shampoo composition may comprise a cationic guar polymer, which is a cationically substituted galactomannan (guar) gum derivatives. Guar gum for use in preparing these guar gum derivatives is typically obtained as a naturally occurring material from the seeds of the guar plant. The guar molecule itself is a straight chain mannan, which is branched at regular intervals with single membered galactose units on alternative mannose units. The mannose units are linked to each other by means of β(1-4) glycosidic linkages. The galactose branching arises by way of an α(1-6) linkage. Cationic derivatives of the guar gums are obtained by reaction between the hydroxyl groups of the polygalactomannan and reactive quaternary ammonium compounds. The degree of substitution of the cationic groups onto the guar structure should be sufficient to provide the requisite cationic charge density described above.

The cationic polymer, can include, but not limited, to a cationic guar polymer, has a weight average molecular weight of less than 2.0 million g/mol, or from about 10 thousand to about 2 million g/mol, or from about 50 thousand to about 2 million g/mol, or from about 100 thousand to about 2 million g/mol, or from about 10 thousand to about 1 million g/mol, or from about 25 thousand to about 1 million g/mol, or from about 50 thousand to about 1 million g/mol, or from about 100 thousand to about 1 million g/mol. The cationic guar polymer can have a charge density of from about 0.2 to about 2.2 meq/g, or from about 0.3 to about 2.0 meq/g, or from about 0.4 to about 1.8 meq/g; or from about 0.5 meq/g to about 1.7 meq/g.

The cationic guar polymer can have a weight average molecular weight of less than 1.0 million g/mol, and has a charge density of from about 0.1 meq/g to about 2.5 meq/g. In an embodiment, the cationic guar polymer has a weight average molecular weight of less than 950 thousand g/mol, or from about 10 thousand to about 900 thousand g/mol, or from about 25 thousand to about 900 thousand g/mol, or from about 50 thousand to about 900 thousand g/mol, or from about 100 thousand to about 900 thousand g/mol. from about 150 thousand to about 800 thousand g/mol. The cationic guar polymer can have a charge density of from about 0.2 to about 2.2 meq/g, or from about 0.3 to about 2.0 meq/g, or from about 0.4 to about 1.8 meq/g; or from about 0.5 meq/g to about 1.5 meq/g. The shampoo composition can comprise from about from about 0.05% to about 2%, from about 0.05% to about 1.8%, from about 0.05% to about 1.5%, from about 0.05% to about 1.2%, from about 0.05% to about 1%, from about 0.05% to about 0.9%, from about 0.1% to about 0.8%, or from about 0.2% to about 0.7% of cationic polymer (a), by total weight of the composition.

The cationic guar polymer may be formed from quaternary ammonium compounds. The quaternary ammonium compounds for forming the cationic guar polymer can conform to the general formula 1:

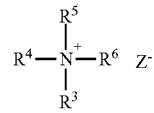

wherein where $R^3$, $R^4$ and $R^5$ are methyl or ethyl groups; $R^6$ is either an epoxyalkyl group of the general formula 2:

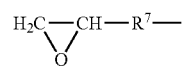

or $R^6$ is a halohydrin group of the general formula 3:

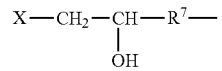

wherein R⁷ is a C₁ to C₃ alkylene; X is chlorine or bromine, and Z is an anion such as Cl—, Br—, I— or HSO₄—.

The cationic guar polymer can conform to the general formula 4:

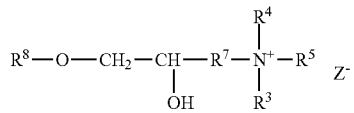

wherein R⁸ is guar gum; and wherein R⁴, R⁵, R⁶ and R⁷ are as defined above; and wherein Z is a halogen. The cationic guar polymer can conform to Formula 5:

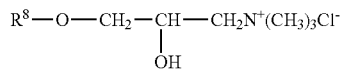

Suitable cationic guar polymers include cationic guar gum derivatives, such as guar hydroxypropyltrimonium chloride. The cationic guar polymer can be a guar hydroxypropyltrimonium chloride. Specific examples of guar hydroxypropyltrimonium chlorides include the Jaguar® series commercially available from Rhone-Poulenc Incorporated, for example Jaguar® C-500, commercially available from Rhodia. Jaguar® C-500 has a charge density of 0.8 meq/g and a weight average molecular weight of 500,000 g/mol. Other suitable guar hydroxypropyltrimonium chloride are: guar hydroxypropyltrimonium chloride which has a charge density of about 1.1 meq/g and a weight average molecular weight of about 500,000 g/mol is available from ASI, a charge density of about 1.5 meq/g and a weight average molecular weight of about 500,000 g/mole is available from ASI. Other suitable guar hydroxypropyltrimonium chloride are: Hi-Care 1000, which has a charge density of about 0.7 meq/g and a Weight average molecular weight of about 600,000 g/mole and is available from Rhodia; N-Hance™ 3269 and N-Hance™ 3270, which has a charge density of about 0.7 meq/g and a weight average molecular weight of about 425,000 g/mol and is available from ASI, N-Hance™ 3271 which has a charge density of about 0.7 meq/g and a weight average molecular weight of about 500,000 g/mol and is available from Ashland™; AquaCat™ CG518 has a charge density of about 0.9 meq/g and a Weight average molecular weight of about 50,000 g/mol and is available from ASI. BF-13, which is a borate (boron) free guar of charge density of about 1.1 meq/g and weight average molecular weight of about 800,000 and BF-17, which is a borate (boron) free guar of charge density of about 1.7 meq/g and M. W.t of about 800,000 both available from ASI.

Other suitable guar hydroxypropyltrimonium chloride are: N-Hance™ CG17 has a charge density of about 1.0 meq/g and a weight average molecular weight of about 1,600,000 g/mol and is available from Ashland™; and N-Hance™ 3196 has a charge density of about 0.7 meq/g and a weight average molecular weight of 1,700,000 g/mol and is available from Ashland™.

The shampoo compositions may comprise a galactomannan polymer derivative having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Non-Guar Galactomannan polymer derivatives suitable for use can have a ratio of mannose to galactose of greater than 2:1 on a monomer to monomer basis. Suitable ratios of mannose to galactose can be greater than about 3:1, and the ratio of mannose to galactose can be greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

The non-guar galactomannan polymer derivatives can have a M. Wt. from about 1,000 to about 1,000,000, and/or form about 5,000 to about 900,000.

The shampoo compositions of the can also include galactomannan polymer derivatives which have a cationic charge density from about 0.5 meq/g to about 7 meq/g. The galactomannan polymer derivatives can have a cationic charge density from about 1 meq/g to about 5 meq/g. The degree of substitution of the cationic groups onto the galactomannan structure should be sufficient to provide the requisite cationic charge density.

The galactomannan polymer derivative can be a cationic derivative of the non-guar galactomannan polymer, which is obtained by reaction between the hydroxyl groups of the polygalactomannan polymer and reactive quaternary ammonium compounds. Suitable quaternary ammonium compounds for use in forming the cationic galactomannan polymer derivatives include those conforming to the general formulas 1-5, as defined above.

Cationic non-guar galactomannan polymer derivatives formed from the reagents described above are represented by the general formula 6:

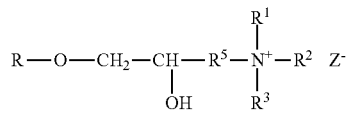

wherein R is the gum. The cationic galactomannan derivative can be a gum hydroxypropyltrimethylammonium chloride, which can be more specifically represented by the general formula 7:

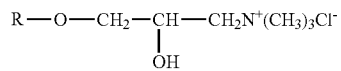

Alternatively, the galactomannan polymer derivative can be an amphoteric galactomannan polymer derivative having a net positive charge, obtained when the cationic galactomannan polymer derivative further comprises an anionic group.

The cationic non-guar galactomannan can have a ratio of mannose to galactose is greater than about 4:1, a weight average molecular weight of about 50,000 g/mol to about 1,000,000 g/mol, and/or from about 100,000 g/mol to about 900,000 g/mol and a cationic charge density from about 1 meq/g to about 5 meq/g, and/or from 2 meq/g to about 4 meq/g and can also be derived from a cassia plant.

The shampoo compositions can comprise at least about 0.05% of a galactomannan polymer derivative by weight of the composition, alternatively from about 0.05% to about 2%, by weight of the composition, of a galactomannan polymer derivative.

The shampoo compositions can comprise water-soluble cationically modified starch polymers. As used herein, the term "cationically modified starch" refers to a starch to which a cationic group is added prior to degradation of the starch to a smaller molecular weight, or wherein a cationic group is added after modification of the starch to achieve a desired molecular weight. The definition of the term "cationically modified starch" also includes amphoterically modified starch. The term "amphoterically modified starch" refers to a starch hydrolysate to which a cationic group and an anionic group are added.

The shampoo compositions can comprise cationically modified starch polymers at a range of about 0.01% to about 10%, and/or from about 0.05% to about 5%, by weight of the composition.

The cationically modified starch polymers disclosed herein have a percent of bound nitrogen of from about 0.5% to about 4%.

The cationically modified starch polymers for use in the shampoo compositions can have a weight average molecular weight about 50,000 g/mol to about 1,000,000 g/mol and/or from about 100,000 g/mol to about 1,000,000 g/mol.

The shampoo compositions can include cationically modified starch polymers which have a charge density of from about 0.2 meq/g to about 5 meq/g, and/or from about 0.2 meq/g to about 2 meq/g. The chemical modification to obtain such a charge density includes, but is not limited to, the addition of amino and/or ammonium groups into the starch molecules. Non-limiting examples of these ammonium groups may include substituents such as hydroxypropyl trimmonium chloride, trimethylhydroxypropyl ammonium chloride, dimethylstearylhydroxypropyl ammonium chloride, and dimethyldodecylhydroxypropyl ammonium chloride. See Solarek, D. B., Cationic Starches in Modified Starches: Properties and Uses, Wurzburg, O. B., Ed., CRC Press, Inc., Boca Raton, Fla. 1986, pp 113-125. The cationic groups may be added to the starch prior to degradation to a smaller molecular weight or the cationic groups may be added after such modification.

The cationically modified starch polymers generally have a degree of substitution of a cationic group from about 0.2 to about 2.5. As used herein, the "degree of substitution" of the cationically modified starch polymers is an average measure of the number of hydroxyl groups on each anhydroglucose unit which is derivatized by substituent groups. Since each anhydroglucose unit has three potential hydroxyl groups available for substitution, the maximum possible degree of substitution is 3. The degree of substitution is expressed as the number of moles of substituent groups per mole of anhydroglucose unit, on a molar average basis. The degree of substitution may be determined using proton nuclear magnetic resonance spectroscopy (".sup.1H NMR") methods well known in the art. Suitable .sup.1H NMR techniques include those described in "Observation on NMR Spectra of Starches in Dimethyl Sulfoxide, Iodine-Complexing, and Solvating in Water-Dimethyl Sulfoxide", Qin-Ji Peng and Arthur S. Perlin, Carbohydrate Research, 160 (1987), 57-72; and "An Approach to the Structural Analysis of Oligosaccharides by NMR Spectroscopy", J. Howard Bradbury and J. Grant Collins, Carbohydrate Research, 71, (1979), 15-25.

The source of starch before chemical modification can be chosen from a variety of sources such as tubers, legumes, cereal, and grains. Non-limiting examples of this source starch may include corn starch, wheat starch, rice starch, waxy corn starch, oat starch, cassaya starch, waxy barley, waxy rice starch, glutenous rice starch, sweet rice starch, amioca, potato starch, tapioca starch, oat starch, sago starch, sweet rice, or mixtures thereof.

The cationically modified starch polymers can be selected from degraded cationic maize starch, cationic tapioca, cationic potato starch, and mixtures thereof. Alternatively, the cationically modified starch polymers are cationic corn starch and cationic tapioca.

The starch, prior to degradation or after modification to a smaller molecular weight, may comprise one or more additional modifications. For example, these modifications may include cross-linking, stabilization reactions, phosphorylations, and hydrolyzations. Stabilization reactions may include alkylation and esterification.

The cationically modified starch polymers may be incorporated into the composition in the form of hydrolyzed starch (e.g., acid, enzyme, or alkaline degradation), oxidized starch (e.g., peroxide, peracid, hypochlorite, alkaline, or any other oxidizing agent), physically/mechanically degraded starch (e.g., via the thermo-mechanical energy input of the processing equipment), or combinations thereof.

An optimal form of the starch is one which is readily soluble in water and forms a substantially clear (% Transmittance.gtoreq.80 at 600 nm) solution in water. The transparency of the composition is measured by Ultra-Violet/Visible (UV/VIS) spectrophotometry, which determines the absorption or transmission of UV/VIS light by a sample, using a Gretag Macbeth Colorimeter Color i 5 according to the related instructions. A light wavelength of 600 nm has been shown to be adequate for characterizing the degree of clarity of cosmetic compositions.

Suitable cationically modified starch for use in shampoo compositions are available from known starch suppliers. Also suitable for use in shampoo compositions are nonionic modified starch that can be further derivatized to a cationically modified starch as is known in the art. Other suitable modified starch starting materials may be quaternized, as is known in the art, to produce the cationically modified starch polymer suitable for use in shampoo compositions.

Starch Degradation Procedure: a starch slurry can be prepared by mixing granular starch in water. The temperature is raised to about 35° C. An aqueous solution of potassium permanganate is then added at a concentration of about 50 ppm based on starch. The pH is raised to about 11.5 with sodium hydroxide and the slurry is stirred sufficiently to prevent settling of the starch. Then, about a 30% solution of hydrogen peroxide diluted in water is added to a level of about 1% of peroxide based on starch. The pH of about 11.5 is then restored by adding additional sodium hydroxide. The reaction is completed over about a 1 to about 20 hour period. The mixture is then neutralized with dilute hydrochloric acid. The degraded starch is recovered by filtration followed by washing and drying.

The shampoo composition can comprise a cationic copolymer of an acrylamide monomer and a cationic monomer, wherein the copolymer has a charge density of from about 1.0 meq/g to about 3.0 meq/g. The cationic copolymer can be a synthetic cationic copolymer of acrylamide monomers and cationic monomers.

The cationic copolymer can comprise:
(i) an acrylamide monomer of the following Formula AM:

Formula AM where $R^9$ is H or $C_{1-4}$ alkyl; and $R^{10}$ and $R^{11}$ are independently selected from the group consisting of H, $C_{1-4}$ alkyl, $CH_2OCH_3$, $CH_2OCH_2CH(CH_3)_2$, and phenyl, or together are $C_{3-6}$cycloalkyl; and (ii) a cationic monomer conforming to Formula CM:

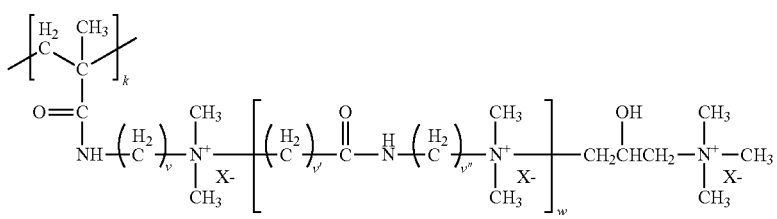

Formula CM where k=1, each of v, v', and v" is independently an integer of from 1 to 6, w is zero or an integer of from 1 to 10, and $X^-$ is an anion.

The cationic monomer can conform to Formula CM and where k=1, v=3 and w=0, z=1 and $X^-$ is $Cl^-$ to form the following structure:

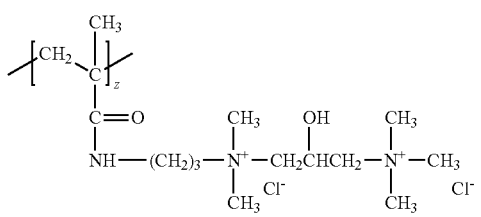

The above structure may be referred to as diquat. Alternatively, the cationic monomer can conform to Formula CM and wherein v and v" are each 3, v'=1, w=1, y=1 and $X^-$ is $Cl^-$, such as:

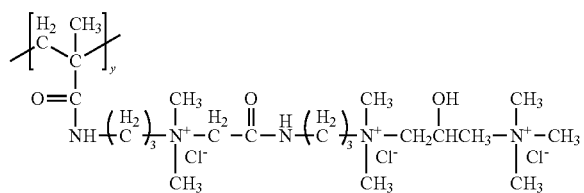

The above structure may be referred to as triquat.

Suitable acrylamide monomer can include, but are not limited to, either acrylamide or methacrylamide.

The cationic copolymer can be of an acrylamide monomer and a cationic monomer, wherein the cationic monomer is selected from the group consisting of: dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide; ethylenimine, vinylamine, 2-vinylpyridine, 4-vinylpyridine; trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride, and mixtures thereof.

The cationic copolymer can comprise a cationic monomer selected from the group consisting of: cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, and mixtures thereof.

The cationic copolymer can be water-soluble. The cationic copolymer is formed from (1) copolymers of (meth)acrylamide and cationic monomers based on (meth)acrylamide, and/or hydrolysis-stable cationic monomers, (2) terpolymers of (meth)acrylamide, monomers based on cationic (meth)acrylic acid esters, and monomers based on (meth)acrylamide, and/or hydrolysis-stable cationic monomers. Monomers based on cationic (meth)acrylic acid esters may be cationized esters of the (meth)acrylic acid containing a quaternized N atom. The cationized esters of the (meth)acrylic acid containing a quaternized N atom can be quaternized dialkylaminoalkyl (meth)acrylates with C1 to C3 in the alkyl and alkylene groups. Suitable cationized esters of the (meth)acrylic acid containing a quaternized N atom can be selected from the group consisting of: ammonium salts of dimethylaminomethyl (meth)acrylate, dimethylaminoethyl (meth)acrylate, dimethylaminopropyl (meth)acrylate, diethylaminomethyl (meth)acrylate, diethylaminoethyl (meth)acrylate; and diethylaminopropyl (meth)acrylate quaternized with methyl chloride. The cationized esters of the (meth)acrylic acid containing a quaternized N atom can be dimethylaminoethyl acrylate, which is quaternized with an alkyl halide, or with methyl chloride or benzyl chloride or dimethyl sulfate (ADAME-Quat). The cationic monomer when based on (meth)acrylamides can be quaternized dialkylaminoalkyl(meth)acrylamides with C1 to C3 in the alkyl and alkylene groups, or dimethylaminopropylacrylamide, which is quaternized with an alkyl halide, or methyl chloride or benzyl chloride or dimethyl sulfate.

Suitable cationic monomer based on a (meth)acrylamide include quaternized dialkylaminoalkyl(meth)acrylamide with C1 to C3 in the alkyl and alkylene groups. The cationic monomer based on a (meth)acrylamide can be dimethylaminopropylacrylamide, which is quaternized with an alkyl halide, especially methyl chloride or benzyl chloride or dimethyl sulfate.

The cationic monomer can be a hydrolysis-stable cationic monomer. Hydrolysis-stable cationic monomers can be, in addition to a dialkylaminoalkyl(meth)acrylamide, all monomers that can be regarded as stable to the OECD hydrolysis test. The cationic monomer can be hydrolysis-stable and the hydrolysis-stable cationic monomer can be selected from the group consisting of: diallyldimethylammonium chloride and water-soluble, cationic styrene derivatives.

The cationic copolymer can be a terpolymer of acrylamide, 2-dimethylammoniumethyl (meth)acrylate quaternized with methyl chloride (ADAME-Q) and 3-dimethylammoniumpropyl(meth)acrylamide quaternized with methyl chloride (DIMAPA-Q). The cationic copolymer can be formed from acrylamide and acrylamidopropyltrimethylammonium chloride, wherein the acrylamidopropyltrimethylammonium chloride has a charge density of from about 1.0 meq/g to about 3.0 meq/g.

The cationic copolymer can have a charge density of from about 1.1 meq/g to about 2.5 meq/g, or from about 1.1 meq/g to about 2.3 meq/g, or from about 1.2 meq/g to about 2.2 meq/g, or from about 1.2 meq/g to about 2.1 meq/g, or from about 1.3 meq/g to about 2.0 meq/g, or from about 1.3 meq/g to about 1.9 meq/g.

The cationic copolymer can have a weight average molecular weight from about 10 thousand g/mol to about 1 million g/mol, or from about 25 thousand g/mol to about 1 million g/mol, or from about 50 thousand g/mol to about 1 million g/mol, or from about 100 thousand g/mol to about 1.0 million g/mol, or from about 150 thousand g/mol to about 1.0 million g/mol.

Cationic Synthetic Polymers

The shampoo composition can comprise a cationic synthetic polymer that may be formed from
  i) one or more cationic monomer units, and optionally
  ii) one or more monomer units bearing a negative charge, and/or
  iii) a nonionic monomer,
wherein the subsequent charge of the copolymer is positive. The ratio of the three types of monomers is given by "m", "p" and "q" where "m" is the number of cationic monomers, "p" is the number of monomers bearing a negative charge and "q" is the number of nonionic monomers The cationic polymers can be water soluble or dispersible, non-crosslinked, and synthetic cationic polymers having the following structure:

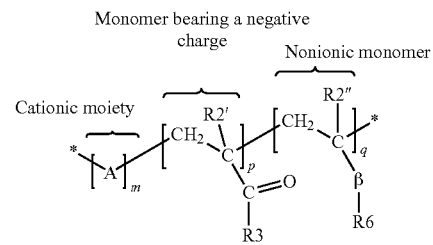

$m \geq 1$
$p = 0$ or $\geq 1$
$q = 0$ or $\geq 1$
$m \geq p$ where A, may be one or more of the following cationic moieties:

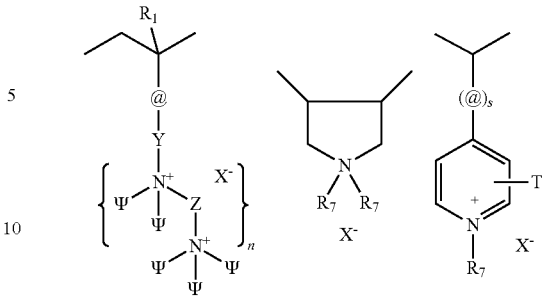

where @=amido, alkylamido, ester, ether, alkyl or alkylaryl;
where Y=C1-C22 alkyl, alkoxy, alkylidene, alkyl or aryloxy;
where ψ=C1-C22 alkyl, alkyloxy, alkyl aryl or alkyl arylox;
where Z=C1-C22 alkyl, alkyloxy, aryl or aryloxy;
where R1=H, C1-C4 linear or branched alkyl;
where s=0 or 1, n=0 or $\geq 1$;
where T and R7=C1-C22 alkyl; and
where X—=halogen, hydroxide, alkoxide, sulfate or alkylsulfate.

Where the monomer bearing a negative charge is defined by R2'=H, C1-C4 linear or branched alkyl and R3 as:

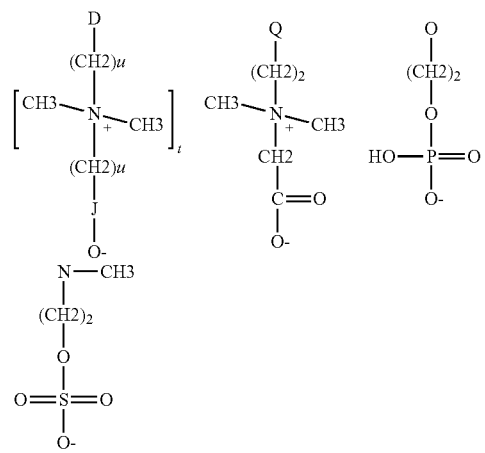

where D=O, N, or S;
where Q=NH$_2$ or O;
where u=1-6;
where t=0-1; and
where J=oxygenated functional group containing the following elements P, S, C.

Where the nonionic monomer is defined by R2"=H, C1-C4 linear or branched alkyl, R6=linear or branched alkyl, alkyl aryl, aryl oxy, alkyloxy, alkylaryl oxy and β is defined as

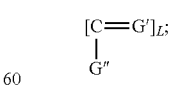

and
where G' and G" are, independently of one another, O, S or N—H and L=0 or 1.

Examples of cationic monomers include aminoalkyl (meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyldialkyl ammonium salts; their mixtures, their salts, and macromonomers deriving from therefrom.

Further examples of cationic monomers include dimethylaminoethyl (meth)acrylate, dimethylaminopropyl (meth)acrylate, ditertiobutylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine, trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride, diallyldimethyl ammonium chloride.

Suitable cationic monomers include those which comprise a quaternary ammonium group of formula —$NR_3^+$, wherein R, which is identical or different, represents a hydrogen atom, an alkyl group comprising 1 to 10 carbon atoms, or a benzyl group, optionally carrying a hydroxyl group, and comprise an anion (counter-ion). Examples of anions are halides such as chlorides, bromides, sulphates, hydrosulphates, alkylsulphates (for example comprising 1 to 6 carbon atoms), phosphates, citrates, formates, and acetates.

Suitable cationic monomers include trimethylammonium ethyl (meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl (meth)acrylamido chloride, trimethyl ammonium propyl (meth)acrylamido chloride, vinylbenzyl trimethyl ammonium chloride.

Additional suitable cationic monomers include trimethyl ammonium propyl (meth)acrylamido chloride.

Examples of monomers bearing a negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Suitable monomers with a negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Examples of nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide (meth)acrylate (i.e. polyethoxylated (meth) acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Suitable nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The anionic counterion (X—) in association with the synthetic cationic polymers may be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non-limiting examples of such counterions include halides (e.g., chlorine, fluorine, bromine, iodine), sulfate and methylsulfate.

The concentration of the cationic polymers ranges about 0.025% to about 5%, from about 0.1% to about 3%, and/or from about 0.2% to about 1%, by weight of the shampoo composition.

Suitable cationic cellulose polymers are salts of hydroxyethyl cellulose reacted with trimethyl ammonium substituted epoxide, referred to in the industry (CTFA) as Polyquaternium 10 and available from Dow/Amerchol Corp. (Edison, N.J., USA) in their Polymer LR, JR, and KG series of polymers. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24. These materials are available from Dow/Amerchol Corp. under the tradename Polymer LM-200. Other suitable types of cationic cellulose include the polymeric quaternary ammonium salts of hydroxyethyl cellulose reacted with lauryl dimethyl ammonium-substituted epoxide and trimethyl ammonium substituted epoxide referred to in the industry (CTFA) as Polyquaternium 67. These materials are available from Dow/Amerchol Corp. under the tradename SoftCAT Polymer SL-5, SoftCAT Polymer SL-30, Polymer SL-60, Polymer SL-100, Polymer SK-L, Polymer SK-M, Polymer SK-MH, and Polymer SK-H.

Anti-Dandruff Actives

Anti-dandruff agents suitable for use in foamed shampoo compositions include pyridinethione salts, azoles (e.g., ketoconazole, econazole, and elubiol), selenium sulfide, particulate sulfur, salicylic acid, and mixtures thereof. A typical anti-dandruff agent is pyridinethione salt. shampoo compositions can also include a zinc-containing layered material. An example of a zinc-containing layered material can include zinc carbonate materials. Of these, zinc carbonate and pyridinethione salts (particularly zinc pyridinethione or "ZPT) are common in the composition, and often present together.

Emulsifiers

A variety of anionic and nonionic emulsifiers can be used in the foamed shampoo compositions. The anionic and nonionic emulsifiers can be either monomeric or polymeric in nature. Monomeric examples include, by way of illustrating and not limitation, alkyl ethoxylates, alkyl sulfates, soaps, and fatty esters and their derivatives. Polymeric examples include, by way of illustrating and not limitation, polyacrylates, polyethylene glycols, and block copolymers and their derivatives. Naturally occurring emulsifiers such as lanolins, lecithin and lignin and their derivatives are also non-limiting examples of useful emulsifiers.

Chelating Agents

The foamed shampoo composition can also comprise a chelant. Suitable chelants include those listed in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference. When related to chelants, the term "salts and derivatives thereof" means the salts and derivatives comprising the same functional structure (e.g., same chemical backbone) as the chelant they are referring to and that have similar or better chelating properties. This term can include alkali metal, alkaline earth, ammonium, substituted ammonium (i.e. monoethanolammonium, diethanolammonium, triethanolammonium) salts, esters of chelants having an acidic moiety and mixtures thereof, in particular all sodium, potassium or ammonium salts. The term "derivatives" also includes "chelating surfactant" compounds, such as those exemplified in U.S. Pat. No. 5,284,972, and large molecules comprising one or more chelating groups having the same functional structure as the parent chelants, such as polymeric EDDS (ethylenediaminedisuccinic acid) disclosed in U.S. Pat. No. 5,747,440.

Levels of the EDDS chelant in the foamed shampoo compositions can be as low as about 0.01 wt % or even as high as about 10 wt %, but above the higher level (i.e., 10 wt %) formulation and/or human safety concerns may arise. The level of the EDDS chelant may be at least about 0.05 wt %, at least about 0.1 wt %, at least about 0.25 wt %, at least about 0.5 wt %, at least about 1 wt %, or at least about 2 wt % of the foamed shampoo composition. Levels above about 4 wt % can be used but may not result in additional benefit.

Aqueous Carrier

The foamed shampoo compositions can be in the form of pourable liquids (under ambient conditions). Such compositions will therefore typically comprise a carrier, which is present at a level of from about 40% to about 80%, alternatively from about 45% to about 75%, alternatively from about 50% to about 70%, by weight, of the foamed shampoo composition. The carrier may comprise water, or a miscible mixture of water and organic solvent, and in one aspect may comprise water with minimal or no significant concentrations of organic solvent, except as otherwise incidentally incorporated into the composition as minor ingredients of other essential or optional components.

Carriers useful in the foamed shampoo compositions include water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Dosage of Foam

The compact shampoo composition can be dispensed from a foamer, such as an aerosol or pump foamer, as a dosage of foam. The dosage of foam can have a volume of from about 5 cm$^3$ to about 500 cm$^3$, alternatively from about 5 cm$^3$ to about 450 cm$^3$, alternatively from about 10 cm$^3$ to about 400 cm$^3$, alternatively from about 10 cm$^3$ to about 350 cm$^3$, alternatively from about 10 cm$^3$ to about 300 cm$^3$, alternatively from about 20 cm$^3$ to about 250 cm$^3$, alternatively from about 20 cm$^3$ to about 200 cm$^3$, alternatively from about 20 cm$^3$ to about 150 cm$^3$, and alternatively from about 20 cm$^3$ to about 100 cm$^3$.

The dosage of foam can comprise from about 0.5 g to about 20 g, alternatively from about 0.5 g to about 18 g, alternatively from about 0.5 g to about 16 g, alternatively from about 0.5 g to about 15 g, alternatively from about 1 g to about 15 g, alternatively from about 1 g to about 15 g, alternatively from about 1 g to about 12 g, alternatively from about 2 g to about 12 g, alternatively from about 2 g to about 10 g, alternatively from about 2.5 g to about 10 g, alternatively from about 3 g to about 9 g, alternatively from about 3 g to about 8 g of a detersive surfactant by weight of the foam.

The dosage of foam can also comprise from about 0.0001 g to about 5 g, alternatively from about 0.001 g to about 5 g, alternatively from about 0.001 g to about 4 g, alternatively from about 0.01 g to about 4 g, alternatively from about 0.05 g to about 3 g, alternatively from about 0.1 to about 2 g, alternatively from about 0.075 g to about 2 g propellant, by weight of the foam, alternatively from about 0.05 g to about 1 g, and alternatively from about 0.05 g to about 0.5 g.

The dosage of foam can also have a foam density of from about 0.010 g/cm$^3$ to about 0.50 g/cm$^3$; alternatively from about 0.02 g/cm$^3$ to about 0.40 g/cm$^3$; and alternatively from about 0.03 g/cm$^3$ to about 0.35 g/cm$^3$.

The dosage of foam can also have a bubble size distribution comprising an $R_{32}$ of from about 1 μm to about 500 μm, alternatively from about 5 μm to about 300 μm, alternatively from about 10 μm to about 200 μm; and alternatively from about 20 μm to about 100 μm.

The dosage of foam can have a yield point of from about 5 Pa to about 100 Pa, alternatively from about 8 Pa to about 80 Pa, alternatively from about 8 Pa to about 60 Pa, and alternatively from about 10 Pa to about 50 Pa.

The dosage of foam can comprise from about 0.00005 g to about 0.5 g of a cationic deposition polymer by weight of the foam.

Foam Dispenser

Figure 3:
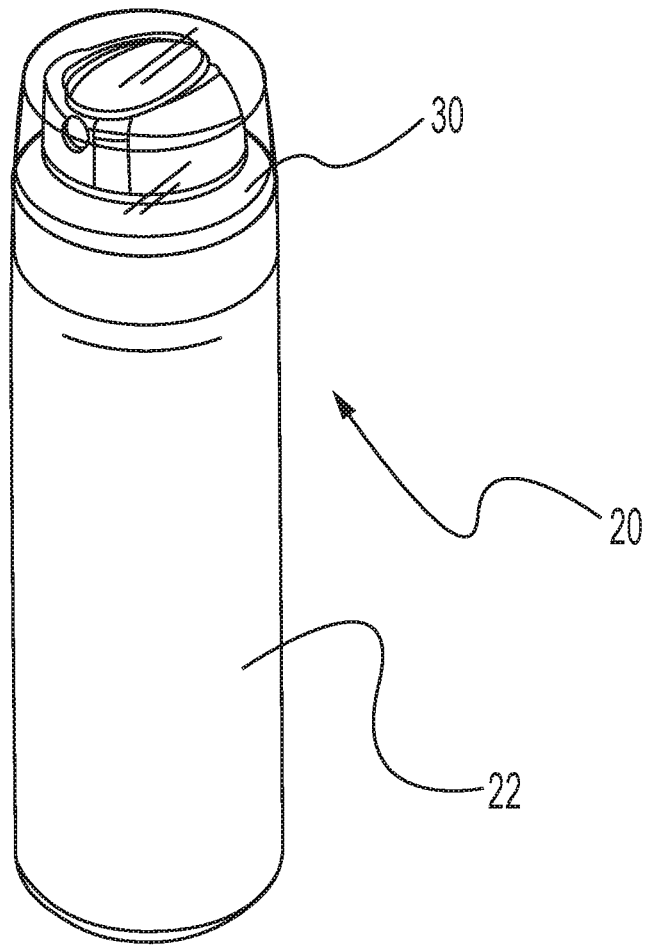
FIG. 3 is a perspective view of an aerosol dispenser according to the present invention having a plastic outer container and a bag.
Figures 4A, 4B:
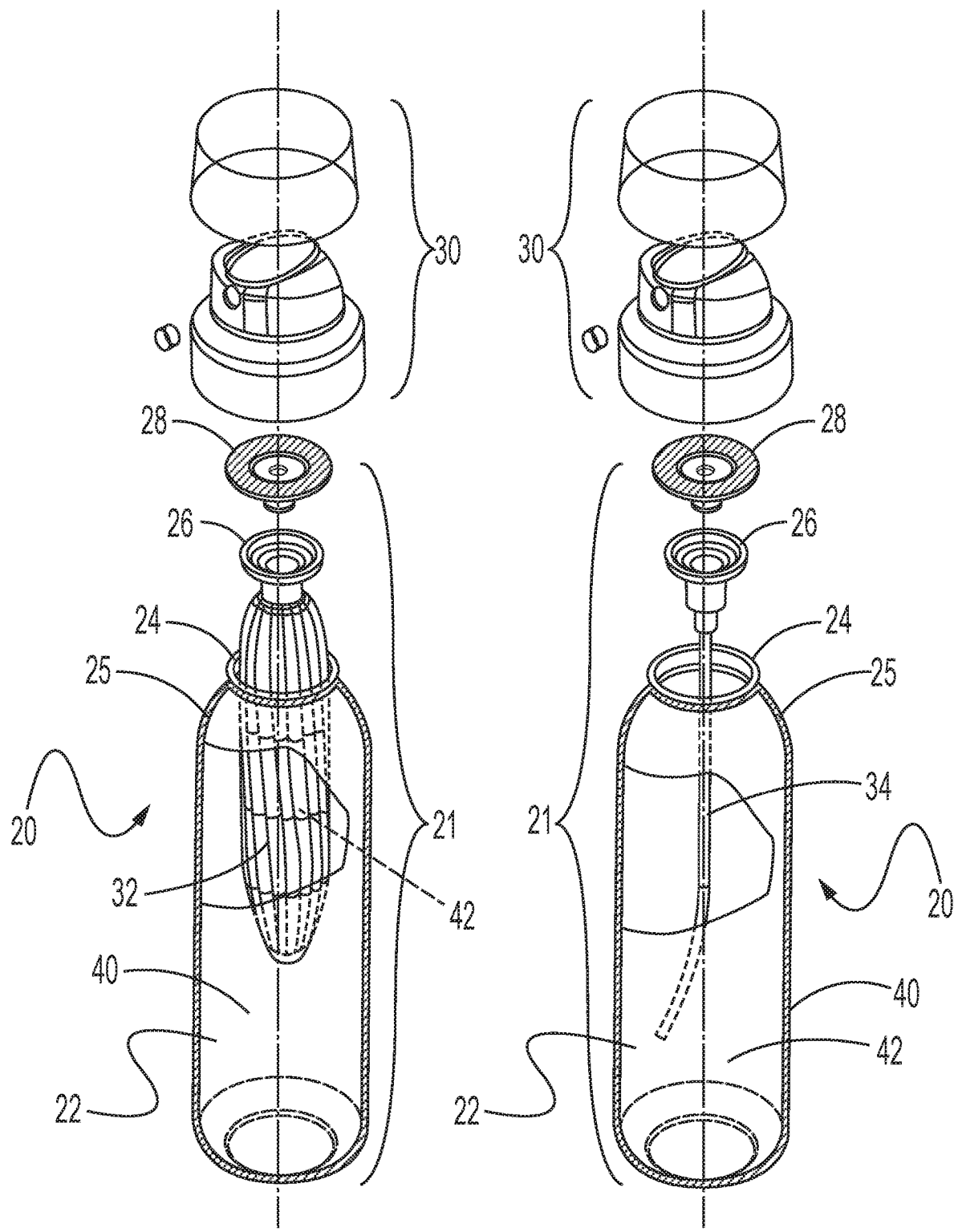
FIG. 4A is an exploded perspective view of the aerosol dispenser of FIG. 1 having a collapsible bag.
FIG. 4B is an exploded perspective view of the aerosol dispenser of FIG. 1 having a dip tube.

Referring to FIGS. 3, 4A, and 4B, an aerosol dispenser 20 is shown. The dispenser 20 comprises a pressurizeable outer container 22. The outer container 22 can comprise any suitable material, including plastic or metal. The outer container 22 may have an opening. The opening defines a neck 24, to which other components may be sealed. The neck 24 may be connected to the container sidewall by a shoulder 25.

Referring to FIGS. 4A and 4B, a valve cup 26 may be sealed to the opening of the outer container 22. The seal, outer container and other container components can be selected to be resistant to the shampoo composition 42 and/or propellant 40.

A valve assembly 28, in turn, may be disposed within the valve cup 26. The valve assembly 28 provides for retention of shampoo composition 42 within the aerosol dispenser 20 until the shampoo composition 42 is selectively dispensed by a user. The valve assembly 28 may be selectively actuated by an actuator 30. Selective actuation of the valve assembly 28 allows the user to dispense a desired quantity of the shampoo composition 42 on demand. The shampoo composition can be dispensed as a foam.

Inside the outer container 22 may be a product delivery device. The product delivery device may comprise a collapsible bag 32 which can be made of gas impermeable material as shown in FIG. 4A. The collapsible bag 32 may be mounted in a sealing relationship to the neck 24 of the container (i.e. a bag-on-can arrangement). Alternative the collapsible bag 32 may be mounted in sealing relationship to the valve assembly 28 (i.e. a bag-on-valve arrangement).

The collapsible bag 32 may hold shampoo composition 42 therein and prevent intermixing of such shampoo composition 42 with propellant 40, which can also be referred to as driving gas. The propellant 40 may be stored outside the collapsible bag 32, and inside the outer container 22. The propellant may be any gas as long as it does not excessively penetrate the walls of the collapsible bag 32 or outer container 22 thus maintaining the performance of the product and dispensing acceptable during its usable life.

The shampoo composition 42 may include a propellant, which can also be referred to as a foaming or blooming agent. If a blooming agent is used with the composition 42, the pressure in the outer container 22 can be greater than the vapor pressure of the blooming agent, so that shampoo composition 42 may be dispensed from within the bag.

After the collapsible bag has been filled with the composition, the outer container may be pressurized from about 40 to about 160 psig, from about 50 to about 140 psig, from about 60 to about 90 psig (all measured at RT). In any case, the equilibrium pressure measured at a certain temperature cannot exceed the maximum allowable pressure of the container per the applicable local transport and safety regulations.

The product delivery device may alternatively or additionally comprise a dip tube 34 as shown in FIG. 4B. The dip tube 34 extends from a proximal end sealed to the valve assembly 28. The dip tube 34 may terminate at a distal end juxtaposed with the bottom of the outer container 22. The shampoo composition 42 and propellant 40 can intermix. The propellant 40 also accomplish the function of blooming agent. Both are co-dispensed in response to selective actuation of the valve assembly 28 by a user.

The product delivery device may be an aerosol pump dispenser and may not contain a dip tube or a collapsible bag, for instance, an inverted aerosol container.

The pressure of the propellant 40 within the outer container 22 provides for dispensing of the shampoo composition 42/co-dispensing of shampoo composition 42/propellant 40 to ambient, and optionally to a target surface. The target surface may include a surface to be cleaned or treated by the shampoo composition 42, hair, scalp, etc. Such dispensing occurs in response to the user actuating the valve assembly 28.

The outer container may be pressurized from about 20 to about 110 psig, more preferably from about 30 to about 90 psig, still more preferably from about 40 to about 70 psig (all measured after filling to the intended level at RT). In any case, the equilibrium pressure measured at a certain temperature cannot exceed the maximum allowable pressure of the container per the applicable local transport and safety regulations.

Referring to FIGS. 4A and 4B, the aerosol dispensers 20, and components thereof, may have a longitudinal axis, and may be axi-symmetric and can have a round cross section. Alternatively, the outer container 22, may be eccentric and may have a square, elliptical or other cross section. The outer container 22 and aerosol dispenser 20 may be nonrefillable and may be permanently sealed to prevent reuse without destruction and/or gross deformation of the aerosol dispenser 20. If desired, the outer container 22, collapsible bag 32, and/or dip tube 34, may be transparent or substantially transparent. If the outer container 22 and collapsible bag 32 (if present) are transparent, this arrangement can provide the benefit that the consumer knows when shampoo composition 42 is nearing depletion and allows improved communication of shampoo composition 42 attributes, such as color, viscosity, stability, etc. Alternatively or additionally, the outer container 22 and/or collapsible bag 32, etc. may be transparent and colored with like or different colors.

Alternatively, the hair composition can be stored and dispensed from a mechanical foam dispenser. Non-limiting examples of suitable pump dispensers include those described in WO 2004/078903, WO 2004/078901, and WO 2005/078063 and may be supplied by Albea (60 Electric Ave., Thomaston, Conn. 06787 USA) or Rieke Packaging Systems (500 West Seventh St., Auburn, Ind. 46706). The composition can be substantially free of propellant.

Alternatively, the composition can be stored and dispensed from a squeeze foam dispenser. An example of squeeze foamer is EZ'R available from Albéa.

Foaming Agent

The shampoo composition described herein may comprise from about from about 3% to about 20% propellant or foaming agent, alternatively from about 3% to about 18% propellant or foaming agent, alternatively from about 3% to about 15% propellant or foaming agent, alternatively from about 3% to about 12% propellant or foaming agent, alternatively from about 4% to about 10% propellant or foaming agent, and alternatively from about 5% to about 8% propellant or foaming agent, by weight of the shampoo composition.

A propellant or foaming agent can be added to the shampoo composition described herein at a composition to propellant weight ratio of from about 3:17 to about 49:1; alternatively from about 9:1 to about 97:3; and alternatively from about 23:2 to about 24:1 to create a pressurized composition.

Trans-1,3,3,3-tetrafluoroprop-1-ene ("HFO") (Solstice® Propellant HFO-1234ze available by Honeywell) can be used as a foaming agent within shampoo formulations.

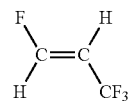

When used as a foaming agent Trans-1,3,3,3-tetrafluoroprop-1-ene has been found to have unique advantages over the use of low vapor pressure hydrocarbon foaming agents (such as commonly used A46 which is a mixture of 84.8% isobutane and 15.2% propane) in that it enables significantly higher foam densities (approximately 2× greater) versus hydrobarbon propellants and at equal formula pressure and formula % saturated pressure. The higher density enables higher gravimetric foam dosage per unit volume of the resulting dispensed foam shampoo and making it easier to achieve sufficient dosage from a low-density foam shampoo form relative to a high density liquid shampoo form. The pressure and % saturated pressure is important to enable sufficient foam dispensing over the life of the product (from beginning to middle to end of the pressurized container). The Trans-1,3,3,3-tetrafluoroprop-1-ene has been found to result in gloss or shine of the dispensed foam.

The foaming agent/propellant for use in the shampoo composition described herein can be selected from the group consisting of hydrofluoroolefins (HFOs) such as cis- and/or trans-1,3,3,3-tetrafluoropropene (HFO-1234ze), particularly the trans isomer, 3,3,3-trifluoropropene (HFO-1243zf), 2,3,3,3-tetrafluoropropene (HFO 1234yf), 1,2,3,3,3-pentafluoropropene (HFO-1225ye), and mixtures thereof.

The foaming agent/propellant for use in the shampoo composition described herein can be selected from the group consisting of halogenated alkenes of generic formula that would include numerous HFOs and HCFOs. In addition, the foaming agent/propellants listed can be mixed with one or more hydrofluoroolefins, hydrochlorofluoroolefins, hydrofluorocarbons, chlorofluorocarbons, hydrocarbons, alkyl ethers, and compressed gases.

The foaming agent/propellant for use in the shampoo composition described herein can be selected from the group consisting of halogenated alkenes of generic formula that would include numerous HFOs and HCFOs. In addition, the foaming agent/propellants listed can be mixed with one or more hydrofluoroolefins, hydrochlorofluoroolefins, hydrofluorocarbons, chlorofluorocarbons, hydrocarbons, alkyl ethers, and compressed gases.

The foaming agent/propellant for use in the shampoo composition described herein can be selected from the group consisting of hydrochlorofluoroolefins (HCFOs) such as cis and/or trans-1-chloro-3,3,3-trifluoropropene (HCFO-1233zd), particularly the trans isomer, 2-chloro-3,3,3-trifluoropropene (HCFO-1233xf), 1,1-dicloro-3,3,3-trifluoropropene, 1,2-dichloro-3,3,3-trifluoropropene, and mixtures thereof.

The foaming agent/propellant for use in the shampoo composition described herein can be selected from the group consisting of chlorofluorocarbons (CFCs) such as dichlorodifluoromethane, 1,1-dichloro-1,1,2,2-tetrafluoroethane, 1-chloro-1,1-difluoro-2,2-trifluoroethane, 1-chloro-1,1-difluoroethylene, monochlorodifluoromethane and mixtures thereof; The foaming agent/propellant suitable for use in the shampoo composition can be selected from the group consisting of chemically-inert hydrocarbons such as propane, n-butane, isobutane, n-pentane, isopentane, and mixtures thereof; compressed gases such as carbon dioxide, nitrous oxide, nitrogen, compressed air, and mixtures thereof; and mixtures of one or more hydrocarbons and compressed gases. In an embodiment, the foaming agent can comprise a blend of hydrocarbons such as isobutane, propane, and butane including, but not limited to, hydrocarbon blend A-46 (15.2% propane, 84.8% isobutane), hydrocarbon blend NP-46 (25.9% propane, 74.1% n-butane), hydrocarbon blend NIP-46 (21.9% propane, 31.3% isobutane, 46.8% n-butane), and other non-limiting hydrocarbon blends designated as A-31, NP-31, NIP-31, A-70, NP-70, NIP-70, A-85, NP-85, A-108. In an embodiment, the foaming agent can include compressed gases including, but not limited to, carbon dioxide and nitrous oxide.

The foaming agent for use in the shampoo composition can be the hydrocarbon blend A-46 (15.2% propane, 84.8% isobutane).

Perfume

The shampoo composition may comprise from about 0.5% to about 7%, alternatively from about 1% to about 6%, and alternatively from about 2% to about 5% perfume, by weight of the shampoo composition.

The shampoo composition may have a silicone to perfume ratio of from 1:1 to about 19:1, alternatively from about 3:2 to about 9:1, alternatively from about 7:3 to about 17:3.

Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the shampoo composition.

Method of Treating Hair

The method of treating the hair described herein comprises (1) wetting the hair; (2) providing a shampoo composition, as described herein, (3) dispensing the shampoo composition as a liquid form or a foam form, where the foam form is dispensed from a mechanical foam dispenser or an aerosol dispenser; (4) applying the composition to the wet hair; (5) massaging the shampoo composition into wet hair and optionally forming a lather; (5) rinsing the composition from the hair; and (5) optionally repeating steps (2)-(4); and (6) optionally applying a conditioning composition where the conditioning composition can be liquid or can be dispensed as a foam from an mechanical foam dispenser or an aerosol dispenser and the conditioning composition can contain the silicone described herein.

Examples

The following examples illustrate the shampoo composition described herein. The exemplified compositions can be prepared by conventional formulation and mixing techniques. Before combining with the other ingredients in the shampoo chassis, the silicone is emulsified to form a silicone emulsion.

It will be appreciated that other modifications of the present invention within the skill of those in the shampoo formulation art can be undertaken without departing from the spirit and scope of this invention. All parts, percentages, and ratios herein are by weight unless otherwise specified. Some components may come from suppliers as dilute solutions. The amount stated reflects the weight percent of the active material, unless otherwise specified.

The following are non-limiting examples of the shampoo composition described herein.

Silicone a and b, used in the micoremulsions in the examples in the Tables, below, have the specific silicone structure in the examples corresponds to (Ia) below:

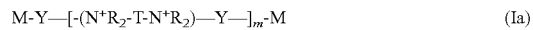

$$M-Y-[-(N^+R_2-T-N^+R_2)-Y-]_m-M \qquad (Ia)$$

with the following values:

m is about 2,

M represents a terminal group, comprising terminal ester groups selected from

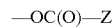

—OC(O)—Z wherein Z is a monovalent organic residues having about 11 carbon atoms (lauric ester).

Y is a combination of groups of the formula:

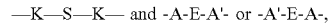

—K—S—K— and -A-E-A'- or -A'-E-A-, with S=

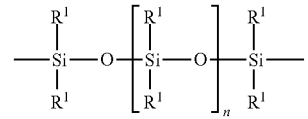

wherein $R^1$=methyl;

for Silicone a n=140 to 150 for an average chain length of 145;

for Silicone b n=105 to 115 for an average chain length of 110;

K is a bivalent straight chain, substituted with —OH,

A and A' each are acetic ester groups —OC(O)—CH$_2$— or —CH$_2$—C(O)O—

E is a polyethylene oxide group of the general formula:

—[CH$_2$CH$_2$O]$_q$—[CH$_2$CH(CH$_3$)O]$_r$—[CH$_2$CH(C$_2$H$_5$)O]$_s$— wherein q=2, r=–0, and s=0

T is a divalent organic group having about 6 carbon atoms.

The molar ratio of silicone to alkylene oxide block for Silicone a and b is 9:1. The viscosity of Silicone a is 10,100 cP and the viscosity of Silicone b is 15,400 cP (Brookfield Sp. 4, 12RPM, 22° C.). The nitrogen content for Silicone a is 0.19 mmol N/g polymer and the nitrogen content for Silicone B is 0.24 mmol N/g polymer.

Table 2 includes silicone emulsions that were used in the shampoo compositions in Table 3, Table 8, and Table 13.

TABLE 2

Silicone Emulsions

| | | Emulsion 3 (wt. %) | Emulsion 4 (wt. %) | Emulsion 5 (wt. %) | Emulsion 6 (wt. %) |
|---|---|---|---|---|---|
| Emulsifiers | Silicone a[1] | 35 | 35 | 35 | 27.89 |
| | Laureth-9 | 11.69 | 9.34 | 7.01 | — |
| | C11-15 Pareth-7 | — | — | — | 2.79 |
| | Ceteareth-25 | — | — | — | 6 |
| | Trideceth-3 | 5.81 | 4.65 | 3.49 | 5.16 |
| | Glycerin | 1.75 | 1.75 | 1.75 | 4.18 |
| | Water | Q.S. | Q.S. | Q.S. | Q.S. |
| | Ratio of Emulsifier: Silicone | 0.5 | 0.4 | 0.3 | 0.5 |
| | HLB of the Emulsifiers | 0.5 | 0.5 | 0.3 | 0.5 |
| | Clarity (time = 0) | Clear | Clear | Clear | Clear |
| | Clarity (time = 3 mos.) | Clear | Clear | Translucent | Clear |

[1]Silicone a = Experimental silicone polymer, according to the structure described herein, containing polyorganosiloxane compounds where the silicone blocks contain an average of 145 repeating siloxane units.

To make a clear shampoo composition, the silicone emulsion can be clear, and the silicone emulsion can maintain its clarity after being incorporated into a shampoo composition. The more hydrophobic silicones, such as terminal amino silicones (TAS) and Silicone Quaternium-26 (PQAS, available from Momentive™) are too hydrophobic to make clear nanoemulsions. Some of the existing clear nanoemulsions in the market such as Silsoft™ Q (Aqua (and) Silicone Quaternium-18 (and) Trideceth-6 (and) Trideceth-12, available from Momentive™) are very hydrophilic and may not capable of providing enough conditioning benefit to the hair.

The HLB (hydrophilic-lipophilic balance) of a surfactant, for instance an emulsifier, is a measure of the degree to which it is hydrophilic or lipophilic. This value indicates the hydrophylic-lipophylic balance of a molecule and is calculated theoretically:

Ethoxylated fatty alcohols $$HLB = 20 \times \left( \frac{\text{Molecular weight of Hydrophilic part}}{\text{Molecular weight of molecule}} \right)$$

The HLB for the emulsifiers can be from about 10 to about 11.5, alternatively from about 10.3 to about 11.

In Table 1, clarity was determined by visual inspection (i.e. if a label could be read through the emulsion then it was visually clear). It was found that the ratio of emulsifier to silicone was important to the clarity of the silicone emulsion. Emulsions 3, 4, and 6 were clear after being stored for three months in a closed 100 g polyethylene terephthalate (PET) container at approximately ambient conditions (20-25° C. at 60% relative humidity). However, Emulsion 5 was transparent after being stored for three months at the same conditions. Since Emulsion 5 is transparent after 3 months, it may not be used in clear shampoo formulations. Emulsion 5 had a lower ratio of emulsifier to silicone (0.3), as compared to Emulsions 3, 4, and 6 (with ratios of 0.5, 0.4, and 0.5 respectively).

Silicone emulsions used in clear shampoo formulations can have an emulsifier to silicone ratio greater than or equal to 0.3, alternatively greater than or equal to 0.35, alternatively greater than or equal to 0.4. Silicone emulsions used in clear shampoo formulations can have an emulsifier to silicone ratio from about 0.32 to about 1, alternatively from about 0.35 to about 0.8, alternatively from about 0.37 to about 0.7, alternatively from about 0.38 to about 0.65, and alternatively from about 0.4 to about 0.6.

Table 3 has opaque shampoos with different silicone emulsions. Examples A-1, A-2, A-4, and A-6 have 1% silicone. Examples A-1 and A-2 use silicone emulsions that are in current clear products and Examples A-4 and A-6 use emulsions with experimental silicones.

TABLE 3

Translucent Shampoo Examples

| | Ex. A-1 (wt. %) | Ex. A-2 (wt. %) | Ex. A-4 (wt. %) | Ex. A-6 (wt. %) |
|---|---|---|---|---|
| Sodium Laureth Sulfate[1] | 15 | 15 | 15 | 15 |
| Cocamidopropyl Betaine[2] | 2 | 2 | 2 | 2 |
| Guar Hydroxypropyltrimonium Chloride[3] | 0.15 | 0.15 | 0.15 | 0.15 |
| Polyquaternium-6[4] | 0.1 | 0.1 | 0.1 | 0.1 |
| Cetyl Alcohol | 0.179 | 0.179 | 0.179 | 0.179 |
| Stearyl Alcohol | 0.322 | 0.322 | 0.322 | 0.322 |
| Perfume | 0.8 | 0.8 | 0.8 | 0.8 |
| Preservative | 0.443 | 0.443 | 0.443 | 0.443 |
| pH adjuster | 0-0.30 | 0-0.30 | 0-0.30 | 0-0.30 |
| Thickener | 0-2 | 0-2 | 0-2 | 0-2 |
| DC 1872[5] | 4.55 | — | — | — |
| Belsil DM5500[6] | — | 2.38 | — | — |
| Emulsion 4 | — | — | 2.86 | — |
| Emulsion 6 | — | — | — | 3.58 |
| Water | Q.S. | Q.S. | Q.S. | Q.S. |

[1]Sodium Laureth 1 Sulfate, 26% active, supplied by Procter & Gamble MFG Co., Kansas City, USA
[2]Cocamidopropyl Betaine High pH at 30% active, from BASF ®
[3]N-Hance ™ 3196, MW of 1.7 million, from Ashland ™
[4]Polyquaternium 6, PolyDADMAC, MW of 150,000, CD of 6.2, trade name. Mirapol ® 100 s, 31.5% active, from Solvay
[5]DC 1872 silicone emulsion (dimethiconol) with an average particle size of 30 nm, from Dow Corning ®
[6]Belsil DM5500 polysiloxane emulsion, with an average particle size from about 100-150 nm, from Wacker ®

Examples A-1, A-2, A-4, and A-6 were evaluated for wet conditioning, dry conditioning, and silicone deposition on general population hair. Wet conditioning is evaluated by determining the wet feel (final rinse friction) and wet combing (Instrom Triple Comb (ITC)) and the dry conditioning is evaluated by determining the dry feel (Inter Fiber Friction (IFF)). Each test was repeated four times and the mean was calculated. The results of these tests are in Table 4 to Table 7, below, and FIGS. 1A-1D.

Table 4 and FIG. 1A compare the final rinse friction of Examples A-1, A-2, A-4, and A-6. The final rinse friction is determined by the Hair Wet Feel Friction Measurement Test Method, described herein.

TABLE 4

Hair Wet Feel Friction Measurement (Final Rinse Friction)

| Examples | Mean (gf) | Standard Deviation |
|---|---|---|
| Ex. A-2 | 1205 | +/−37 |
| Ex. A-4 | 1146 | +/−60 |
| Ex. A-6 | 1264 | +/−64 |
| Ex. A-1 | 1205 | +/−89 |

Figure 1B:
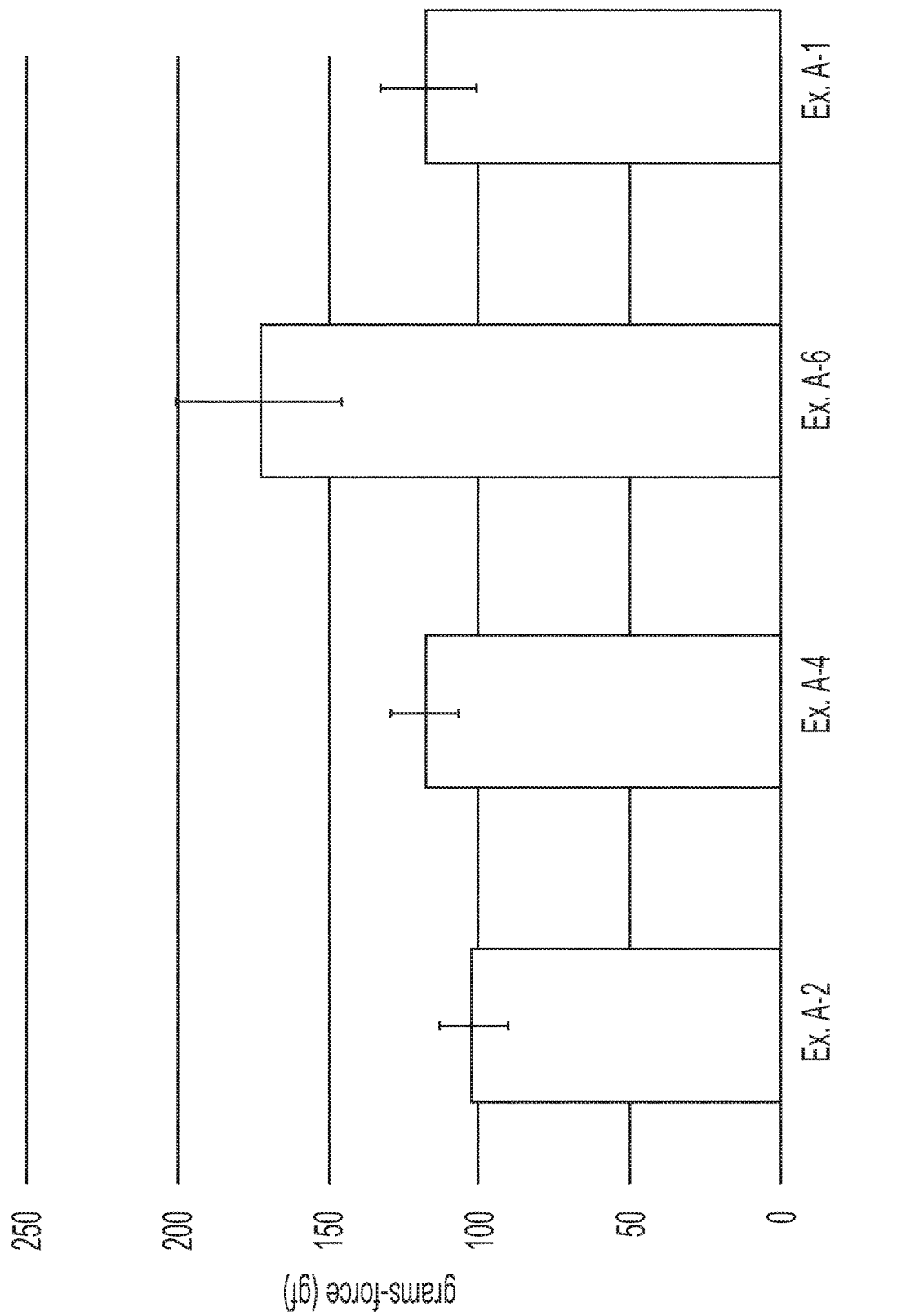
FIG. 1B compares the hair wet combing of Examples A-1, A-2, A-4, and A-6.

Table 5 and FIG. 1B compare the hair wet combing of Examples A-1, A-2, A-4, and A-6. The hair wet combing is determined by the Hair Wet Combing Test Method and determining the average Coarse Stroke 1, described herein.

TABLE 5

Hair Wet Combing (Instrom Triple Comb (ITC))

| Example | Mean (gf) | Standard Deviation |
|---|---|---|
| Ex. A-2 | 103 | +/−10 |
| Ex. A-4 | 137 | +/−5.0 |
| Ex. A-6 | 124 | +/−16 |
| Ex. A-1 | 129 | +/−17 |

Figure 1C:
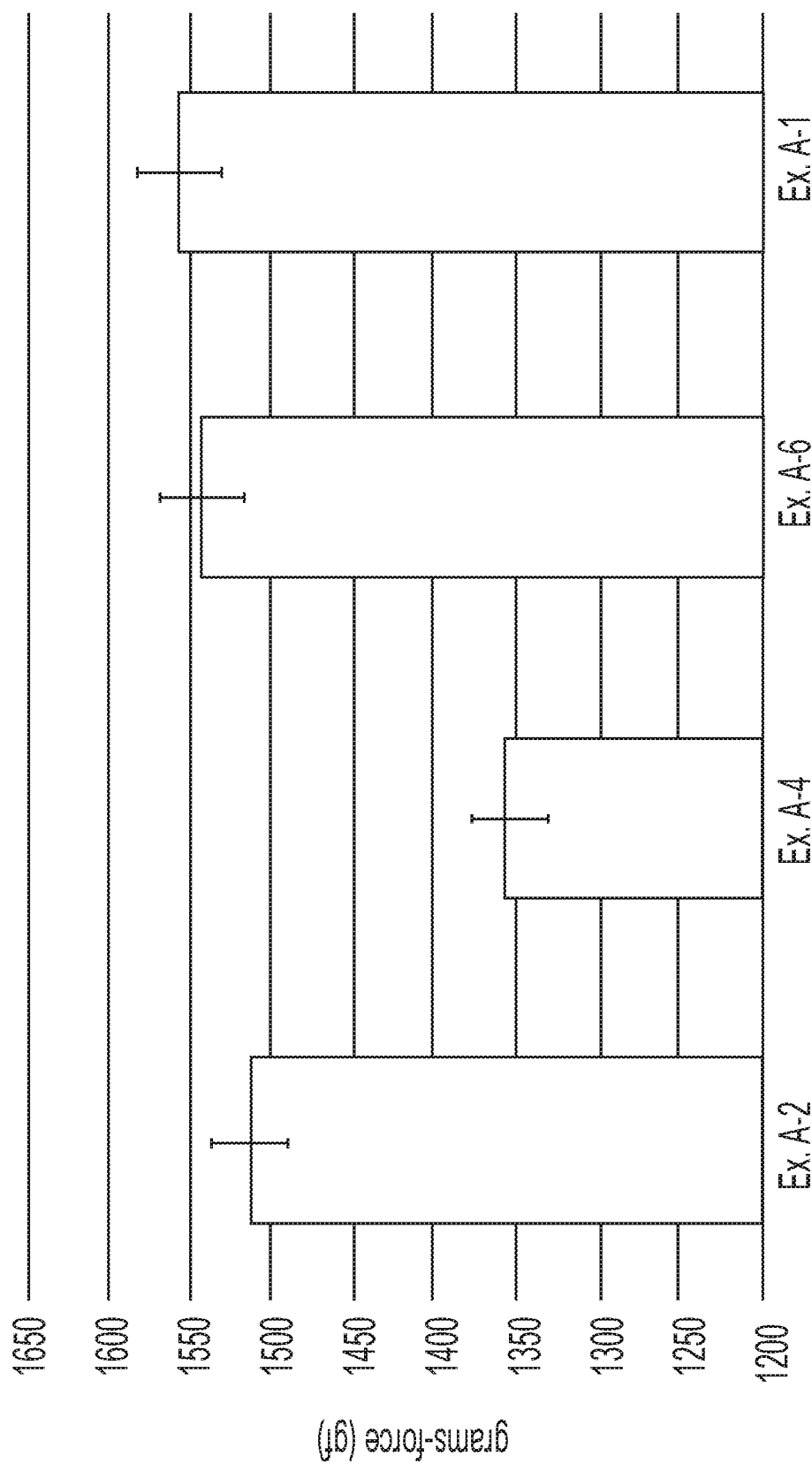
FIG. 1C compares the dry feel of Examples A-1, A-2, A-4, and A-6.

Table 6 and FIG. 1C compare the dry feel of Examples A-1, A-2, A-4, and A-6. The hair dry feel is determined by the Dry Feel Test Method, described herein.

TABLE 6

Dry Feel (Inter Fiber Friction (IFF))

| Example | Mean (gf) | Standard Deviation |
|---|---|---|
| Ex. A-2 | 1516 | +/−23 |
| Ex. A-4 | 1360 | +/−18 |
| Ex. A-6 | 1546 | +/−23 |
| Ex. A-1 | 1558 | +/−25 |

Figure 1D:
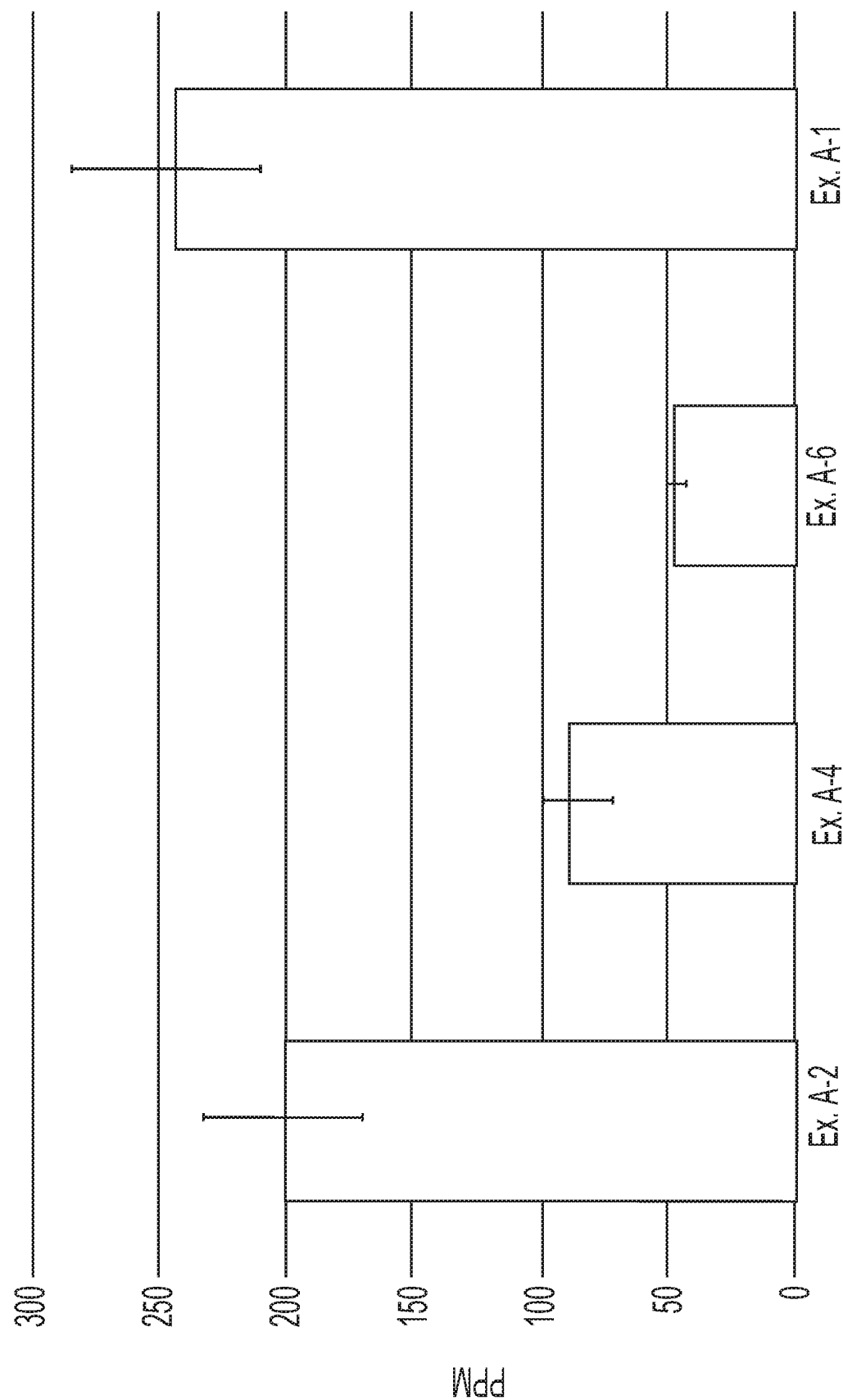
FIG. 1D compares the silicone deposition of Examples A-1, A-2, A-4, and A-6.

Table 7 and FIG. 1D compare the silicone deposition of Examples A-1, A-2, A-4, and A-6. The silicone deposition is determined by the Silicone Deposition Test Method, described herein.

TABLE 7

Silicone Deposition

| Example | Mean (ppm) | Standard Deviation |
|---|---|---|
| Ex. A-2 | 201 | +/−31 |
| Ex. A-4 | 88.8 | +/−10.2 |
| Ex. A-6 | 47.4 | +/−3.0 |
| Ex. A-1 | 243 | +/−41 |

Ex. A-1 and A-2 have silicone emulsions that are used in current shampoo formulations and have wet fee and dry feel that is consumer acceptable. As shown in Table 4, Table 5, and Table 6 and FIGS. 1A, 1B, and 1C, the performance of Ex. A-4 is approximately parity to the wet conditioning of Ex. A-1 and A-2 and Ex. A-4 performs better on dry feel than Ex. A-1 and A-2. Interestingly, Ex. A-4 has significantly less silicone deposition than Ex. A-1 and Ex. A-2. Some consumers, especially those who desire a fresh feel and lots of volume, like a conditioning feel but do not want too many silicone deposits, which they may perceive as not clean feeling, or they may perceive that a heavy silicone coating weighs down their hair.

Ex. A-6 may also be acceptable to consumers. The dry feel is parity to the dry feel of Ex. A-1 and A-2 and it has very low silicone deposition in this chassis, which consumers may prefer if they do not like the coated feel or buildup of silicone.

Table 8 has opaque shampoos with different silicone emulsions. Examples B to F have 1% silicone. Example B uses a silicone emulsion that is in current clear shampoo compositions and Example G was made without silicone.

TABLE 8

Clear Shampoo Compositions

| | Ex. B (wt. %) | Ex. C (wt. %) | Ex. D (wt. %) | Ex. E (wt. %) | Ex. F (wt. %) | Ex. G (wt. %) |
|---|---|---|---|---|---|---|
| Sodium Laureth Sulfate[1] | 15 | 15 | 15 | 15 | 15 | 15 |
| Cocamidopropyl Betaine[2] | 2 | 2 | 2 | 2 | 2 | 2 |
| Guar Hydroxypropyltrimonium Chloride[3] | 0.15 | 0.15 | 0.15 | 0.15 | 0.15 | 0.15 |
| Polyquaternium-10[4] | 0.15 | 0.15 | 0.15 | 0.15 | 0.15 | 0.15 |
| Perfume | 0.65 | 0.65 | 0.65 | 0.65 | 0.65 | 0.65 |
| Preservative | 0.44 | 0.44 | 0.44 | 0.44 | 0.44 | 0.44 |
| pH Adjuster | 0-0.30 | 0-0.30 | 0-0.30 | 0-0.30 | 0-0.30 | 0-0.30 |
| Thickener | 0-2 | 0-2 | 0-2 | 0-2 | 0-2 | 0-2 |
| DC 1872[5] | 4.55 | — | — | — | — | — |
| Emulsion 3 | — | 2.86 | — | — | — | — |
| Emulsion 4 | — | — | 2.86 | — | — | — |
| Emulsion 5 | — | — | — | 2.86 | — | — |
| Emulsion 6 | — | — | — | — | 3.58 | — |

[1] Sodium Laureth 1 Sulfate, 26% active, supplied by Procter & Gamble MFG Co., Kansas City, USA
[2] Cocamidopropyl Betaine High pH at 30% active, from BASF ®
[3] Jaguar ® Excel, with an average molecule weight of 1.2 million, available from Solvay
[4] UCare ™ Polymer LR-30M, MW 1.8 million, available from Dow ® Chemical Company
[5] DC 1872 silicone emulsion (dimethiconol) with an average particle size of 30 nm, from Dow Corning ®

Examples B to G were evaluated for wet conditioning and dry conditioning on general population hair. Each test was repeated four times and the mean was calculated. The results of these tests are in Table 9 to Table 11, below, and FIGS. 2A-2C.

Figure 2A:
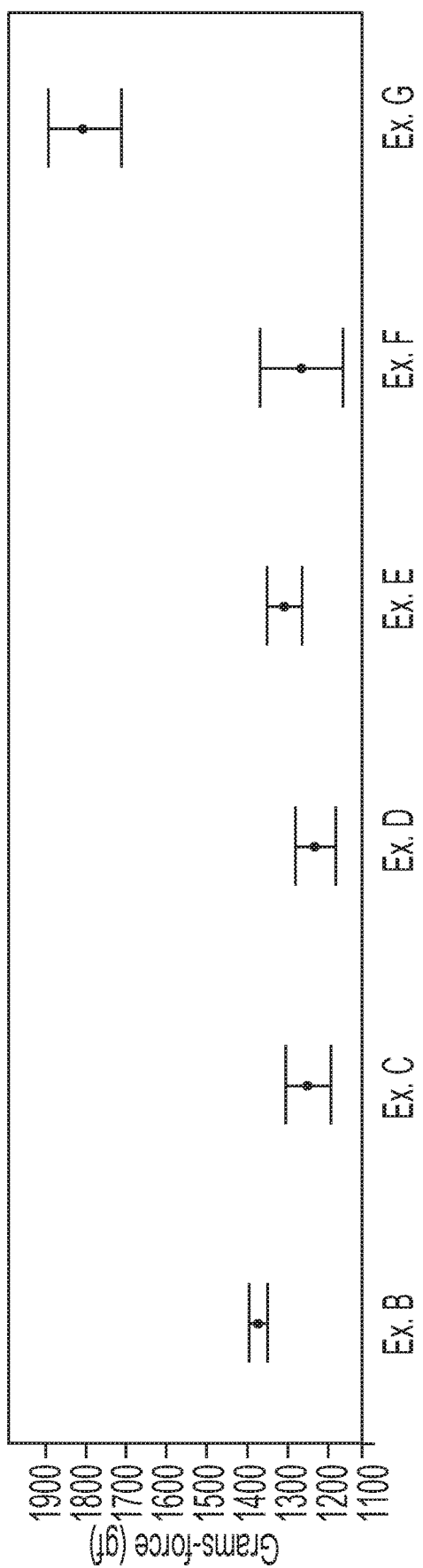
FIG. 2A compares the final rinse friction of Examples B to G.

Table 9 and FIG. 2A compare the final rinse friction of Examples B to G. The final rinse friction is determined by the Hair Wet Feel Friction Measurement Test Method, described herein.

TABLE 9

Hair Wet Feel Friction Measurement (Final Rinse Friction)

| Example | Mean (gf) | Standard Deviation |
|---|---|---|
| Ex. B | 1367 | +/−22.9 |
| Ex. C | 1241 | +/−54.8 |
| Ex. D | 1223 | +/−49.8 |
| Ex. E | 1300 | +/−42.3 |
| Ex. F | 1256 | +/−106 |
| Ex. G | 1802 | +/−92.9 |

Figure 2B:
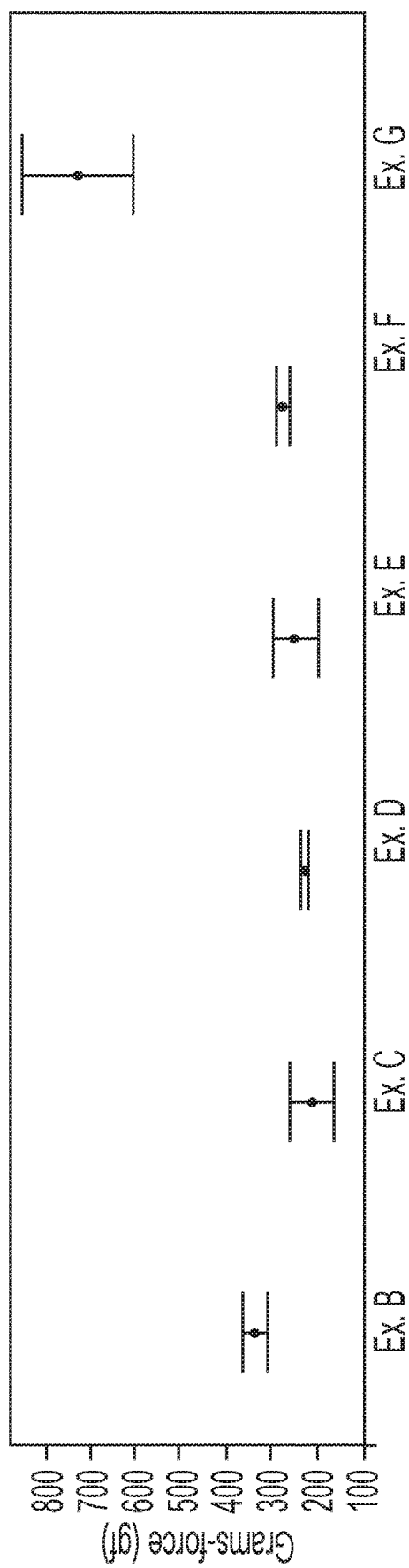
FIG. 2B compares the hair wet combing of Examples B to G.

Table 10 and FIG. 2B compare the hair wet combing by measuring the mean Coarse Stroke 1 of Examples B to G, as determined by the Hair Wet Combing Test Method, described herein.

TABLE 10

Hair Wet Combing (Instrom Triple Comb (ITC))

| Example | Mean (gf) | Standard Deviation |
|---|---|---|
| Ex. B | 336 | +/−28 |
| Ex. C | 210 | +/−49 |
| Ex. D | 227 | +/−8.0 |
| Ex. E | 248 | +/−48 |
| Ex. F | 275 | +/−16 |
| Ex. G | 729 | +/−122 |

Figure 2C:
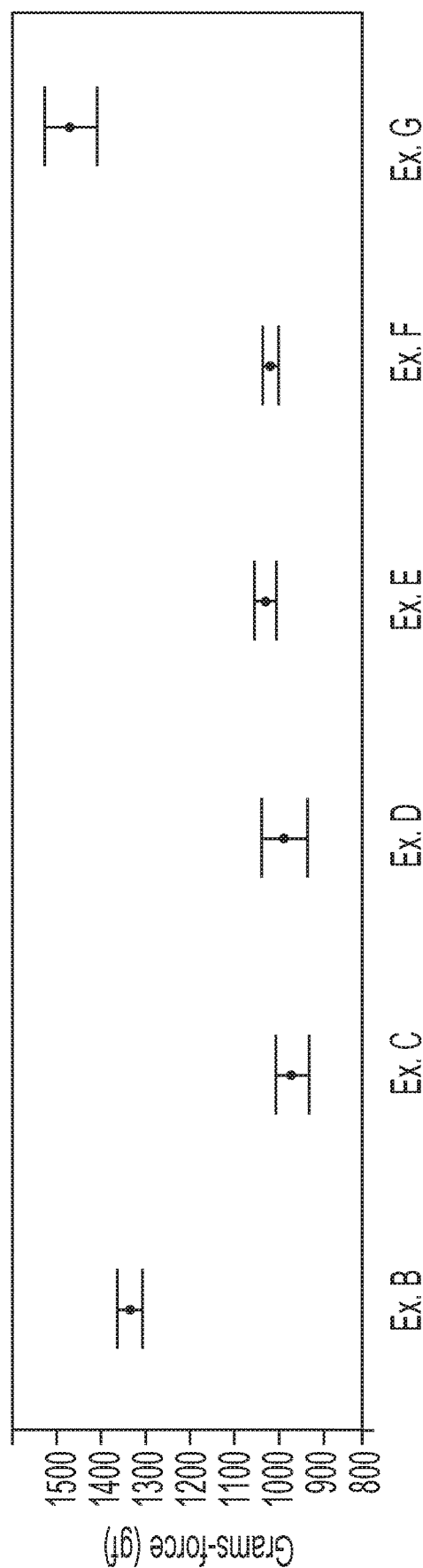
FIG. 2C compares the dry feel of Examples B to G.

Table 11 and FIG. 2C compare the dry feel of Examples B to G. The hair dry feel is determined by the Dry Feel Test Method, described herein.

TABLE 11

Dry Feel (Inter Fiber Friction (IFF))

| Example | Mean (gf) | Standard Deviation |
|---|---|---|
| Ex. B | 1331 | +/−27 |
| Ex. C | 949 | +/−38 |
| Ex. D | 966 | +/−53 |
| Ex. E | 1012 | +/−26 |
| Ex. F | 999 | +/−19 |
| Ex. G | 1474 | +/−65 |

Ex. C to F contain an experimental silicone (silicone a) and have wet conditioning and dry conditioning that is either better or as good as Ex. B, which contains DC 1872 silicone emulsion, an emulsion that is used in current products. Ex. C to F provide a significant improvement on dry feel that was not achievable with Ex. B. Therefore, Ex. C to F may be consumer preferred.

TABLE 12

Example H-Main Mix Composition

| | Ex. H (Wt. %) |
|---|---|
| Sodium Laureth Sulfate[1] | 12.0 |
| Sodium Lauryl Sulfate[2] | 7.0 |
| Cocamide Monoethanolamine (MEA)[3] | 1.7 |
| Preservative | 1.13 |
| pH adjuster | 0.36 |
| Water | Q.S. |

[1]Sodium Laureth 1 Sulfate, 26% active, supplied by Procter & Gamble MFG Co., Kansas City, USA
[2]Cocamidopropyl Betaine High pH at 30% active, from BASF ®
[3]Cocamide MEA flakes, 85% active, BASF ®

Next, a shampoo composition with 1% Silicone a (Ex. I) was compared to a shampoo composition with 1% silicone containing the DC 1872 silicone emulsion (Ex. J) to see if there was a consumer noticeable performance difference in later, wet feel, dry feel, and end look. Examples I and J are in Table 13.

TABLE 13

Translucent Shampoo Compositions

| | Ex. I | Ex. J |
|---|---|---|
| Sodium Laureth Sulfate[1] | 15 | 15 |
| Cocamidopropyl Betaine[2] | 2 | 2 |
| Guar Hydroxypropyltrimonium Chloride[3] | 0.15 | 0.15 |
| Polyquaternium-6[4] | 0.1 | 0.1 |
| Perfume | 0.80 | 0.80 |
| Stearyl Alcohol | 0.179 | 0.179 |
| Cetyl Alcohol | 0.322 | 0.322 |
| Preservative | 0.44 | 0.44 |
| pH Adjuster | 0-0.30 | 0-0.30 |
| Thickener | 0-2 | 0-2 |
| DC 1872[5] | — | 4.55 |
| Emulsion 4 | 2.86 | — |

[1]Sodium Laureth 1 Sulfate, 26% active, supplied by Procter & Gamble MFG Co., Kansas City, USA
[2]Cocamidopropyl Betaine High pH at 30% active, from BASF ®
[3]N-Hance ™ 3196, MW of 1.7 million, supplier: Ashland ™
[4]Polyquaternium 6, PolyDADMAC, MW of 150,000, CD of 6.2, trade name. Mirapol ® 100 s, 31.5% active, from Solvay
[5]DC 1872 silicone emulsion (dimethiconol) with an average particle size of 30 nm, from Dow Corning ®

Table 14, below, provides a summary of the panelists and their hair type in this study.

TABLE 14

Summary of Panelists

| Panelist | Gender | Hair Type | Conditioner |
|---|---|---|---|
| 1 | Female | Long, Fine Hair, All Over Highlights, B ⅓ Heavy Bleach | Yes, bottom ⅔ |
| 2 | Female | Shoulder Length, Fine Hair, Bleached and Colored B ⅓ | Yes, bottom ⅓ |
| 3 | Male | Short, Medium, Virgin Hair | Yes, all over |
| 4 | Female | Shoulder Length, Fine, Virgin Hair | Yes, all over |
| 5 | Female | Shoulder Length, Medium, Virgin Hair | Yes, all over* |
| 6 | Female | Shoulder Length, Coarse, Virgin Hair | Yes, all over |

*Conditioner used was Pantene ® Smooth & Sleek (Lot # (L)71605395HD, purchased 2018) instead of Pantene ® Sheer Volume The study was conducted at Procter & Gamble, Sharon Woods Innovation Center Salon (Sharonville, Ohio, USA) by a P&G employed stylist. The salon includes sinks that are standardized at 100° F. (37.8° C.) and 1.5 Gallon Per Minute (GPM) (5.7 liters per minute) water pressure.

1. Stylist begins by parting panelist's hair down the middle. One side of hair is clipped up and out of the way with a clip.

2. The stylist then wets the half of hair that remains down. Using a syringe, 5-10 mL (dependent on the amount of hair the panelist has) of one shampoo is then applied directly onto the hair on that side of their head.
3. The stylist lathers the shampoo on that side of the panelist's head while making observations focusing on the spread, speed of lather and feel of lather.
4. The stylist then rinses hair while making observations on rinse time, feel of hair during rinse and finger combing ability.
5. Once washed and rinsed completely, the stylist will clip the freshly washed hair up and out of the way. The stylist will then unclip the other half of hair and repeat Steps 2-4 on unwashed half of head with second product.
6. After both sides of head have been washed, the stylist will unclip both sides and make comparative wet detangling and wet feel of hair notes on both products.
7. Pantene® Sheer Volume conditioner (Lot #(L) 82565395CC, purchased Nov. 5, 2018), unless otherwise noted, is applied to entire head and rinsed off.
8. Panelists are then asked to use a brush and blow dryer to dry their hair as they normally would at home.
9. Stylist then makes final comparative evaluation of dry feel, time to dry, static, detangling, etc. post conditioner and styling between the two products.

Table 15 to Table 20, below, summarize the in-use observations of the study.

TABLE 15

Panelist 1

| | Left-Ex. I | Right-Ex. J |
|---|---|---|
| Amount Used | 10 ml | 10 ml |
| Lather | Lathered easily. Very cushiony. Large amount of lather. Lighter feel. Does not detangle well with fingers. | Speed to lather same as Ex. J. More slippery oily feel on skin. Not altering lather quality. Finger detangle much better. Get stuck bottom of strand-about two inches left. Lather slightly airier than Ex. J. |
| Rinse | Rinse easily. Feels clean. Finger detangles little better during rinse. Squeaky clean. | Slightly longer to rinse-more normal time length. Ex. J very quick. |
| Post | No leftover residue. Doesn't feel soft or conditioned. No slip. Just clean feel. Hair strands were more separated, not aligned. | More slippery feel on hair. No audible squeak like EX. I. Easier to finger detangle. Still feels clean but there's additional slip. More alignment than EX. I. |
| Dry | Cleaner feel with more volume. Fuller look. | More tangles while drying and combing out. More alignment, more shine. |
| Preference | Left (Ex. I)-preferred lack of tangles and cleaner, fuller look. | |

TABLE 16

Panelist 2

| | Left-Ex. I | Right-Ex. J |
|---|---|---|
| Amount Used | 5 ml | 5 ml |

TABLE 16-continued

Panelist 2

| | Left-Ex. I | Right-Ex. J |
|---|---|---|
| Lather | Copious amount of lather. Lathered quickly, dense. Slight cream. Cushiony feel. Finger detangled easily and to end last 2 in of strand. | Lathered quickly and easily. Large amount of lather. Bubbles slightly larger than Ex. I. More lather than Ex. I. Dense, slightly creamy but airy lather. Finger detangled easily and to end last 2 inches of strand. |
| Rinse | Rinse very quick. Squeak on hair during rinse. Audible squeak. | Rinse quick. Audible squeak during rinse, more than Ex. I. |
| Post | No slip, but very clean feel. No coating, leftover feel. But not stripped feel either. Finger detangled to bottom 2 in. easily. | Less aligned than Ex. I. Finger detangled to bottom 2 inches easily. Very clean feel. Less soft hair feel than Ex. I. |
| Dry | Feels rough to touch. After styling with flat iron, better smooth feeling. No static compared to right. | More tangled during comb and drying. Feels soft, aligned, smoother. Feels much better to touch. After styling with flat iron, felt flat on head. A lot of static. |
| Preference | Left (Ex. I)-preferred the fuller look and cleaner feel even though end feel wasn't as smooth, it signals to her that she can achieve the end look she desires. | |

TABLE 17

Panelist 3

| | Left-Ex. I | Right-Ex. J |
|---|---|---|
| Amount Used | 5 ml | 5 ml |
| Lather | Lathered very quickly. Worked through well. Cut through product on hair quickly and effectively. Very thick, soft, dense, conditioned lather. | Not as much lather generated as Ex. I. Texture of lather feels very similar. Slightly creamier than left. Feels softer on head. |
| Rinse | Rinsed fast—more texture to hair so not as quick as other panelists but quick. Rinsed with a squeak, audible. | Squeaky while rinsing, quicker rinse than Ex. I. Very clean feel. Audible squeak and drag on hair. |
| Post | Slightly smooth feel, not rough or coarse. Feels quite clean. | Less smooth than Ex. I. Subtle difference. |
| Dry | Subtle difference. | |
| Preference | Left (Ex. I)-no difference in dry but preferred wet feel more. Felt both cleaner and softer after rinse. | |

TABLE 18

Panelist 4

| | Left-Ex. I | Right-Ex. J |
|---|---|---|
| Amount Used | 10 ml | 10 ml |

TABLE 18-continued

Panelist 4

|  | Left-Ex. I | Right-Ex. J |
|---|---|---|
| Lather | Lather generated quickly. Very large airy bubbles. Takes a little work to finger detangle but can get through top ⅔ easily. | Spreads well. Lather generates quickly, time very similar to Ex. I. Some large bubbles but overall slightly denser than Ex. I. Finger detangles better to start and can get farther down the strand. Lather feels thicker in hair on head than Ex. I. |
| Rinse | Rinses easy and quickly. Rinsed with squeak, only slight. | During rinse, hair feels softer than left. More squeak during rinse. |
| Post | No slip. Feels very clean, no leftover residue. Difficult to finger detangle. | Smoother than left. Still has squeak but more slip. Subtle difference. |
| Dry Preference | Subtle difference. Left (Ex. I)-very subtle differences, both sides feel the same but left side looks better. Less flyaways and fuller look. | |

TABLE 19

Panelist 5

|  | Left-Ex. I | Right-Ex. J |
|---|---|---|
| Amount Used | 10 ml | 10 ml |
| Lather | Lather generated quickly, spread well in hair. Lather is airy with large bubbles. Finger detangles well, went through to bottom 2 in. The more work put into lather, the creamier, and dense it became. | Lathered quickly. Finger detangles better than Ex. I. Lather feels denser and more in amount. Lather generated to end point quicker than Ex. I. |
| Rinse | Rinsed very quickly. Feel some slip. Finger detangles down top ⅔. | Rinsed quickly Immediate almost slimy feel but disappears right away and becomes squeaky during rinse. |
| Post | Squeak. Feels clean. Doesn't feel rough or stripped but soft. More aligned and slightly smoother feel. | More squeak and more resistance on head. |
| Dry | More shine than right side. | Subtle differences. Slightly smoother |
| Preference | Left (Ex. I)-very subtle differences, both sides feel same in wet and dry but prefers end look. Left side lays nicer, feels more aligned, clean and softer. | |

TABLE 20

Panelist 6

|  | Left-Ex. I | Right-Ex. J |
|---|---|---|
| Amount Used | 10 ml | 10 ml |

TABLE 20-continued

Panelist 6

|  | Left-Ex. I | Right-Ex. J |
|---|---|---|
| Lather | Lathered quickly. Feels creamy on scalp. Light cushion, not very heavy. Feels thick near scalp. Dense. Finger detangles very well down entire strand of hair. Feels soft. | Lather generated similar speed slightly slower. Took more work to generate same amount and texture of thick, creamy lather. Finger detangles same. Hair strand not as smooth as left. |
| Rinse | Rinses very easily. Finger detangles very well. Little squeak. | Feel smooth, slippery but immediate goes away and squeaks more than left. |
| Post | Feel more of the hair strand. Feels clean but more like soft wet hair. | Feels softer and smoother than left. Still clean feel. |
| Dry | Slightly rougher feel. | Smoother feel. |
| Preference | Right (Ex. J)-very subtle difference, both sides feel similar in wet and dry but prefers end look. Right side was smoother, more aligned. | |

Overall, Ex. I, which contains Silicone a, was preferred by the panelists 5-1 over Ex. J, which contains the DC 1872 emulsion that is currently used. Overall, the panelists thought that Ex. I had a quicker and cleaner rinse profile without a stripping feel, which can be consumer preferred. The panelists also commented that the post-rinse profile for Ex. I tended to be cleaner than Ex. J. The differences at dry end feel were most noticeable and this ultimately led 5 of the panelists to prefer Ex. I because they found the end look to feel fuller, cleaner, softer, more aligned and less static.

In some examples, it can be desirable to use the silicone described herein in a low viscosity, compact shampoo composition. The composition can be phase stable, color stable, and can also provide good conditioning during use. The shampoo composition can be clear, transparent, or opaque. An opaque composition can have a % transmittance of 30% or less, as determined by the % Transmittance Test Method, described herein.

In other examples, the shampoo can be dispensed from an aerosol or pump foam dispenser as a foam. The foam can form a stable foam. A foam is stable when it substantially sustains its volume from the time of dispensing to its application on hair. The foam can have a density of from about 0.025 g/cm$^3$ to about 0.15 g/cm$^3$ when dispensed from the aerosol dispenser.

For the Examples in Table 21, the microemulsion of Silicone can be formed by mixing 2 g of Silicone a and 1 g of Tergitol™ 15-S-5 (available from Dow®). Mixing can be continued while 6.93 g of water is added dropwise. Then, 0.07 g lactic acid is added and a transparent to slightly turbid microemulsion is obtained.

TABLE 21

Shampoo Compositions and Results

|  | Ex. 1 | Ex. 2 | Comp. 1 | Comp. 2 | Comp. 3 |
|---|---|---|---|---|---|
| Mean Post Rinse Combing | 6.0 | 6.0 | 3.8 | 4.8 | 4.3 |
| Foam density (g/ml) | 0.056 | 0.058 | 0.055 | 0.075 | 0.062 |
| Foam Yield (Pa) | 14.2 | 14.7 | 11.7 | 13.1 | 14.7 |
| Bulk Viscosity (cP) | 61 | 79 | 138 | 112 | 813 |

TABLE 21-continued

Shampoo Compositions and Results

| | Ex. 1 | Ex. 2 | Comp. 1 | Comp. 2 | Comp. 3 |
|---|---|---|---|---|---|
| Sodium Chloride | 1.75 | 1.75 | 1.75 | 1.75 | 1.75 |
| Sodium Laureth Sulfate (SLE1S)[1] | 26 | 26 | 26 | 26 | 26 |
| Sodium Xylene Sulfonate[2] | 2.4 | 2.4 | 2.4 | 2.4 | 2.4 |
| Guar Hyrdroxypropyltrimonium Chloride (Jaguar ® C500)[3] | 0.4 | 0.4 | 0.4 | 0.4 | 0.4 |
| Silicone a[4] | 4 | | | | |
| Silicone b[5] | | 4 | | | |
| Comparative Silicone[6] | | | 4 | | |
| ABIL ® ME45[7] | | | | 4 | |
| DC 1872[8] | | | | | 4 |
| Fragrance | 2.4 | 2.4 | 2.4 | 2.4 | 2.4 |
| Propellant (A46)[9] | 4 | 4 | 4 | 4 | 4 |
| Citric Acid | 0.5 | 0.5 | 0.5 | 0.5 | 0.5 |
| Water and Minors (Q.S. to 100%) | Q.S. | Q.S. | Q.S. | Q.S. | Q.S. |

Example 1 and 2, which contain Silicone a and b, respectively, may be consumer preferred because they provide better post rinse combing than Comparative Examples 1-4. The post rinse combing is determined by ten expert panelists who comb a hair switch and rate give it a rating from 1-10, with 10 being the easiest to comb.

Table 22 includes shampoo compositions that can be dispensed as a foam.

TABLE 22

Foamed Shampoo Compositions

| | Compositions | | | | | | | |
|---|---|---|---|---|---|---|---|---|
| | Ex. 3 | Ex. 4 | Ex. 5 | Ex. 6 | Ex. 7 | Ex. 8 | Ex. 9 | Ex. 10 |
| Foam density (g/ml) | 0.079 | 0.083 | 0.074 | 0.077 | 0.057 | 0.056 | 0.085 | 0.085 |
| Foam Yield (Pa) | 3.90 | 3.64 | 4.13 | 3.85 | 4.89 | 9.12 | 1.95 | 3.57 |
| Bulk Viscosity (cP) | 61 | 79 | 426 | 241 | 373 | 362 | 373 | 362 |
| Total Surfactant | 26 | 26 | 26 | 26 | 30 | 30 | 30 | 30 |
| Sodium Chloride | 1.75 | 1.75 | 0.5 | 0.5 | 1.0 | 1.0 | 1.0 | 1.0 |
| Sodium Laureth Sulfate (SLE1S)[1] | 26 | 26 | 26 | 26 | | | | |
| Sodium Undeceth Sulfate (C11E1S)[11] | | | | | 24 | 24 | 24 | 24 |
| Lauramidopropyl Betaine (LAPB 35% active)[12] | | | | | 6 | 6 | 6 | 6 |
| Sodium Xylene Sulfonate[2] | 2.4 | 2.4 | | | | | | |
| Dipropylene Glycol | | | 4 | 4 | 6 | 6 | 6 | 6 |
| Guar Hyrdroxypropyltrimonium Chloride (Jaguar ® C500)[3] | 0.4 | 0.4 | 0.4 | 0.4 | 0.4 | 0.4 | 0.4 | 0.4 |
| Silicone a[4] | 4 | | 4 | | 4 | | 4 | |
| Silicone b[5] | | 4 | | 4 | | 4 | | 4 |
| Fragrance | 2.4 | 2.4 | 2.4 | 2.4 | 2.4 | 2.4 | 2.4 | 2.4 |
| Propellant (A46)[9] | | | | | 4 | 4 | | |
| Propellant (HFO)[10] | 7 | 7 | 7 | 7 | | | 7 | 7 |
| Citric Acid | 0.5 | 0.5 | 0.5 | 0.5 | 0.5 | 0.5 | 0.5 | 0.5 |
| Water and Minors (QS to 100%) | QS | QS | QS | QS | QS | QS | QS | QS |

[1] Sodium Laureth (1 molar ethylene oxide) sulfate at 70% active, supplier: Stepan Co.

[2] Sodium Xylene Sulfonate from Stepan Company

[3] Jaguar ® C500, MW of 500,000, CD of 0.8, from Solvay

[4] Experimental silicone polymer, according to the structure described herein, containing polyorganosiloxane compounds where the silicone blocks contain an average of 145 repeating siloxane units.

[5] Experimental silicone polymer, according to the structure described herein, containing polyorganosiloxane compounds where the silicone blocks contain an average of 110 repeating siloxane units.

6. Comparative silicone contains an average of 50 repeating siloxane units.

7. Silicone quaternium micro-emulsion, 30% active, ABIL ® ME 45, from Evonik

8. DC 1872 silicone emulsion (dimethiconol) with an average particle size of 30 nm, from Dow Corning

[9] Foaming Agent A46 (a mixture of 84.85% by weight of isobutane and 15.15% by weight of propane) Diversified Cpc International (Channahon US)

[10] Blowing Agent HF0 (Trans 1,3,3,3 Tetrafluroprop-1-ene) from Honeywell

[11] Sodium Undeceth Sulfate (C11E1S, Isachem 123S, 1 mole of Ethoxylation) at 70% active, supplier: Procter & Gamble ®

[12] LAPB (Mackam DAB), at 35% active level, supplier: Rhodia

Test Methods

Cone/Plate Viscosity Measurement

The viscosities of the examples are measured by a Cone/Plate Controlled Stress Brookfield Rheometer R/S Plus, by Brookfield Engineering Laboratories, Stoughton, Mass. The cone used (Spindle C-75-1) has a diameter of 75 mm and 1° angle. The viscosity is determined using a steady state flow experiment at constant shear rate of $2\ s^{-1}$ and at temperature of 26.5° C. The sample size is 2.5 ml and the total measurement reading time is 3 minutes.

Foam Density & Foam Volume

Foam density is measured by placing a 100 ml beaker onto a mass balance, tarring the mass of the beaker and then dispensing product from the aerosol container into the 100 ml beaker until the volume of the foam is above the rim of the vessel. The foam is made level with the top of the beaker by scraping a spatula across it within 10 seconds of dispensing the foam above the rim of the vessel. The resulting mass of the 100 ml of foam is then divided by the volume (100) to determine the foam density in units of g/ml.

Foam volume is measured by placing a weigh boat onto a mass balance, tarring the mass of the weigh boat and then dispensing the desired amount of product from the aerosol container. The grams of foam dispensed is determined and then divided by the density of foam as determined from the Foam Density methodology to reach a volume of foam in ml or $cm^3$.

Foam Rheology Method (Yield Point)

Foam shampoo is applied to the AR1000 rheometer for foam oscillation stress sweep. 60 mm smooth acrylic plate is utilized for shear stress measurement. Measurement is made at 25 C. The plate head is lowered to 1200 microns and excess foam is removed with a spatula so that drag does not occur during measurement. The measurement gap height is then lowered 1000 microns. Sweep occurs from 0.1 to 400 Pa. Data is analyzed via TA Rheology Advantage Data Analysis software. Yield point is determined at the point at which the oscillatory shear stress begins to deviate from its tangent. The yield point measurements are reported in Pa units.

Kruss Lather Analyzer (Bubble Size)

The commercially available Kruss lather analyzer DFA100, supplied from Kruss, is used to analyze the foam shampoo for the initial Sauter mean radius $R_{32}$ (bubble size). Shampoo foam is dispensed into the CY4571 column containing a prism. An internal stopper is placed into the column approximately 100 ml from the top of the chamber. The camera height is set to 244 mm and camera position is placed in the 3 slot. Structure foaming is captured at 2 frames per second for 120 seconds. Data analysis is performed on the Kruss Advance 1.5.1.0 software application version.

Silicone Deposition (ppm) Test Method:

Hair samples treated with different products are submitted as balls of hair with an average sample size of 0.1 g. These hair samples are then digested using a single reaction chamber microwave digestion system (Milestone Inc., Shelton, Conn.) using a 6:1 $HNO_3:H_2O_2$ mixture and an aliquot of methyl isobutyl ketone (MIBK) in Teflon digestion vessels. A gentle digestion program with a ramp to 95° C. and a manual vent after cooling below 30° C. is used to facilitate retention of silicon. After dilution to volume, the samples are run against an inorganic silicon calibration curve produced on an Optima 8300 ICP-OES system (Perkin Elmer, Waltham, Mass.) run in the axial mode. The silicon values determined are converted to a concentration of silicone polymer-equivalents deposited on the hair sample using the theoretical silicon concentration of the polymer provided by the manufacturer. An untreated hair sample is analyzed to determine the background concentration of silicon to allow correction if needed. Another untreated hair sample is spiked with a known amount of polymer and analyzed to ensure recovery of the polymer and verify the analysis.

Dry Feel (Inter Fiber Friction, IFF)

The inter-fiber friction method emulates the motion of rubbing hair between the thumb and index finger in an up and down direction. The method evaluates the hair to hair interaction of dried hair switches, determining the hair static friction, which is a key component of hair volume. The hair switches that weigh 4 g and. have a length of 8 inches with a configuration of round pony tail.

The switches are treated with shampoo. For shampoos in liquid form, 0.2 ml of a liquid shampoo is applied on the hair switch in a zigzag pattern uniformly to cover the entire hair length, using a syringe. For shampoo in aerosol foam form, foam shampoo is dispensed to a weighing pan on a balance and 0.2 grams of foam shampoo is taken out from weighing pan and applied on the hair switch uniformly to cover the entire hair length via a spatula. The hair switch is then lathered for 30 seconds, rinsed with water for 30 seconds, and dried overnight in a controlled temperature and humidity room (22° C./50 RH).

A TA-XT plus Texture Analyzer (by Stable Micro Systems) or equivalent piece of equipment is used for the evaluation. The switch, after combing 5 times to remove tangles, is sandwiched between two plates with polyurethane skin surrogate substrate surfaces (skin flex paint, supplied by Burman Industries) under pressure of 40 psi (275.8 kPa), at 10 mm/sec. The plates can move up and down with a speed of 10 mms and a distance of each cycle of 200 mm for 5 cycles. Each of the peak forces for the 5 cycles are added to calculate Peak Sum which represents the static friction of hair. The static force correlates with consumer's hair smooth feel. Therefore, the higher the static force the larger the value the coarser the hair. The measurement is repeated for each hair switch.

Hair Wet Feel Friction Measurement (Final Rinse Friction and Initial Rinse Friction):

A switch of 4 grams general population hair at 8 inches length is used for the measurement. Water temperature is set at 100° F., hardness is 7 grain per gallon, and flow rate is 1.6 liter per minute. For shampoos in liquid form, 0.2 ml of a liquid shampoo is applied on the hair switch in a zigzag pattern uniformly to cover the entire hair length, using a syringe. For shampoo in aerosol foam form, foam shampoo is dispensed to a weighing pan on a balance. 0.2 grams of foam shampoo is taken out from weighing pan and applied on the hair switch uniformly to cover the entire hair length via a spatula. The hair switch is then lathered for 30 seconds, rinse with water for 30 seconds, and 2nd lathered for 30 seconds. Water flow rate is then reduced to 0.2 liter per minute. The hair switch is sandwiched with a clamp under 1800 gram of force and pulled through the entire length while the water is running at the low flow rate. The pull time is 30 second. Friction is measured with a friction analyzer with a load cell of 5 kg. Repeat the pull under rinse for total of 21 times. Total 21 friction values are collected. The final rinse friction is the average friction of the last 7 points and initial rinse friction is the average of the initial 7 points.

% Transmittance

The percent transmittance (% T) can be measured using Ultra-Violet/Visible (UV/VI) spectrophotometry which determines the transmission of UV/VIS light through a sample. A light wavelength of 600 nm has been shown to be adequate for characterizing the degree of light transmittance through a sample. Typically, it is best to follow the specific instructions relating to the specific spectrophotometer being used. In general, the procedure for measuring percent transmittance starts by setting the spectrophotometer to 600 nm. Then a calibration "blank" is run to calibrate the readout to 100 percent transmittance. A single test sample is then placed in a cuvette designed to fit the specific spectrophotometer and care is taken to insure no air bubbles are within the sample before the % T is measured by the spectrophotometer at 600 nm. Alternatively, multiple samples can be measured simultaneously by using a spectrophotometer such as the SpectraMax M-5 available from Molecular Devices. Multiple samples can be prepared within a 96 well plate (VWR catalog #82006-448) and then transferred to a 96 well visible flat bottom plate (Greiner part #655-001), ensuring that no air bubbles are within the sample. The flat bottom plate is placed within the SpectraMax M-5 and % T measured using the Software Pro v.5™ software available from Molecular Devices.

Wet Combing Test (Instron Triple Comb, ITC)

This wet friction test determines the amount of conditioning provided by shampoo products as measured by the force required to pull hair through an Instron® equipped with three combs while wet. An Instron® 5542 or 5543 Tensile Tester with an attachment for combing hair switches and an Instron® 2530-437 50N tension/compression load cell is used. The operator ranks and balances the 4 g, 8 in. general population hair switches for base line condition by using the Instron® machine to determine a baseline force. The operator then applies 0.1 g of shampoo per gram of hair to a hair switch, distributing the product evenly through the switch. The wet forces are then measured after the product is rinsed using the Instron® machine equipped with three aligned combs simultaneously (the combs are arranged as follows: Cleopatra™ fine tooth, a second Cleopatra™ fine tooth, and a Cleopatra™ wide tooth comb) pulling at a rate of 17 mm/sec reading data every 0.5 sec. Each test product is applied to a total of 4 switches. The switches are mounted on the instrument and the force required to comb the switches measured. In all experiments at least 5 readings are performed on each switch and at least 3 switches are used for each treatment. The data is then analyzed using standard statistical methods. Coarse Stroke 1 is the data point on the wide tooth comb at the first comb point.

Combinations

A. A compact shampoo composition exhibiting good conditioning, wherein the composition comprises:
  a. from about 0.5% to about 8% of one or more silicones, by weight of the composition and wherein at least one of the silicone is a polyorganosiloxane compound comprising:
    i. one or more quaternary ammonium groups;
    ii. silicone blocks comprising from about 99 and about 199 siloxane units on average; and
    iii. at least one polyalkylene oxide structural unit; and
    iv. at least one terminal ester group;
  b. from about 4% to about 45%, by weight, of a detersive surfactant;
  wherein the concentrated shampoo composition has a liquid phase viscosity of from about 1 centipoise to about 8,000 centipoise;
  wherein the concentrated shampoo composition is dispensible as a foam from a dispenser.

B. The compact shampoo composition according to Paragraph A, wherein the silicone blocks comprise on average from about 110 to about 199 siloxane units, preferably from about 115 to about 175 siloxane units, more preferably from about 120 to about 155 siloxane units, and even more preferably between 130 and 150 siloxane units on average.

C. The compact shampoo composition according to Paragraphs A-B, wherein the silicone blocks comprise on average alternatively about 155 to about 199 siloxane units, preferably from about 155 to about 190 siloxane units, and preferably from about 155 to about 175 siloxane units.

D. The compact shampoo composition according to Paragraphs A-C, wherein the silicone blocks comprise on average from about 100 to about 150 siloxane units, preferably from about 105 to about 140 siloxane units, and even more preferably from about 110 to about 130 siloxane units.

E. The compact shampoo composition according to Paragraphs A-D, wherein the wherein at least one of the silicone is a polyorganosiloxane has the following structure:

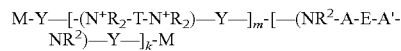

$$M-Y-[-(N^+R_2\text{-}T\text{-}N^+R_2)-Y-]_m-[-(NR^2\text{-}A\text{-}E\text{-}A'\text{-}NR^2)-Y-]_k-M$$

wherein:
  m is >0, preferably 1 to 100, more preferably 1 to 50, and even more preferably 1 to 10;
  k is 0 to 50, preferably 0 to 20, preferably 0 to 10;
  M represents a terminal group, comprising terminal ester groups selected from

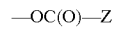

—OC(O)—Z wherein Z is selected from monovalent organic residues having up to 40 carbon atoms;
  A and A' each are independently from each other selected from a single bond or a divalent organic group having up to 10 carbon atoms and one or more hetero atoms; and
  E is a polyalkylene oxide group of the general formula:

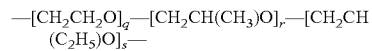

$$-[CH_2CH_2O]_q-[CH_2CH(CH_3)O]_r-[CH_2CH(C_2H_5)O]_s-$$

wherein q=0 to 200, preferably 0 to 100, more preferably 1 to 50, and even more preferably 1 to 10;
  r=0 to 200, preferably 0 to 100, more preferably 0 to 25 and even more preferably 0 to 10;
  s=0 to 200, preferably 0 to 100, more preferably 0 to 25, and even more preferably 0 to 10;
  and q+r+s=1 to 600, preferably 1 to 100, more preferably 1 to 50, and even more preferably 1 to 30;
  with percentage of q (q/(q+r+s)) 1% to 100%, preferably 10% to 100%, more preferably 30% to 100%, and even more preferably 50% to 100%;
  $R^2$ is selected from hydrogen or R,
  R is selected from monovalent organic groups having up to 22 carbon atoms; and wherein the free valencies at the nitrogen atoms are bound to carbon atoms,
  Y is a group of the formula:

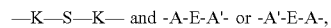

—K—S—K— and -A-E-A'- or -A'-E-A-, with S=

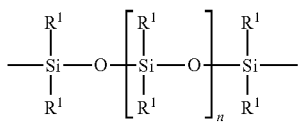

wherein R1=$C_1$-$C_{22}$-alkyl, $C_1$-$C_{22}$-fluoralkyl or aryl; n=99 to 199 on average, preferably 110 to 199 on average, preferably 130 to 190 on average, more preferably 120 to 175 on average, and even more preferably 110 to 155 on average, and these can be identical or different if several S Groups are present in the polyorganosiloxane compound;

K is a bivalent or trivalent straight chain, cyclic and/or branched $C_2$-$C_{40}$ hydrocarbon residue which is optionally interrupted by —O—, —NH—, trivalent N, —$NR^1$—, —C(O)—, —C(S)—, and optionally substituted with —OH, wherein $R^1$ is defined as above, T is selected from a divalent organic group having up to 20 carbon atoms.

F. The compact shampoo composition according to Paragraph E wherein:
k is 0;
M represents a terminal group, comprising terminal ester groups selected from

wherein Z is selected from monovalent organic residues having up to 20 carbon atoms;
A and A' each are independently from each other selected from a single bond or a divalent organic group having up to 10 carbon atoms and one or more hetero atoms; and
E is a polyalkylene oxide group of the general formula:

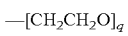

wherein q=1 to 10;
Y is a group of the formula:

with S=

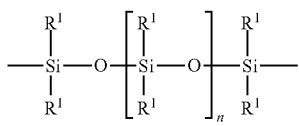

wherein R1=$C_1$-$C_{22}$-alkyl, $C_1$-$C_{22}$-fluoralkyl or aryl; n=105 to 180 on average, and these can be identical or different if several S Groups are present in the polyorganosiloxane compound.

G. The compact shampoo composition according to Paragraphs A-F, wherein the one or more silicones is in the form of a nanoemulsion.

H. The compact shampoo composition according to Paragraphs A-G, wherein the average particle size of the one or more silicones is from about 1 nm to about 100 nm, preferably from about 5 nm to about 80 nm, more preferably from about 10 nm to about 60 nm.

I. The compact shampoo composition according to Paragraphs A-I, wherein the polyorganosiloxane compound comprises a nitrogen content from about 0.1 to about 0.4 mmol N/g polyorganosiloxane, preferably from about 0.1 to about 0.3 mm N/g polymer, and more preferably from about 0.13 to about 0.27 mmol N/g polymer J. The compact shampoo composition according to Paragraphs A-I, wherein the concentrated shampoo composition comprises from about 1% to about 5% of the one or more silicones, by weight of the concentrated shampoo composition.

K. The compact shampoo composition according to Paragraphs A-K, wherein the detersive surfactant comprises from about 15% to about 45%, preferably from about 10% to about 40%, more preferably from about 12% to about 35%, and even more preferably from 15% to about 30%.

L. The compact shampoo composition according to Paragraphs A-K, wherein the composition further comprises from about 0.1% to about 25%, by weight of the composition, preferably from about 0.5% to about 15%, and more preferably from about 1% to about 10%, of one or more co-surfactants selected from the group consisting of amphoteric surfactant, zwitterionic surfactant, non-ionic surfactant and mixtures thereof.

M. The compact shampoo composition according to Paragraphs A-L, further comprising from about 0.01% to about 2%, preferably from about 0.05% to about 1.8%, more preferably from about 0.05% to about 1.5%, and even more preferably from about 0.05% to about 0.9% of cationic polymer by weight, cationic polymer wherein the cationic polymer comprises an average molecular weight from about 50,000 g/mol to about 1,200,000 g/mol, preferably from 100,000 to 1,000,000 g/mol.

N. The compact shampoo composition according to Paragraph M, wherein the cationic polymer is selected from the group consisting of polyquaternium-6, polyquaternium-76, guar hydroxypropyltrimonium, chloride, non-guar galactomannan polymer, and combinations thereof.

O. The compact shampoo composition according to Paragraphs A-N, wherein the shampoo composition has a viscosity from about 10 cP to about 6000 cP, preferably from about 25 cP to about 5000 cP, more preferably from about 40 cP to about 3000 cP, and even more preferably from about 50 cP to about 3000 cP.

P. The compact shampoo composition according to Paragraphs A-O, wherein the shampoo composition further comprises an anti-dandruff active selected from the group consisting of piroctone olamine, pyridinethione salts, azoles, selenium sulfide, particulate sulfur, salicylic acid, zinc pyrithione, and mixtures thereof.

Q. A method of treating hair, the method comprising:
a. applying to the hair the shampoo composition according to Paragraphs A-P, wherein the shampoo composition is dispensed from an aerosol dispenser or a pump foam dispenser as a dosage of foam;
b. rinsing the shampoo composition.

R. The method according to Paragraph Q, wherein the shampoo composition is dispensed from an aerosol dispenser as a foam and wherein the shampoo composition further comprises from about 2% to about 12%, preferably from about 3% to about 10%, and more preferably from about 5% to about 8%, by weight of the composition, propellant wherein the propellant is selected from the group consisting of propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoroprop-1-ene, and combinations thereof.

S. The method according to Paragraph R, wherein the propellant comprises trans-1,3,3,3-tetrafluoroprop-1-ene.

T. The method according to Paragraphs Q-S, wherein the foam has a density of from about 0.010 g/cm$^3$ to about 0.50 g/cm$^3$, preferably from about 0.02 g/cm$^3$ to about 0.40 g/cm$^3$, and more preferably from about 0.03 g/cm$^3$ to about 0.35 g/cm$^3$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shampoo composition comprising:
   a. a silicone emulsion comprising:
      i. an emulsifier; wherein the emulsifier is selected from the group consisting of laureth-9, C11-15 pareth-7, ceteareth-25, trideceth-3, glycerin, and combinations thereof;
      ii. from about 0.1% to about 10% of one or more silicones, by weight of the composition, wherein the average particle size of the one or more silicones is from about 1 nm to about 100 nm, and wherein at least one of the silicones is a polyorganosiloxane compound comprising:
         1. one or more quaternary ammonium groups;
         2. silicone blocks comprising between about 99 and about 199 siloxane units on average;
         3. at least one polyalkylene oxide structural unit; and
         4. at least one terminal ester group;
      wherein the ratio of emulsifier to silicone is from about 0.35 to about 0.6; and
   b. from about 4% to about 45%, by weight, of a detersive surfactant, wherein the shampoo composition is clear.

2. The clear shampoo composition of claim 1, wherein the silicone blocks comprise between about 105 and about 180 siloxane units on average.

3. The clear shampoo composition of claim 2, wherein the silicone blocks comprise between about 130 and about 150 siloxane units on average.

4. The clear shampoo composition of claim 1, wherein the wherein at least one of the silicone is a polyorganosiloxane has the following structure:

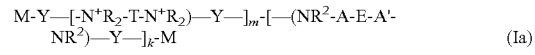

(Ia)

wherein:
m is 1 to 20;
k is 0 to 10;
M represents a terminal group, comprising terminal ester groups selected from

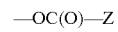

wherein Z is selected from monovalent organic residues having up to 40 carbon atoms;
A and A' each are independently from each other selected from a single bond or a divalent organic group having up to 10 carbon atoms and one or more hetero atoms; and
E is a polyalkylene oxide group of the general formula:

wherein q=1 to 10, r=0 to 10, s=0 to 10, and q+r+s=1 to 30, with percentage of q (q/(q+r+s)) at least 50%;
$R^2$ is selected from hydrogen or R,
R is selected from monovalent organic groups having up to 22 carbon atoms; and
wherein the free valencies at the nitrogen atoms are bound to carbon atoms,
Y is a group of the formula:

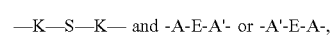

with S=

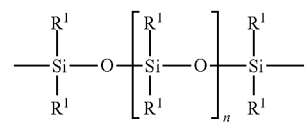

wherein R1=$C_1$-$C_{22}$-alkyl, $C_1$-$C_{22}$-fluoralkyl or aryl; n=99 to 199 on average, and these can be identical or different if several S Groups are present in the polyorganosiloxane compound;
K is a bivalent or trivalent straight chain, cyclic and/or branched $C_2$-$C_{40}$ hydrocarbon residue which is optionally interrupted by —O—, —NH—, trivalent N, —$R^1$—, —C(O)—, —C(S)—, and optionally substituted with —OH, wherein $R^1$ is defined as above,
T is selected from a divalent organic group having up to 20 carbon atoms.

5. The clear shampoo composition of claim 3 wherein:
m is 1 to 10;
k is 0;
M represents a terminal group, comprising terminal ester groups selected from

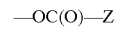

wherein Z is selected from monovalent organic residues having up to 20 carbon atoms;

A and A' each are independently from each other selected from a single bond or a divalent organic group having up to 10 carbon atoms and one or more hetero atoms; and E is a polyalkylene oxide group of the general formula:

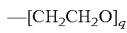

wherein q=1 to 10;

Y is a group of the formula:

with S=

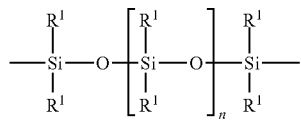

wherein R1=$C_1$-$C_{22}$-alkyl, $C_1$-$C_{22}$-fluoralkyl or aryl; n=105 to 180 on average, and these can be identical or different if several S Groups are present in the polyorganosiloxane compound.

6. The clear shampoo composition of claim 1, wherein the average particle size of the one or more silicones is from about 1 nm to about 100 nm with a polydispersity index of less than 0.2.

7. The clear shampoo composition of claim 6, wherein the average particle size of the one or more silicones is about 10 nm to about 60 nm with a polydispersity index of less than 0.2.

8. The compact shampoo composition of claim 1 wherein the polyorganosiloxane compound comprises a nitrogen content from about 0.1 to about 0.4 mmol N/g polyorganosiloxane.

9. A method to clean hair comprising:
a. wetting the hair;
b. applying the clear shampoo composition of claim 1 to the wet hair;
c. massaging into wet hair and forming a lather;
d. rinsing the shampoo composition.

10. The method of claim 9 wherein a general population hair switch comprises a mean final rinse friction from about 1100 gf to about 1500 gf.

11. The method of claim 9 wherein a general population hair switch comprises a mean Coarse Stroke 1 from about 50 gf to about 300 gf.

12. The method of claim 9 wherein a general population hair switch comprises a mean dry feel of from about 1000 gf to about 1600 gf.

13. The method of claim 9 wherein a general population hair switch comprises a mean silicone deposition of less than 250 ppm.

14. A method to clean hair comprising:
a. wetting the hair;
b. applying the clear shampoo composition of claim 1 to the wet hair, wherein the shampoo composition is dispensed from an aerosol dispenser or a pump foam dispenser as a dosage of foam;
c. massaging the dosage of foam into wet hair;
d. rinsing the shampoo composition.

15. The method of claim 14 wherein the shampoo composition has a viscosity from about 1 cP to about 3000 cP.

16. The method of claim 14, wherein the shampoo composition is dispensed from an aerosol dispenser as a foam and wherein the shampoo composition further comprises from about 2% to about 10%, by weight of the composition, propellant wherein the propellant is selected from the group consisting of propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and combinations thereof.

17. The method of claim 16 wherein the propellant comprises trans-1,3,3,3-tetrafluoropropene.

18. The method of claim 16 wherein the foam has a density of from about 0.02 g/cm³ to about 0.4 g/cm³.

* * * * *